United States Patent
Carrigan et al.

(10) Patent No.: US 11,135,305 B2
(45) Date of Patent: *Oct. 5, 2021

(54) METHODS FOR INCREASING EFFICACY OF FOLR1 CANCER THERAPY

(71) Applicant: ImmunoGen, Inc., Waltham, MA (US)

(72) Inventors: Christina N. Carrigan, Belmont, MA (US); Kathleen R. Whiteman, Wilmington, MA (US); Gillian Payne, Waban, MA (US); Sharron Ladd, Burlington, MA (US)

(73) Assignee: ImmunoGen, Inc., Waltham, MA (US)

( * ) Notice: Subject to any disclaimer, the term of this patent is extended or adjusted under 35 U.S.C. 154(b) by 524 days.

This patent is subject to a terminal disclaimer.

(21) Appl. No.: 15/807,831

(22) Filed: Nov. 9, 2017

(65) Prior Publication Data

US 2018/0200383 A1 Jul. 19, 2018

Related U.S. Application Data

(63) Continuation of application No. 14/245,797, filed on Apr. 4, 2014, now abandoned, which is a continuation of application No. 13/435,857, filed on Mar. 30, 2012, now Pat. No. 8,709,432.

(60) Provisional application No. 61/471,007, filed on Apr. 1, 2011.

(51) Int. Cl.
| | |
|---|---|
| *A61K 39/395* | (2006.01) |
| *G01N 33/53* | (2006.01) |
| *G01N 33/577* | (2006.01) |
| *G01N 33/574* | (2006.01) |
| *C07K 16/28* | (2006.01) |
| *A61K 47/68* | (2017.01) |
| *A61K 39/00* | (2006.01) |

(52) U.S. Cl.
CPC ...... *A61K 47/6851* (2017.08); *A61K 47/6809* (2017.08); *A61K 47/6849* (2017.08); *A61K 47/6869* (2017.08); *C07K 16/28* (2013.01); *G01N 33/57492* (2013.01); *A61K 39/395* (2013.01); *A61K 2039/505* (2013.01); *G01N 33/577* (2013.01); *G01N 2800/52* (2013.01)

(58) Field of Classification Search
CPC .............. A61K 39/395; A61K 47/6809; A61K 47/6849; A61K 47/6851; A61K 47/6869; C07K 16/28; C07K 16/30; G01N 33/53; G01N 33/57492; G01N 2800/00; G01N 2800/52

See application file for complete search history.

(56) References Cited

U.S. PATENT DOCUMENTS

| | | | |
|---|---|---|---|
| 5,416,016 A | 5/1995 | Low et al. | |
| 5,720,954 A | 2/1998 | Hudziak et al. | |
| 5,855,866 A | 1/1999 | Thorpe et al. | |
| 6,051,230 A | 4/2000 | Thorpe et al. | |
| 7,033,594 B2 | 4/2006 | Low et al. | |
| 7,112,317 B2 | 9/2006 | Thorpe et al. | |
| 7,125,541 B2 | 10/2006 | Thorpe et al. | |
| 7,740,854 B2 | 6/2010 | Low et al. | |
| 8,124,083 B2 | 2/2012 | Grasso et al. | |
| 8,236,319 B2 | 8/2012 | Chari et al. | |
| 8,388,972 B2 | 3/2013 | Martin et al. | |
| 8,557,966 B2 | 10/2013 | Ab et al. | |
| 8,709,432 B2 | 4/2014 | Carrigan et al. | |
| 8,795,673 B2 | 8/2014 | Li et al. | |
| 9,133,275 B2 | 9/2015 | Ab et al. | |
| 9,200,073 B2 | 12/2015 | Carrigan et al. | |
| 9,598,490 B2 | 3/2017 | Ab et al. | |
| 9,637,547 B2 | 5/2017 | Ab et al. | |
| 9,657,100 B2 | 5/2017 | Ab et al. | |
| 9,670,278 B2 | 6/2017 | Ab et al. | |
| 9,670,279 B2 | 6/2017 | Ab et al. | |
| 9,670,280 B2 | 6/2017 | Ab et al. | |
| 9,702,881 B2 | 7/2017 | Carrigan et al. | |
| 10,017,578 B2 | 7/2018 | Ab et al. | |
| 10,172,875 B2 | 1/2019 | Ponte | |
| 10,792,372 B2 | 10/2020 | Widdison | |
| 2003/0028009 A1 | 2/2003 | Huse | |
| 2003/0148406 A1 | 8/2003 | King et al. | |
| 2003/0157090 A1 | 8/2003 | Benvenuto et al. | |
| 2003/0229208 A1 | 12/2003 | Queen et al. | |
| 2003/0233675 A1 | 12/2003 | Cao et al. | |
| 2004/0031072 A1 | 2/2004 | La Rosa et al. | |
| 2004/0087478 A1 | 5/2004 | Gillen et al. | |
| 2004/0157214 A1 | 8/2004 | McCafferty et al. | |
| 2004/0170630 A1 | 9/2004 | Huang et al. | |
| 2004/0180386 A1 | 9/2004 | Carr et al. | |
| 2004/0235840 A1 | 11/2004 | Chari et al. | |
| 2005/0025763 A1 | 2/2005 | Williams et al. | |

(Continued)

FOREIGN PATENT DOCUMENTS

| | | |
|---|---|---|
| CN | 101139613 A | 3/2008 |
| CN | 101440130 A | 5/2009 |

(Continued)

OTHER PUBLICATIONS

Kalli et al. (Gynecological Oncology, 2008, 108:619-626).*
Kalli et al. Folate receptor alpha as a tumor target in epithelial ovarian cancer, Gynecologic Oncology, 2008, 108:619-626.*
Armstrong, D.K., et al., "Efficacy and safety of farletuzumab, a humanized monoclonal antibody to folate receptor alpha, in platinum-sensitive relapsed ovarian cancer subjects: preliminary data from a phase-2 study," *Eur. J. Cancer Suppl.* 7:450, Elsevier Science Ltd., England (2009).

(Continued)

*Primary Examiner* — Hong Sang
(74) *Attorney, Agent, or Firm* — Sterne, Kessler, Goldstein & Fox P.L.L.C.

(57) ABSTRACT

Methods to improve the success of cancer therapies that target the human folate receptor 1 are provided. Kits comprising reagent useful in the methods are further provided.

28 Claims, 25 Drawing Sheets

Figure 1:
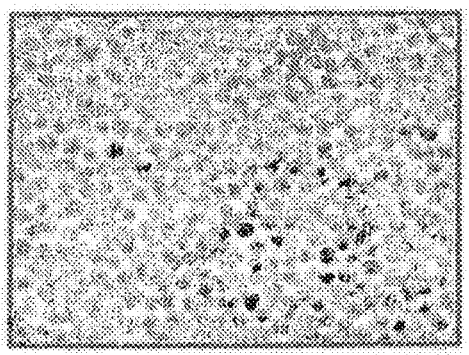
Figure 1:
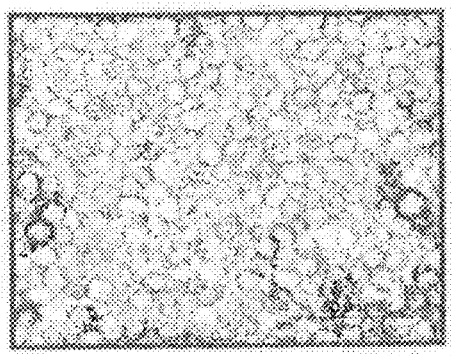

Specification includes a Sequence Listing.

(56) References Cited

U.S. PATENT DOCUMENTS

| | | |
|---|---|---|
| 2005/0244901 A1 | 11/2005 | Peschen et al. |
| 2005/0287538 A1 | 12/2005 | Cheung et al. |
| 2006/0030524 A1 | 2/2006 | Cohen et al. |
| 2006/0110771 A1 | 5/2006 | Katagiri et al. |
| 2006/0228349 A1 | 10/2006 | Acton et al. |
| 2006/0239910 A1 | 10/2006 | Nicolaides et al. |
| 2007/0041985 A1 | 2/2007 | Unger et al. |
| 2007/0098719 A1 | 5/2007 | Smith et al. |
| 2007/0099251 A1 | 5/2007 | Zhang et al. |
| 2007/0231266 A1 | 10/2007 | Low et al. |
| 2007/0294782 A1 | 12/2007 | Abad et al. |
| 2008/0081047 A1 | 4/2008 | Berry et al. |
| 2008/0104734 A1 | 5/2008 | Kav et al. |
| 2008/0138396 A1 | 6/2008 | Low et al. |
| 2008/0181888 A1 | 7/2008 | Ambrose et al. |
| 2008/0227704 A1 | 9/2008 | Kamens |
| 2008/0260748 A1 | 10/2008 | Iwamoto et al. |
| 2009/0081710 A1 | 3/2009 | Low et al. |
| 2009/0104215 A1 | 4/2009 | Ekiel et al. |
| 2009/0136516 A1 | 5/2009 | Tedder et al. |
| 2009/0169547 A1 | 7/2009 | Sahin et al. |
| 2009/0186027 A1 | 7/2009 | Solomon et al. |
| 2009/0214636 A1 | 8/2009 | Low et al. |
| 2009/0215165 A1 | 8/2009 | Rance et al. |
| 2009/0232822 A1 | 9/2009 | Joseloff et al. |
| 2009/0274697 A1 | 11/2009 | Grasso et al. |
| 2009/0274713 A1 | 11/2009 | Chari et al. |
| 2009/0280124 A1 | 11/2009 | Labat et al. |
| 2009/0280128 A1 | 11/2009 | Kamogawa et al. |
| 2009/0285795 A1 | 11/2009 | Patell |
| 2009/0285813 A1 | 11/2009 | Frey et al. |
| 2009/0317921 A1 | 12/2009 | Groome et al. |
| 2009/0324491 A1 | 12/2009 | Aburatani et al. |
| 2009/0324594 A1 | 12/2009 | Nicolaides et al. |
| 2010/0055034 A1 | 3/2010 | Martin et al. |
| 2010/0086537 A1 | 4/2010 | Sooknanan et al. |
| 2010/0087509 A1 | 4/2010 | Van Rompaey et al. |
| 2010/0092470 A1 | 4/2010 | Bhatt et al. |
| 2010/0104626 A1 | 4/2010 | Leamon et al. |
| 2010/0111852 A1 | 5/2010 | Yoshida |
| 2010/0111866 A1 | 5/2010 | Kratz |
| 2010/0129314 A1 | 5/2010 | Singh et al. |
| 2010/0239581 A1 | 9/2010 | Joseloff et al. |
| 2010/0255479 A1 | 10/2010 | Mikolajczyk et al. |
| 2010/0272741 A1 | 10/2010 | Knutson et al. |
| 2010/0323973 A1 | 12/2010 | Leamon et al. |
| 2010/0330572 A1 | 12/2010 | Assaraf et al. |
| 2011/0059469 A1 | 3/2011 | Aburatani et al. |
| 2011/0195022 A1 | 8/2011 | Deckert et al. |
| 2012/0009181 A1 | 1/2012 | Ab et al. |
| 2012/0177664 A1 | 7/2012 | Yokoseki et al. |
| 2012/0183552 A1 | 7/2012 | Joseloff et al. |
| 2012/0207771 A1 | 8/2012 | O'Shannessy et al. |
| 2012/0253021 A1 | 10/2012 | Li et al. |
| 2012/0259100 A1 | 10/2012 | Jin |
| 2012/0282282 A1 | 11/2012 | Lutz et al. |
| 2013/0295119 A1 | 11/2013 | Ab et al. |
| 2014/0023665 A1 | 1/2014 | Fishkin |
| 2014/0099332 A1 | 4/2014 | Testa et al. |
| 2014/0363451 A1 | 12/2014 | Running et al. |
| 2014/0363453 A1 | 12/2014 | Carrigan et al. |
| 2015/0093388 A1 | 4/2015 | Ab et al. |
| 2015/0132323 A1 | 5/2015 | Lutz et al. |
| 2015/0297744 A1 | 10/2015 | Lutz et al. |
| 2015/0306242 A1 | 10/2015 | Li et al. |
| 2016/0060339 A1 | 3/2016 | Ab et al. |
| 2016/0075781 A1 | 3/2016 | Ab et al. |
| 2016/0083471 A1 | 3/2016 | Ab et al. |
| 2016/0096887 A1 | 4/2016 | Ab et al. |
| 2016/0096888 A1 | 4/2016 | Ab et al. |
| 2016/0146824 A1 | 5/2016 | Carrigan et al. |
| 2017/0095571 A1 | 4/2017 | Ponte et al. |
| 2017/0168057 A1 | 6/2017 | Krizman et al. |
| 2017/0239367 A1 | 8/2017 | Running et al. |
| 2017/0306041 A1 | 10/2017 | Ab et al. |
| 2017/0327575 A1 | 11/2017 | Ab et al. |
| 2018/0003715 A1 | 1/2018 | Carrigan et al. |
| 2018/0333503 A1 | 11/2018 | Ruiz Soto et al. |
| 2019/0167704 A1 | 6/2019 | Ponte et al. |
| 2019/0365917 A1 | 12/2019 | Payne et al. |
| 2020/0046634 A1 | 2/2020 | Running et al. |
| 2020/0325240 A1 | 10/2020 | Ab et al. |
| 2020/0397806 A1 | 12/2020 | Ponte et al. |

FOREIGN PATENT DOCUMENTS

| | | |
|---|---|---|
| EP | 1 900 752 A1 | 3/2008 |
| EP | 1 864 133 B1 | 3/2010 |
| JP | 2010535710 A | 11/2010 |
| RU | 2610663 C2 | 2/2017 |
| WO | WO 94/29351 A2 | 12/1994 |
| WO | WO 97/11971 A1 | 4/1997 |
| WO | WO 02/071928 A2 | 9/2002 |
| WO | WO 2004/110498 A1 | 12/2004 |
| WO | WO 2005/003154 A2 | 1/2005 |
| WO | WO 2005/080431 A2 | 9/2005 |
| WO | WO 2006/105141 A1 | 10/2006 |
| WO | WO 2006/116592 A2 | 11/2006 |
| WO | WO 2007/006041 A2 | 1/2007 |
| WO | WO 2007/094754 A2 | 8/2007 |
| WO | WO 2007/147265 A1 | 12/2007 |
| WO | WO 2008/021290 A2 | 2/2008 |
| WO | WO 2008/031577 A1 | 3/2008 |
| WO | WO 2008/072723 A1 | 6/2008 |
| WO | WO 2008/101231 A2 | 8/2008 |
| WO | WO 2008/145136 A1 | 12/2008 |
| WO | WO 2009/080759 A1 | 7/2009 |
| WO | WO 2009/087978 A1 | 7/2009 |
| WO | WO 2009/132081 A2 | 10/2009 |
| WO | WO 2010/033733 A1 | 3/2010 |
| WO | WO-2010058572 A1 | 5/2010 |
| WO | WO 2010/111388 A2 | 9/2010 |
| WO | WO-2011032296 A1 | 3/2011 |
| WO | WO 2011/106528 | 9/2011 |
| WO | WO 2011/106528 A1 | 9/2011 |
| WO | WO 2012/061759 A2 | 2/2012 |
| WO | WO 2012/135675 A2 | 10/2012 |
| WO | WO 2012/138749 A1 | 10/2012 |
| WO | WO 2013/012722 A1 | 1/2013 |
| WO | WO 2014/186403 A2 | 11/2014 |

OTHER PUBLICATIONS

Armstrong, D.K., et al., "Exploratory phase II efficacy study of MORAb-003, a monoclonal antibody against folate receptor alpha, in platinum-sensitive ovarian cancer in first relapse," *J. Clin. Oncol. Suppl.* 26:293s, Abstract 8000, American Society of Clinical Oncology, United States (2008).

Bendig, M.M., "Humanization of Rodent Monoclonal Antibodies by CDR Grafting," *Methods: A Companion to Methods in Enzymology* 8:83-93, Academic Press, Inc., United States (1995).

Cagle, P.T., et al., "Folate Receptor in Adenocarcinoma and Squamous Cell Carcinoma of the Lung: Potential Target for Folate-Linked Therapeutic Agents," *Arch Pathol Lab Med Epub*: 1-4, College of American Pathologists, United States (2012).

Colman, P.M., "Effects of amino acid sequence changes on antibody-antigen interactions," *Research in Immunology* 145:33-36, Elsevier, France (1994).

Colnaghi, M.I., "Generation of Monoclonal Antibodies for In Vivo Approaches," *Nucl. Med. Biol.* 18(1):15-18, Pergamon Press plc, England (1991).

Conde, F.P., et al., "The Aspergillus toxin restrictocin is a suitable cytotoxic agent for generation of immunoconjugates with monoclonal antibodies directed against human carcinoma cells," *Eur. J. Biochem.* 178:795-802, Federation of European Biochemical Societies, England (1989).

Coney, L.R., et al., "Chimeric Murine-Human Antibodies Directed against Folate Binding Receptor Are Efficient Mediators of Ovarian Carcinoma Cell Killing," *Cancer Res.* 54:2448-2455, American Association for Cancer Research, United States (1994).

(56) References Cited

OTHER PUBLICATIONS

Coney, L.R., et al., "Cloning of a Tumor-associated Antigen: MOv18 and MOv19 Antibodies Recognize a Folate-binding Protein," *Cancer Res. 51*:6125-6132, American Association for Cancer Research, United States (1991).
Copeland, A., et al.,"B1G510 (B1G510_9BURK) Unreviewed, UniProtKB/TrEMBL," UniProt, 3 pages, last modified Dec. 14, 2011, accessed at <http://www.uniprot.org/uniprot/B1G510>.
Ebel, W., et al., "Preclinical evaluation of MORAb-003, a humanized monoclonal antibody antagonizing folate receptor-alpha," *Cancer Immun. 7*:6-13, Luigi Grasso, United States (2007).
Ferrini, S., et al., "Bispecific Monoclonal Antibodies Directed to CD16 and to a Tumor-Associated Antigen Induce Target-Cell Lysis by Resting NK Cells and by a Subset of NK Clones," *Int. J. Cancer 48*:227-233, Wiley-Liss, Inc., United States (1991).
Ferrini, S., et al., "Retargeting of T-Cell-Receptor Gamma/Delta$^+$ Lymphocytes Against Tumor Cells by Bispecific Monoclonal Antibodies. Induction of Cytolytic Activity and Lymphokine Production," *Int. J Cancer Supplement 4*:53-55, Alan R. Liss, Inc., United States (1989).
Figini, M., et al., "Panning Phage Antibody Libraries on Cells: Isolation of Human Fab Fragments against Ovarian Carcinoma Using Guided Selection," *Cancer Res. 58*:991-996, American Association for Cancer Research, United States (1998).
Franklin, W.A., et al., "New Anti-Lung-Cancer Antibody Cluster 12 Reacts With Human Folate Receptors Present on Adenocarcinoma," *Int. J. Cancer Supplement 8*: 89-95, Wiley-Liss, Inc., United States (1994).
Gould, H.J., et al., "Comparison of IgE and IgG antibody-dependent cytotoxicity in vitro and in a SCID mouse xenograft model of ovarian carcinoma," *Eur. J Immunol. 29*:3527-3537, Wiley-VCH Verlag GmbH, Germany (1999).
Hartmann, L.C., et al., "Folate receptor overexpression is associated with poor outcome in breast cancer," *Int. J. Cancer 121*:938-942, Wiley-Liss, Inc., United States (2007).
Jones, M.B., et al., "Rationale for folate receptor alpha targeted therapy in 'high risk' endometrial carcinomas," *Int. J. Cancer 123*:1699-1703, Wiley-Liss, Inc., United States (2008).
Karagiannis, S. N., et al., "IgE-Antibody-Dependent Immunotherapy of Solid Tumors: Cytotoxic and Phagocytic Mechanisms of Eradication of Ovarian Cancer Cells," *J. Immunol. 179*:2832-2843, American Association of Immunologists, United States (2007).
Lim, J., et al., "C5A929 (C5A929_BURGB) Unreviewed, UniProtKB/TrEMBL", UniProt, 4 pages, last modified Apr. 18, 2012, accessed at <http://www.uniprot.org/uniprot/C5A929>.
Melani, C., et al., "Targeting of Interleukin 2 to Human Ovarian Carcinoma by Fusion with a Single-Chain Fv of Antifolate Receptor Antibody," *Cancer Res. 58*:4146-4154, American Association for Cancer Research, United States (1998).
Mezzanzanica, D., et al., "Human Ovarian Carcinoma Lysis by Cytotoxic T Cells Targeted by Bispecific Monoclonal Antibodies: Analysis of the Antibody Components," *Int. J. Cancer 41*:609-615, Alan R, Liss, Inc., United States (1988).
Miotti, S., et al., "Characterization of Human Ovarian Carcinoma-Associated Antigens Defined by Novel Monoclonal Antibodies With Tumor-Restricted Specificity," *Int. J. Cancer 39*:297-303, Alan R, Liss, Inc., United States (1987).
Nishiyama, T., et al., "A9SZW6 (A9SZW6_PHYPA) Unreviewed, UniProtKB/TrEMBL," UniProt, 3 pages, last modified Sep. 21, 2011, accessed at <http://www.uniprot.org/uniprot/A9SZW6>.
Paul, W.E., eds., "Structure and Function of Immunoglobulins," in *Fundamental Immunology, Third Edition*, pp. 292-295, Raven Press, New York, United States (1993).
Portolano, S., et al., "Lack of Promiscuity in Autoantigen-Specific H and L Chain Combinations as Revealed by Human H and L Chain 'Roulette'," *The Journal of Immunology 150(3)*:880-887, The American Association of Immunologists, United States (1993).
Rudikoff, S., et al., "Single amino acid substitution altering antigen-binding specificity," *Proc. Natl. Acad. Sci. USA 79*:1979-1983, National Academy of Sciences, United States (1982).

Scorer, P., et al., "A Full Immunohistochemical Evaluation of a Novel Monoclonal Antibody to Folate Receptor-alpha (FR-α)," *reAGENTS 3*:8-12, Leica Biosystems Newcastle Ltd, United Kingdom (2010).
Smith, A.E., et al., "A Novel Monoclonal Antibody for Detection of Folate Receptor Alpha in Paraffin-Embedded Tissues," *HYBRIDOMA 26(5)*:281-288, Mary Ann Liebert, Inc., United States (2007).
Smith-Jones, P.M., et al., "Preclinical Radioimmunotargeting of Folate Receptor Alpha using the Monoclonal Antibody Conjugate DOTA-MORAb-003," *Nucl. Med. Biol. 35(3)*:343-351, Elsevier, United States (2008).
Widdison, W.C., et al., "Semisynthetic Maytansine Analogues for the Targeted Treatment of Cancer," *J. Med. Chem. 49*:4392-4408, American Chemical Society, United States (2006).
Zacchetti, A., et al., "$^{177}$Lu-labeled MOv18 as compared to $^{131}$I- or $^{90}$Y-labeled MOv18 has the better therapeutic effect in eradication of alpha folate receptor-expressing tumor xenografts," *Nucl. Med. Biol. 36*:759-770, Elsevier Inc., United States (2009).
English language Abstract of Chinese Patent Publication No. CN 101139613A European Patent Office, espacenet database—Worldwide, (2012) (listed as document FP10 on the accompanying form PTO/SB/08A).
English language Abstract of Chinese Patent Publication No. CN 101440130A, European Patent Office, espacenet database—Worldwide, (2012) (listed as document FP13 on the accompanying form PTO/SB/08A).
International Search Report for International Application No. PCT/US2011/026079, International Searching Authority, United States, dated Aug. 2, 2011.
International Search Report for International Application No. PCT/US2012/032155, International Searching Authority, United States, dated Jul. 6, 2012.
International Search Report for International Application No. PCT/US2012/031544, International Searching Authority, United States, dated Sep. 21, 2012.
Ab, O., et al., "Antibody-Maytansinoid Conjugates Targeting Folate Receptor 1 for Cancer Therapy," *2010 EORTC-NCI-AACR Symposium—Berlin, Germany* (Nov. 16-19, 2010), Abstract 236, 1 Page, American Association for Cancer Research, Germany (distributed in print Nov. 16, 2010; available online Oct. 29, 2010).
Ab, O., et al., "IMGN853, an anti-Folate Receptor I antibody-maytansinoid conjugate for targeted cancer therapy," *102nd Annual AACR Meeting—Orlando, FL* (Apr. 2-6, 2011), Abstract 4576, 1 Page, American Association for Cancer Research, United States (distributed on print Mar. 8, 2011; available online Feb. 25, 2011).
Ab, O., et al., "IMGN853, an anti-Folate Receptor I antibody-maytansinoid conjugate for targeted cancer therapy," *102nd Annual AACR Meeting—Orlando, FL* (Apr. 2-6, 2011), Abstract 4576 Poster, American Association for Cancer Research, United States (Apr. 2, 2011).
Carrigan, C.N., et al., "Evaluation of Folate Receptor 1 (FOLR1) expression by calibrated immunohistochemistry identifies candidate tumor subtypes for targeting by IMGN853, an anti-FOLR1-maytansinoid conjugate," *102nd Annual AACR Meeting—Orlando, FL* (Apr. 2-6, 2011), Abstract 3617, 1 Page, American Association for Cancer Research, United States (distributed in print Mar. 8, 2011; available online Feb. 25, 2011).
Carrigan, C.N., et al., "Evaluation Of Folate Receptor 1 (FOLR1) Expression by Calibrated Immunohistochemistry Identifies Candidate Tumor Subtypes for Targeting by IMGN853, an Anti-FOLR1-Maytansinoid Conjugate," *102nd Annual AACR Meeting—Orlando, FL* (Apr. 2-6, 2011), Abstract 3617 Poster, American Association for Cancer Research, United States (Apr. 2, 2011).
Chen, J., et al., "Antibody-cytotoxic agent conjugates for cancer therapy," *Expert Opin. Drug Deliv. 2(5)*:873-890, Ashley Publications, England (2005).
O'Shannessy, D.J., et al., "Characterization of the Human Folate Receptor Alpha Via Novel Antibody-Based Probes," *Oncotarget 2(12)*:1227-1243, Impact Journals, United States (Dec. 27, 2011).
Ladd, S., et al., "Folate Receptor 1 Immunohistochemistry Repeatability and Stored Slide Antigen Stability," *38$^{th}$ Annual NSH Symposium—Vancouver, BC Canada* (Sep. 28-Oct. 3, 2012), Abstract, 1 page, National Society for Histotechnology, Canada (2012).

(56) References Cited

OTHER PUBLICATIONS

Ladd, S., et al., "Folate Receptor 1 Immunohistochemistry; Repeatability and Stored Slide Antigen Stability," *38th Annual NSH Symposium—Vancouver, BC Canada* (Sep. 28-Oct. 3, 2012), Poster P-38, National Society for Histotechnology, Canada (Sep. 28, 2012).

Singh, R. and Erickson, H.K., "Antibody-Cytotoxic Agent Conjugates: Preparation and Characterization," in *Therapeutics Antibodies: Methods and Protocols* vol. 525, Dimitrov, A.S., ed., pp. 445-467, Humana Press, United States (2009).

Van Dam, G.M., et al., "Intraoperative tumor-specific fluorescence imaging in ovarian cancer by folate receptor-α targeting: first in-human results," *Nature Medicine 17(10)*:1315-1320, Nature America, Inc., United States (Sep. 18, 2011).

Whiteman, K.R., et al., "Preclinical evaluation of IMGN853, an anti-FOLR1 antibody-maytansinoid conjugate, as a potential therapeutic for ovarian cancer," *102nd Annual AACR Meeting—Orlando, FL* (Apr. 2-6, 2011), Abstract 1760, 1 Page, American Association for Cancer Research, United States (distributed in print Mar. 8, 2011; available online Feb. 25, 2011).

Whiteman, K.R., et al., "Preclinical evaluation of IMGN853, an anti-FOLR1 antibody-maytansinoid conjugate, as a potential therapeutic for ovarian cancer," *102nd Annual AACR Meeting—Orlando, FL* (Apr. 2-6, 2011), Abstract 1760 Poster, American Association for Cancer Research, United States (Apr. 2, 2011).

Whiteman, K.R., et al., "Anti-tumor activity and pharmacokinetics of the anti-FOLR-1-maytansinoid conjugate IMGN853 is maintained over a wide range of maytansinoid-to-antibody ratios," *103rd Annual AACR Meeting—Chicago, IL* (Mar. 31-Apr. 4, 2012), Abstract #4628, 1 page, American Association for Cancer Research, United States (2012).

Whiteman, K.R., et al., "Anti-tumor activity and pharmacokinetics of the anti-FOLR-1-maytansinoid conjugate IMGN853 is maintained over a wide range of maytansinoid-to-antibody ratios," *103nd Annual AACR Meeting—Chicago, IL* (Mar. 31-Apr. 4, 2012), Abstract #4628 Poster, American Association for Cancer Research, United States (Mar. 31, 2012).

Yuan, Y., et al., "Expression of the folate receptor genes FOLR1 and FOLR3 differentiates ovarian carcinoma from breast carcinoma and malignant mesothelioma in serious effusions," *Human Pathology 40*:1453-1460, Elsevier Inc., United States (2009).

Supplementary European Search Report for European Application No. EP 11748067.3, The Hague, Netherlands, dated Jun. 26, 2013.

Notice of Allowance, dated Aug. 8, 2013, in U.S. Appl. No. 13/033,723, filed Feb. 24, 2011.

International Preliminary Report on Patentability, dated Oct. 10, 2013, in International application No. PCT/US2012/031544, filed Mar. 30, 2012.

International Preliminary Report on Patentability, dated Oct. 17, 2013, in International application No. PCT/US2012/032155, filed Apr. 4, 2012.

Non-Final Office Action, dated Oct. 11, 2013, in U.S. Appl. No. 13/439,493, filed Apr. 4, 2012.

International Search Report in International Application No. PCT/US2013/057682, International Searching Authority, United States, Alexandria, VA, dated Jan. 10, 2014.

Allard, J.E., et al., "Overexpression of folate binding protein is associated with shortened progression-free survival in uterine adenocarcinomas," *Gynecologic Oncology 107(1)*:52-57, Academic Press, United States (2007).

Bueno, R., et al., "The α Folate Receptor is Highly Activated in Malignant Pleural Mesothelioma," *The Journal of Thoracic and Cardiovascular Surgery 121(2)*:225-233, Mosby, United States (2001).

Chen, Y., et al., "Drug delivery across the blood-brain barrier," *Current Drug Delivery 1(4)*:361-376, Bentham Science Publishers, United Arab Emirates (2004).

Farrell, C., et al., "Population pharmacokinetics of farletuzumab, a humanized monoclonal antibody against folate receptor alpha, in epithelial ovarian cancer," *Cancer Chemotherapy and Pharmacology 70(5)*:727-734, Springer Verlag, Germany (Nov. 2012, Epub: Sep. 7, 2012).

Figini, M., et al., "Conversion of murine antibodies to human antibodies and their optimization for ovarian cancer therapy targeted to the folate receptor," *Cancer Immunology and Immunotherapy 58(4)*:531-546, Springer Verlag, Germany (2009).

Kalli, R.K., et al., "Folate receptor alpha as a tumor target in epithelial ovarian cancer," *Gynecologic Oncology 108(3)*:619-626, Academic Press, United States (2008).

Lawson, N. and Scorer, P., "Evaluation of Antibody to Folate Receptor alpha (FR-a)," published online on May 31, 2010, accessed at www.leicabiosystems.com/pathologyleaders/evaluation-of-antibody-to-folate-receptor-alpha-fr-%CE%B1/, accessed on Oct. 27, 2014 (1 page).

Nutt, J.E., et al., "The role of folate receptor alpha (FRα) in the response of malignant pleural mesothelioma to pemetrexed-containing chemotherapy," *British Journal of Cancer 102(3)*:553-560, Nature Publishing Group, England (2010).

Office Action dated Dec. 24, 2014, in U.S. Appl. No. 14/015,653, Testa, N.E., et al., filed Aug. 30, 2013.

Office Action dated Dec. 31, 2014, in U.S. Appl. No. 13/800,835, Ab, O., et al., filed Mar. 13, 2013.

International Search Report for International Application No. PCT/US2014/037911, International Searching Authority, United States, dated Oct. 31, 2014.

Supplementary Partial European Search Report for EP Application No. EP 12 76 4885, The Hague, Netherlands, dated Nov. 21, 2014.

Search Report and Written Opinion for SG Patent Application No. 20130770040, Intellectual Property Office of Singapore, Singapore, dated Dec. 30, 2014.

Mantovani, L.T., et al., "Folate Binding Protein Distribution in Normal Tissues and Biological Fluids From Ovarian Carcinoma Patients as Detected by the Monoclonal Antibodies MOv18 and MOv19," *European Journal of Cancer 30A(3)*:363-369, Pergamon Press, England(1994).

Chittenden, T., "Discovery and Preclinical Evaluation of Antibody-Maytansinoid Conjugates," *4th World Antibody-Drug Conjugate Summit*, Frankfurt, Germany, 36 pages (Feb. 29-Mar. 1, 2012).

Chen, Y., et al., "Drug Delivery Across the Blood-Brain Barrier," *Current Drug Delivery 1(4)*: 361-376, Bentham Science Publishers Ltd, United Arab Emirates (2004).

Office Action dated Jun. 3, 2015, in U.S. Appl. No. 14/015,653, Inventors: Carrigan, C., et al., filed Aug. 30, 2013.

Issue Notification, dated Nov. 11, 2015, in U.S. Appl. No. 14/015,653, Inventors: Carrigan, C., et al., filed Aug. 30, 2013.

Office Action dated Aug. 6, 2015, in U.S. Appl. No. 14/276,917, Inventors: Running, K., et al., filed May 13, 2014.

Office Action dated Aug. 27, 2015, in U.S. Appl. No. 14/509,809, Inventors: Lutz, R., et al., filed Oct. 8, 2014.

Office Action dated Dec. 9, 2015, in U.S. Appl. No. 14/509,809, Inventors Lutz, R.J., et al., filed Oct. 8, 2014.

Office Action dated Dec. 22, 2015, in U.S. Appl. No. 14/473,828, Inventors Ab., O., et al., filed Aug. 29, 2014.

Office Action dated Nov. 9, 2015, in U.S. Appl. No. 14/671,765, Inventors Lutz, R.J., et al., filed Mar. 27, 2015.

Office Action dated Jan. 21, 2016, in U.S. Appl. No. 14/970,433, Inventors: Ab, Olga et al., filed Dec. 15, 2015.

Brown, M., et al., "Tolerance to Single, but Not Multiple, Amino Acid Replacements in Antibody $V_H$ CDR2," *The Journal of Immunology 156*:3285-3291, The American Association of Immunologists, United States (1996).

Gershoni, J.M., et al., "Epitope Mapping The First Step in Developing Epitope-Based Vaccines," *Biodrugs 21(3)*:145-156, Adis Data Information BV, Israel (2007).

Supplementary Partial European Search Report for EP Application No. 13 83 3526, The Hague, The Netherlands, dated Mar. 8, 2016.

Winkler, K., et al., "Changing the Antigen Binding Specificity by Single Point Mutations of an Anti-p24 (HIV-1) Antibody," *Journal of Immunology 165*:4505-4514, American Association of Immunologists, United States (2000).

Office Action, dated Apr. 28, 2016, in U.S. Appl. No. 14/819,209, filed Aug. 5, 2015.

(56) References Cited

OTHER PUBLICATIONS

Office Action, dated Mar. 24, 2016, in U.S. Appl. No. 14/276,917, filed May 13, 2014.
Office Action, dated Mar. 18, 2016, in U.S. Appl. No. 14/509,809, filed Oct. 8, 2014.
Office Action, dated Mar. 31, 2016, in U.S. Appl. No. 14/473,828, filed Aug. 29, 2014.
Office Action, dated Apr. 19, 2016, in U.S. Appl. No. 14/921,596, filed Oct. 23, 2015.
Final Office Action, dated Sep. 23, 2016, in U.S. Appl. No. 14/819,209, Ab, O., et al., filed Aug. 5, 2015.
Lu, Y. and Low, P.S., "Immunotherapy of folate receptor-expressing tumors: review of recent advances and future prospects," *Journal of Controlled Release 91*:17-29, Elsevier B.V., Netherlands (2003).
NCL-L-FRalpha, "Novocastra™ Liquid Mouse Monoclonal Antibody Folate Receptor Alpha: Product Code: NCL-L-FRalpha," 40 Pages, Leica Biosystems Newcastle Ltd, England (2009).
Pagnelli, G., et al., "Two-step tumour targeting in ovarian cancer patients using biotinylated monoclonal antibodies and radioactive streptavidin," *Eur J Nucl Med 19*:322-329, Springer-Verlag, Germany (1992).
Non-Final Office Action, dated Aug. 3, 2016, in U.S. Appl. No. 14/509,809, Lutz, R., et al., filed Oct. 8, 2014.
Non-Final Office Action, mailed Aug. 25, 2016, in U.S. Appl. No. 14/276,917, Running, K., et al., filed May 13, 2014.
Notice of Abandonment, dated May 17, 2016, in U.S. Appl. No. 14/671,765, Lutz, R., et al., filed Mar. 27, 2015.
Non-final Office Action dated Dec. 8, 2016 in U.S. Appl. No. 14/952,659, filed Nov. 25, 2015.
Notice of Allowance dated Dec. 7, 2016 in U.S. Appl. No. 14/970,433, filed Dec. 15, 2015.
Non-final Office Action dated Dec. 5, 2016 in U.S. Appl. No. 14/970,436, filed Dec. 15, 2015.
Final Office Action dated Oct. 26, 2016 in U.S. Appl. No. 14/921,596, filed Oct. 23, 2015.
Non-Final Office Action dated Oct. 7, 2016 in U.S. Appl. No. 14/473,828, filed Aug. 29, 2014.
Non-final Office Action dated Nov. 3, 2016 in U.S. Appl. No. 14/946,423 filed Nov. 19, 2015.
Advisory Action dated Feb. 3, 2017 in U.S. Appl. No. 14/921,596 , filed Oct. 23, 2015.
Casalini, P., et al., "Use of Combination of Monoclonal Antibodies Directed Against Three Distinct Epitopes Of A Tumor-Associated Antigen: Analysis of Cell Binding and Internalization," *International Journal of Cancer 48*:284-290, Wiley-Liss, Inc., United States (1991).
Final Office Action dated May 8, 2017 in U.S. Appl. No. 14/509,809, filed Oct. 8, 2014.
Notice of Abandonment dated Mar. 23, 2017 in U.S. Appl. No. 14/276,917, filed May 13, 2014.
Notice of Panel Decision from Pre-Appeal Brief Review dated Feb. 8, 2017 in U.S. Appl. No. 14/509,809, filed Oct. 8, 2014.
Brand, F., et al., "Prospect for Anti-HER2 Receptor Therapy in Breast Cancer," *Anticancer Research 26*:463-70, Stanford University HighWire Press, United States (2006).
Moore, K., et al., "IMGN853 (mirvetuximab soravtansine), a folate receptor alpha (FRα)-targeting antibody-drug conjugate (ADC): single agent activity in platinum-resistant epithelial ovarian cancer (EOC) patients ," *2016 ASCO Annual Meeting* (Jun. 3-7, 2016), Abstract 5567 Poster, American Society of Clinical Oncology (Jun. 6, 2016).
Non-Final Office Action dated Oct. 30, 2017 in U.S. Appl. No. 15/473,008, filed Mar. 29, 2017.
Notice of Allowance dated Mar. 8, 2018 in U.S. Appl. No. 15/473,008, filed Mar. 29, 2017.
Examiner's Answer to Appeal Brief, dated Jan. 25, 2018, in U.S. Appl. No. 14/509,809 , filed Oct. 8, 2014.
Non-Final Office Action, dated Mar. 12, 2018, in U.S. Appl. No. 15/268,298 , filed Sep. 16, 2016.
Moore, K.N., et al., "Forward I (GOG 3011): A Phase III study of mirvetuximab soravtansine, a folate receptor alpha (FRa)-targeting antibody-drug conjugate, versus chemotherapy in patients with platinum-resistant ovarian cancer," Presented at Barcelona ESMO Congress, Sep. 2019, 15 pages.
Office Action dated Mar. 21, 2012, in U.S. Appl. No. 12/441,207, inventor Martin; Franck, filed May 13, 2009, 11 pages.
Office Action dated Jul. 1, 2011, in U.S. Appl. No. 12/441,207, inventor Martin; Franck, filed May 13, 2009, 25 pages.
Spannuth; W.A. et al. "Farletuzumab in epithelial ovarian carcinoma," *Expert Opin Biol Ther 10*(3):431-7, Taylor & Francis Group, England (2010).
De Miranda, B.N.M., "Clonagem, expressao e purificacao de alfa receptors de folato de Homo sapiens para aplicacoes bioanaliticas em cancer," Masters Dissertation, Aug. 22, 2014, University of São Paulo (USP). Institute of Chemistry of São Carlos, 93 pages.
English language abstract to De Miranda B.N.M., "Clonagem, expressao e purificacao de alfa receptors de folato de Homo sapiens para aplicacoes bioanaliticas em cancer," Masters Dissertation, Aug. 22, 2014, University of São Paulo (USP). Institute of Chemistry of São Carlos, 2 pages.
Santacana, M., et al., "A 9-protein biomarker molecular signature for predicting histologic type in endometrial carcinoma by immunohistochemistry," *Human Pathology 45*(12):2394-2403, W.B. Saunders Ltd., United Kingdom (Dec. 2014).
Office Action dated Nov. 8, 2012, in U.S. Appl. No. 13/033,723, Ab, O., et al., filed Feb. 24, 2011, 21 pages.
Final Office Action dated May 1, 2013, in U.S. Appl. No. 13/033,723, Ab, O., et al., filed Feb. 24, 2011, 13 pages.
Office Action dated Jun. 24, 2019, in U.S. Appl. No. 15/906,416, Widdison, W. C., et al., filed Feb. 27, 2018, 6 pages.
Final Office Action dated Jan. 10, 2020, in U.S. Appl. No. 15/906,416, Widdison, W. C., et al., filed Feb. 27, 2018, 4 pages.
Office Action dated Feb. 7, 2020, in U.S. Appl. No. 15/979,989, Ruiz Soto, R. R., et al., filed May 15, 2018, 45 pages.
Office Action dated Jul. 30, 2020, in U.S. Appl. No. 15/979,989, Ruiz Soto, R. R., et al., filed May 15, 2018, 56 pages.
Final Office Action dated Feb. 22, 2021, in U.S. Appl. No. 15/979,989, Ruiz Soto, R. R., et al., filed May 15, 2018, 52 pages.
Office Action dated Jun. 2, 2020, in U.S. Appl. No. 16/185,960, Ponte, J., et al., filed Nov. 9, 2018, 58 pages.
Final Office Action dated Sep. 22, 2020, in U.S. Appl. No. 16/185,960, Ponte, J., et al., filed Nov. 9, 2018, 61 pages.
Co-pending Application, U.S. Appl. No. 17/150,379, inventors Lutz, R. J., et al., filed Jan. 15, 2021 (Not Yet Published).

\* cited by examiner

A. 300-19 cells

B. 300-19 cells transfected with FOLR1

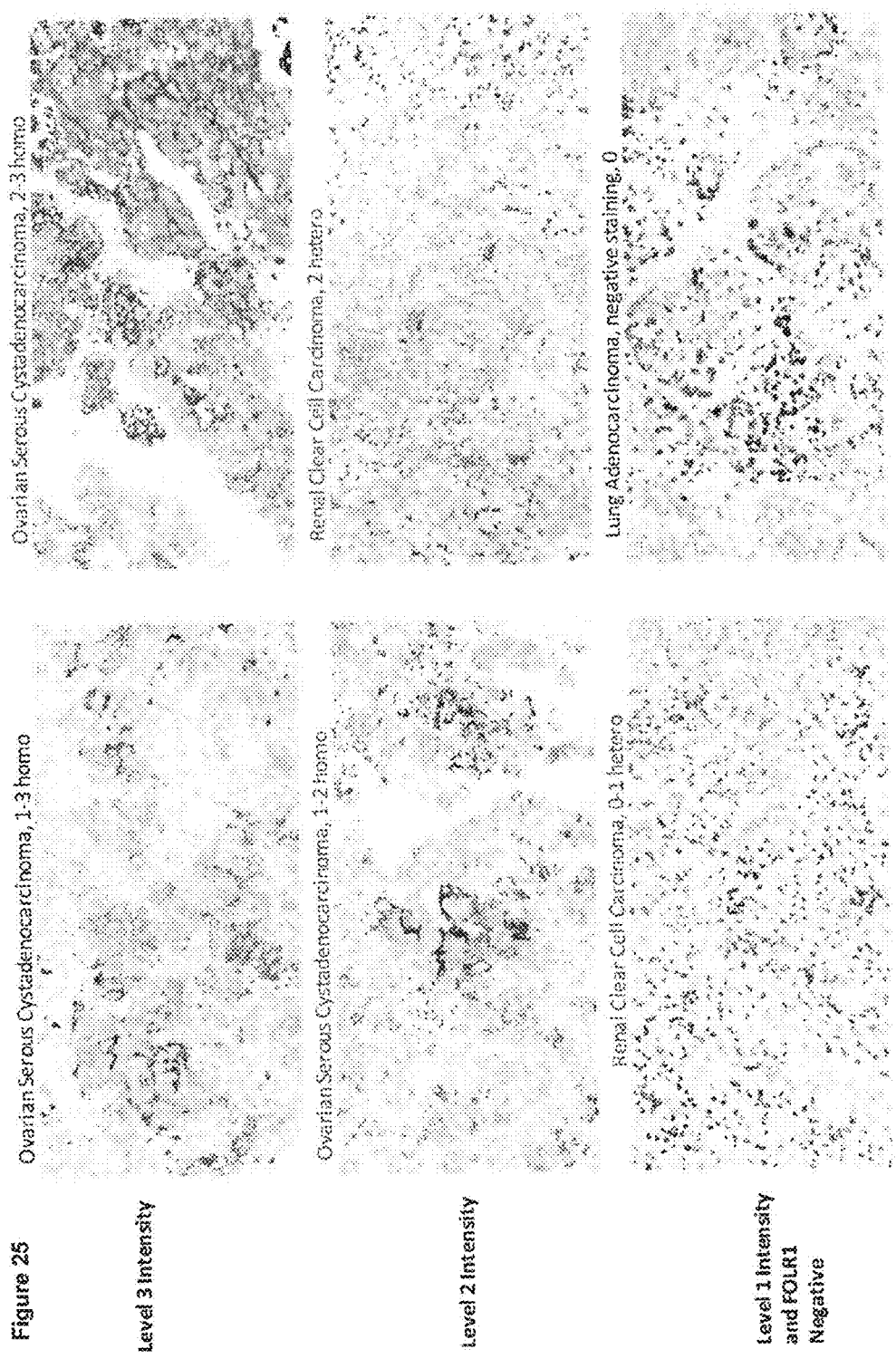

SEQUENCE LISTING

```
<160> NUMBER OF SEQ ID NOS: 11

<210> SEQ ID NO 1
<211> LENGTH: 257
<212> TYPE: PRT
<213> ORGANISM: Homo sapiens

<400> SEQUENCE: 1

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Arg Lys Asn Ala
        50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
```

```
            85                  90                  95
Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser
```

<210> SEQ ID NO 2
<211> LENGTH: 771
<212> TYPE: DNA
<213> ORGANISM: Homo sapiens

<400> SEQUENCE: 2

```
atggctcagc ggatgacaac acagctgctg ctccttctag tgtgggtggc tgtagtaggg      60
gaggctcaga caaggattgc atgggccagg actgagcttc tcaatgtctg catgaacgcc     120
aagcaccaca aggaaaagcc aggccccgag acaagttgc atgagcagtg tcgaccctgg      180
aggaagaatg cctgctgttc taccaacacc agccaggaag cccataagga tgtttcctac     240
ctatatagat tcaactggaa ccactgtgga gagatggcac ctgcctgcaa acggcatttc     300
atccaggaca cctgcctcta cgagtgctcc cccaacttgg ggccctggat ccagcaggtg     360
gatcagagct ggcgcaaaga gcgggtactg aacgtgcccc tgtgcaaaga ggactgtgag     420
caatggtggg aagattgtcg cacctcctac acctgcaaga gcaactggca caagggctgg     480
aactggactt cagggtttaa caagtgcgca gtgggagctg cctgccaacc tttccatttc     540
tacttcccca cacccactgt tctgtgcaat gaaatctgga ctcactccta caaggtcagc     600
aactacagcc gagggagtgg ccgctgcatc cagatgtggt tcgacccagc ccagggcaac     660
cccaatgagg aggtggcgag gttctatgct gcagccatga gtggggctgg gccctgggca     720
gcctggcctt tcctgcttag cctggcccta atgctgctgt ggctgctcag c              771
```

<210> SEQ ID NO 3
<211> LENGTH: 118
<212> TYPE: PRT
<213> ORGANISM: Artificial Sequence
<220> FEATURE:
<223> OTHER INFORMATION: huMov19 vHC

<400> SEQUENCE: 3

Gln Val Gln Leu Val Gln Ser Gly Ala Glu Val Val Lys Pro Gly Ala

-continued

```
                1               5                  10                  15
Ser Val Lys Ile Ser Cys Lys Ala Ser Gly Tyr Thr Phe Thr Gly Tyr
                    20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

<210> SEQ ID NO 4
<211> LENGTH: 112
<212> TYPE: PRT
<213> ORGANISM: Artificial Sequence
<220> FEATURE:
<223> OTHER INFORMATION: huMov19 vLCv1.00

<400> SEQUENCE: 4

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110
```

<210> SEQ ID NO 5
<211> LENGTH: 112
<212> TYPE: PRT
<213> ORGANISM: Artificial Sequence
<220> FEATURE:
<223> OTHER INFORMATION: huMov19 vLCv1.60

<400> SEQUENCE: 5

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80
```

```
Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 6
<211> LENGTH: 5
<212> TYPE: PRT
<213> ORGANISM: Artificial sequence
<220> FEATURE:
<223> OTHER INFORMATION: huMov19 vHC CDR1

<400> SEQUENCE: 6

Gly Tyr Phe Met Asn
1               5

<210> SEQ ID NO 7
<211> LENGTH: 17
<212> TYPE: PRT
<213> ORGANISM: Artificial sequence
<220> FEATURE:
<223> OTHER INFORMATION: Kabat Defined Mov19 HC CDR2 Human

<400> SEQUENCE: 7

Arg Ile His Pro Tyr Asp Gly Asp Thr Phe Tyr Asn Gln Lys Phe Gln
1               5                   10                  15

Gly

<210> SEQ ID NO 8
<211> LENGTH: 9
<212> TYPE: PRT
<213> ORGANISM: Artificial sequence
<220> FEATURE:
<223> OTHER INFORMATION: huMov19 vHC CDR3

<400> SEQUENCE: 8

Tyr Asp Gly Ser Arg Ala Met Asp Tyr
1               5

<210> SEQ ID NO 9
<211> LENGTH: 15
<212> TYPE: PRT
<213> ORGANISM: Artificial sequence
<220> FEATURE:
<223> OTHER INFORMATION: huMov19 vLC CDR1

<400> SEQUENCE: 9

Lys Ala Ser Gln Ser Val Ser Phe Ala Gly Thr Ser Leu Met His
1               5                   10                  15

<210> SEQ ID NO 10
<211> LENGTH: 7
<212> TYPE: PRT
<213> ORGANISM: Artificial sequence
<220> FEATURE:
<223> OTHER INFORMATION: huMov19 vLC CDR2

<400> SEQUENCE: 10

Arg Ala Ser Asn Leu Glu Ala
1               5

<210> SEQ ID NO 11
<211> LENGTH: 9
<212> TYPE: PRT
<213> ORGANISM: Artificial sequence
<220> FEATURE:
```

```
<223> OTHER INFORMATION: huMov19 vLC CDR3

<400> SEQUENCE: 11

Gln Gln Ser Arg Glu Tyr Pro Tyr Thr
1               5
```

METHODS FOR INCREASING EFFICACY OF FOLR1 CANCER THERAPY

CROSS-REFERENCE TO RELATED APPLICATIONS

This application is a continuation of U.S. application Ser. No. 14/245,797, filed on Apr. 4, 2014, now abandoned, which is a continuation of U.S. application Ser. No. 13/435,857, filed on Mar. 30, 2012, now U.S. Pat. No. 8,709,432, which claims the benefit of U.S. Provisional Appl. No. 61/471,007, filed Apr. 1, 2011, all of which are herein incorporated by reference.

REFERENCE TO SEQUENCE LISTING SUBMITTED ELECTRONICALLY

The content of the electronically submitted sequence listing, file name: 2921_0150003_Substitute_Sequence_Listing.txt; size: 8,314 bytes; and date of creation: Mar. 14, 2018, filed herewith, is incorporated herein by reference in its entirety.

BACKGROUND OF THE INVENTION

Field of the Invention

The field of invention generally relates to increasing the efficacy of the treatment of cancers characterized by the overexpression of human folate receptor 1 (FOLR1). More specifically, the invention concerns more effective treatment of patients susceptible to or diagnosed with cancer, in which the tumor cells overexpress FOLR1 as determined by a gene expression assay, with a FOLR1 antagonist, e.g., a FOLR1 immunoconjugate.

Background Art

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, *Cancer J. Clin.* 53:5-26).

Folate Receptor 1 (FOLR1), also known as Folate Receptor-alpha, or Folate Binding Protein, is an N-glycosylated protein expressed on plasma membrane of cells. FOLR1 has a high affinity for folic acid and for several reduced folic acid derivatives. FOLR1 mediates delivery of the physiological folate, 5-methyltetrahydrofolate, to the interior of cells.

FOLR1 is overexpressed in vast majority of ovarian cancers, as well as in many uterine, endometrial, pancreatic, renal, lung, and breast cancers, while the expression of FOLR1 on normal tissues is restricted to the apical membrane of epithelial cells in the kidney proximal tubules, alveolar pneumocytes of the lung, bladder, testes, choroid plexus, and thyroid (Weitman S D, et al., *Cancer Res* 52: 3396-3401 (1992); Antony A C, *Annu Rev Nutr* 16: 501-521 (1996); Kalli K R, et al. *Gynecol Oncol* 108: 619-626 (2008)). This expression pattern of FOLR1 makes it a desirable target for FOLR1-directed cancer therapy.

Because ovarian cancer is typically asymptomatic until advanced stage, it is often diagnosed at a late stage and has poor prognosis when treated with currently available procedures, typically chemotherapeutic drugs after surgical de-bulking (von Gruenigen V et al., *Cancer* 112: 2221-2227 (2008); Ayhan A et al., *Am J Obstet Gynecol* 196: 81 e81-86 (2007); Harry V N et al., *Obstet Gynecol Surv* 64: 548-560 (2009)). Thus, there is a clear unmet medical need for more effective therapeutics for ovarian cancers.

SUMMARY OF THE INVENTION

The present invention is based on the discovery of a dynamic range of expression of FOLR1 in tumor tissue and the discovery that tumors with increased levels of FOLR1 expression are more responsive to treatment with anti-FOLR1 antibodies or anti-FOLR1 immunoconjugates. The present invention advantageously permits treatment of patients who have a greater likelihood of responding to treatment by administering therapeutic agents, i.e., anti-FOLR1 antibodies or anti-FOLR1 immunoconjugates, to patients who are found to have an increased expression level of FOLR1.

The present invention provides a method for identifying a subject pre-disposed to respond favorably to a Folate Receptor 1 (FOLR1)-targeting anti-cancer therapeutic, the method comprising detecting FOLR1 expression in a tissue sample from the subject.

The present invention also provides a method for increasing the likelihood of effectiveness of a cancer treatment, the method comprising administering a therapeutically effective dose of a FOLR1-targeting anti-cancer therapeutic to a subject, wherein FOLR1 expression in a tissue sample from the subject has been found to be increased.

The present invention also provides a method for predicting effectiveness of a low-dose cancer treatment, the method comprising administering a therapeutically effective dose of a FOLR1-targeting anti-cancer therapeutic to a subject, wherein said subject has been found to have increased expression of FOLR1 in a sample.

In one embodiment, the methods are directed to ovarian carcinoma, non-small cell lung adenocarcinoma (including bronchioloalveolar carcinoma), renal carcinomas, and endometrial carcinomas.

In one embodiment, the extent and uniformity of FOLR1 expression is detected by immunohistochemistry (IHC), flow cytometry, or nucleic acid hybridization. In another embodiment, the level of FOLR1 expression is detected by immunohistochemistry. Non-limiting examples of IHC include IHC methods that distinguish between varying levels of FOLR1 and calibrated IHC methods, such as those described herein. The FOLR1 expression can be scored using an appropriate scoring system, including but not limited to the scoring methods described herein. For example, FOLR1 expression can be scored using a calibrated IHC method that includes a range of 0, 1, 2, 3, and 3+ for staining intensity with 0 being the lowest level of staining intensity and 3+ being the highest level of staining intensity. Alternatively or additionally, FOLR1 expression can be scored using a calibrated IHC method that includes a staining uniformity that ranges from focal (<25% of cells stained), to heterogeneous (25-75% of cells stained), to homogenous (>75% of cells stained), where focal staining is the least uniform staining and homogeneous is the most uniform staining.

In a further embodiment, the FOLR1 expression in a sample (e.g., a tumor tissue sample) is measured and compared to one or more reference samples and the FOLR1 expression in the tissue sample from a subject tumor, xenograft tumor, or cell line has a FOLR1 specific score correlating to extent and uniformity of expression as compared to the one or more reference samples. In various examples, a tissue sample or cell with a level 1, 2, 3 or 3+ FOLR1 staining intensity with a homogeneous staining pattern is considered to have increased FOLR1 expression; a tissue sample or cell with a level 3 FOLR1 staining intensity with heterogeneous or focal staining patterns is considered to have increased FOLR1 expression. In another embodiment the FOLR1 expression in a sample is measured and compared to one or more reference samples to identify a comparable level of staining. In one embodiment, the reference sample has a pre-assigned IHC score and/or a predetermined antigen per cell (or ABC) number and the antigen or ABC number for the sample tissue can be determined based on the comparison.

In one embodiment, the FOLR1 expression in a sample (e.g., a tumor tissue sample) is measured and compared to one or more control samples and the FOLR1 expression in the tissue sample from a subject tumor, xenograft tumor, or cell line has a FOLR1 specific score correlating to extent and uniformity of expression as compared to the one or more control samples. In one embodiment, the FOLR1 expression in the sample is compared to a negative control sample which demonstrates no or low detectable FOLR1 expression. In another embodiment, the FOLR1 expression in the sample is compared to a positive control sample having increased FOLR1 expression (level 1, 2, 3 or 3+). In some embodiments, the control samples include, but are not limited to Namalwa, SW2, SW620, T47D, IGROV-1, 300.19 FR1, HeLa, or KB cells. In particular embodiments, the control samples include cells or cell pellets from cells transfected with folate receptor (e.g., 300.19 FR1).

In one embodiment, the FOLR1-targeting anti-cancer therapeutic is a FOLR1 immunoconjugate. In one embodiment, the immunoconjugate comprises an anti-FOLR1 antibody, a linker, and a cytotoxin.

In a further embodiment, the anti-FOLR1 antibody is huMOV19. In another embodiment, the linker is selected from the group consisting of a cleavable linker, a non-cleavable linker, a hydrophilic linker, and a dicarboxylic acid based linker. In another embodiment, the linker is selected from the group consisting: N-succinimidyl 4-(2-pyridyldithio)pentanoate (SPP) or N-succinimidyl 4-(2-pyridyldithio)-2-sulfopentanoate (sulfo-SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl) cyclohexanecarboxylate (SMCC); N-sulfosuccinimidyl 4-(maleimidomethyl) cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol] ester (NHS-PEG4-maleimide). In another embodiment, the linker is N-succinimidyl 4-(2-pyridyldithio)-2-sulfobutanoate (sulfo-SPDB). In another embodiment, the cytotoxic agent is selected from the group consisting of a maytansinoid, maytansinoid analog, benzodiazepine, taxoid, CC-1065, CC-1065 analog, duocarmycin, duocarmycin analog, calicheamicin, dolastatin, dolastatin analog, auristatin, tomaymycin derivative, and leptomycin derivative or a prodrug of the agent. In another embodiment, the cytotoxic agent is a maytansinoid. In another embodiment, the cytotoxic agent is N(2')-deacetyl-N(2')-(3-mercapto-1-oxopropyl)-maytansine or N(2')-deacetyl-N2-(4-mercapto-4-methyl-1-oxopentyl)-maytansine. In another embodiment, the cytotoxic agent is N(2')-deacetyl-N2-(4-mercapto-4-methyl-1-oxopentyl)-maytansine (DM4). In a further embodiment, the immunoconjugate comprises the antibody HUMOV19, sulfo-SPDB, and DM4 (IMGN853).

The invention is also directed to a kit for measuring FOLR1 expression in a subject comprising a FOLR1 detection reagent, and instructions for use. In one embodiment, the FOLR1 detection reagent comprises a FOLR1 binding peptide, protein or a molecular probe (i.e. nucleic acid). In another embodiment, the FOLR1 detection reagent is an anti-FOLR1 antibody. In another embodiment, the kit further comprises a secondary antibody which binds the anti-FOLR1 antibody. In one embodiment the antibody is included at a concentration of 0.5 to 7.5 µg/ml, desirably 0.9 to 3.8+/−0.5 µg/ml. In various embodiments, the antibody is included at a concentration of 1.0+/−0.5 µg/ml, 1.5+/−0.5 µg/ml, 1.9+/−0.5 µg/ml, 2.5+/−0.5 µg/ml, 3.0+/−0.5 µg/ml, 3.5+/−0.5 µg/ml, 3.8+/−0.5 µg/ml, or up to 4.2 µg/ml. In another embodiment, the antibody is included in concentrated solution with instructions for dilutions to achieve a final concentration of 0.9 to 3.8+/−0.5 µg/ml. In another embodiment, the kit further comprises a detection reagent selected from the group consisting of: an enzyme, a fluorophore, a radioactive label, and a luminophore. In another embodiment, the detection reagent is selected from the group consisting of: biotin, digoxigenin, fluorescein, tritium, and rhodamine.

The kit can also include instructions for detection and scoring of FOLR1 expression. The kit can also include control or reference samples. Non-limiting examples of control or reference samples include tissue samples, cell pellets or cells. The control or reference samples may be derived from tissue culture cell lines (normal or tumor), normal tissue (normal control) or tumor tissues (positive control) samples. Exemplary cell lines include SW620, T47D, IGROV-1, HELA, KB, JEG-3 and cell lines stably or transiently transfected with an expression vector that expresses FOLR1 (e.g., 300.19FR1). Exemplary tissues that may be used as normal reference tissues in the FOLR1 expression detection methods are described herein and include normal lung, salivary gland, and pancreas.

The invention is also directed to a method for identifying a cancer likely to respond to an anti-FOLR1 antibody, or anti-FOLR1 immunoconjugate comprising: (a) contacting a biological sample comprising cells from said cancer with an agent that binds FOLR1 protein on the cell surface; (b) detecting binding of said agent that binds FOLR1 protein on the cell surface of said biological sample of (a); (c) assigning a score to said binding of step (b), wherein said score is assigned based on comparison to one or more reference samples; and (d) comparing said score in step (c) to the score of a reference tissue or cell, wherein a score for said cancer FOLR1 level that is greater than the score for a normal or low FOLR1 expressing reference sample or a score for said cancer FOLR1 level that is equal to or greater than the score for a high FOLR1 expressing reference sample identifies said cancer as likely to respond to an anti-FOLR1 antibody or anti-FOLR1 immunoconjugate. In certain embodiments, the cancer is ovarian or lung cancer.

The invention is also directed to a method of identifying a tumor as sensitive to treatment with an anti-FOLR1 antibody, or anti-FOLR1 immunoconjugate, said method comprising: (a) measuring the level of FOLR1 expression in a tumor tissue sample obtained from said tumor, wherein said measuring comprises the use of a detection method that distinguishes between staining intensity or staining uniformity in a FOLR1 expressing cancer sample as compared to staining intensity or staining uniformity in one or more reference samples; (b) determining a FOLR1 staining intensity score for said tumor tissue sample; and (c) comparing the FOLR1 staining intensity score determined in step (b) to a relative value determined by measuring FOLR1 protein expression in at least one reference sample, wherein said at least one reference sample is a tissue, cell, or cell pellet sample which is not sensitive to treatment with an anti-FOLR1 antibody, or anti-FOLR1 immunoconjugate, and wherein a FOLR1 staining intensity score for said sample determined in step (b) that is higher than said relative value identifies said tumor as being sensitive to treatment with an anti-FOLR1 antibody, or anti-FOLR1 immunoconjugate. In certain embodiments, the detection method is performed manually or using an automated system. In one embodiment, the detection method is IHC. In another embodiment, the IHC is calibrated IHC that can distinguish different levels of FOLR1 expression.

The invention is also directed to a method of optimizing a therapeutic regimen with an anti-FOLR1 antibody or an anti-FOLR1 immunoconjugate for a subject having lung or ovarian cancer, said method comprising: (a) contacting said sample from said subject with an antibody that specifically binds cell surface FOLR1; (b) measuring the binding of said antibody in (a) to said cell surface FOLR1 in said sample using a detection method that can distinguish between staining intensity or staining uniformity in a FOLR1 expressing cancer sample as compared to staining intensity or staining uniformity in one or more reference samples and assigning a staining score to said sample; and (c) administering a high dose of an anti-FOLR1 immunoconjugate when the score in step (b) is less than or equal to the score for a normal or low FOLR1 expressing reference sample or administering a low dose of an anti-FOLR1 immunoconjugate when the score is greater than the score for a normal or low FOLR1 expressing reference sample.

The invention is also directed to a method of detecting the expression of cell surface FOLR1 on cancer cells in a tumor tissue sample from a subject, said method comprising: (a) obtaining tumor tissue sample, wherein said cancer sample is formalin-fixed paraffin embedded; (b) contacting said sample with an antibody that specifically binds cell surface FOLR1; (c) measuring the binding of said antibody in (b) to said cell surface FOLR1 in said tumor tissue sample using a detection method that can distinguish between staining intensity or staining uniformity in a FOLR1 expressing cancer sample as compared to staining intensity or staining uniformity in one or more reference samples; and (d) assigning a FOLR1 expression score to said FOLR1 after comparing the level of cell surface FOLR1 staining intensity or staining uniformity in said tumor tissue sample to one or more reference samples.

The invention is also directed to a method of identifying a subject having a lung or ovarian cancer as likely to respond to a low dose anti-FOLR1 antibody or anti-FOLR1 immunoconjugate treatment regimen, said method comprising: (a) contacting a biological sample comprising cells from said ovarian or lung cancer with an agent that binds cell surface FOLR1 protein; (b) detecting binding of said agent to said biological sample of (a); (c) assigning a score to said binding of step (b), wherein said score is assigned based on comparison to one or more reference samples; and (d) comparing said score in step (c) to the score of a reference tissue or cell, wherein a score for said ovarian or lung cancer FOLR1 level that is greater than the score for a normal or low FOLR1 expressing reference sample or a score for said ovarian or lung cancer FOLR1 level that is equal to or greater than the score for a high FOLR1 expressing reference sample identifies said ovarian or lung cancer as likely to respond to a low dose anti-FOLR1 antibody or anti-FOLR1 immunoconjugate. In certain embodiments, the method further comprises administering a therapeutically effective amount of a humanized anti-FOLR1 antibody or an anti-FOLR1 immunoconjugate to said subject.

BRIEF DESCRIPTIONS OF THE DRAWINGS

FIG. 1. Manual Staining Method: Anti-FOLR1 antibodies detect FOLR1 expression in transfected cells. 300.19 cells were transfected with a polynucleotide that encodes human FOLR1. FOLR1 protein expression was detected using the murine antibody BN3.2. Smith A E et al, *Hybridoma (Larchmt)*. 2007 October; 26 (5): 281-8.

Figure 2:
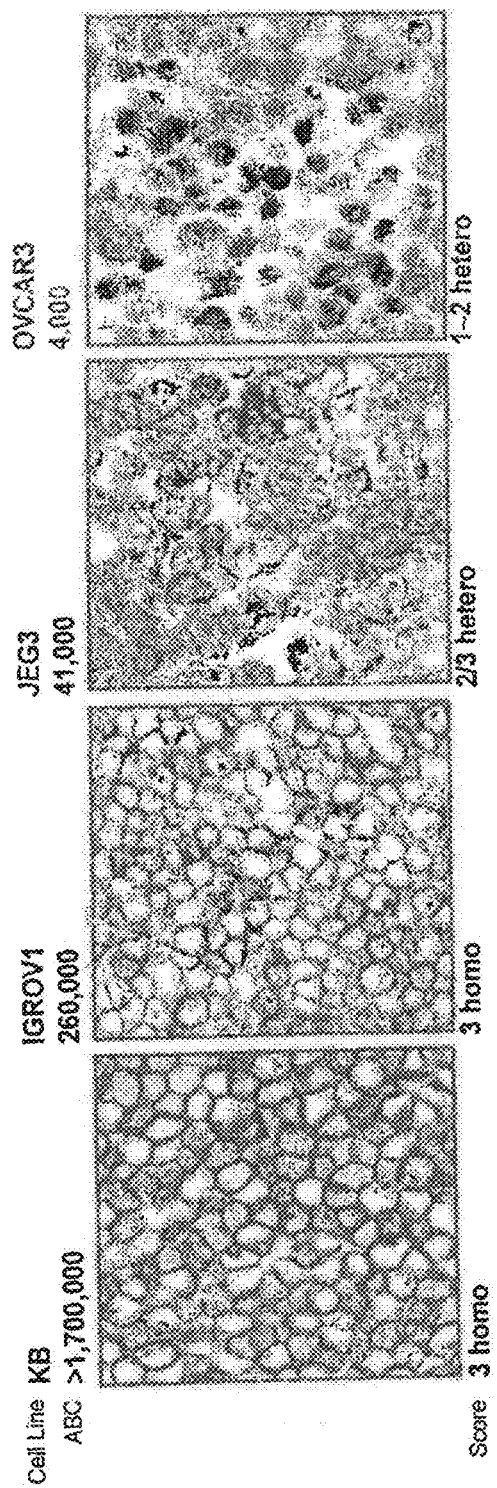

FIG. 2. Manual Staining Method: Anti-FOLR1 antibodies can distinguish different levels of FOLR1 expression. Antibody BN3.2 was used to detect FOLR1 expression in various xenograft cells. The limit of detection for the BN3.2 antibody was approximately 4000 antibodies bound per cell (ABC).

Figure 3:
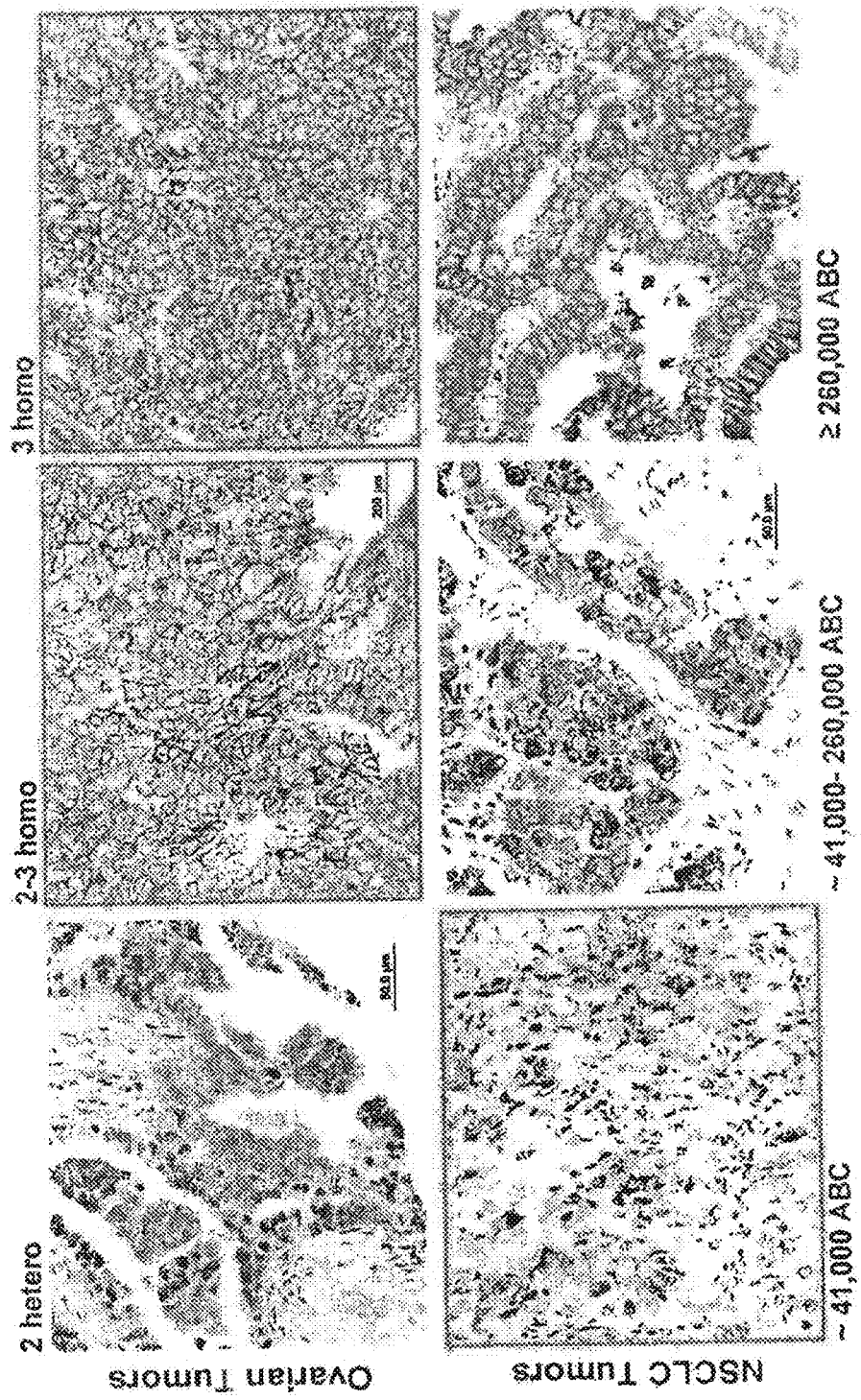

FIG. 3. Manual Staining Method: Anti-FOLR1 antibodies can distinguish different levels of FOLR1 expression in tissue samples. BN3.2 was used to detect FOLR1 expression in both ovarian tumors (A), as well as non-small cell lung cancer tumors (B).

Figure 4:
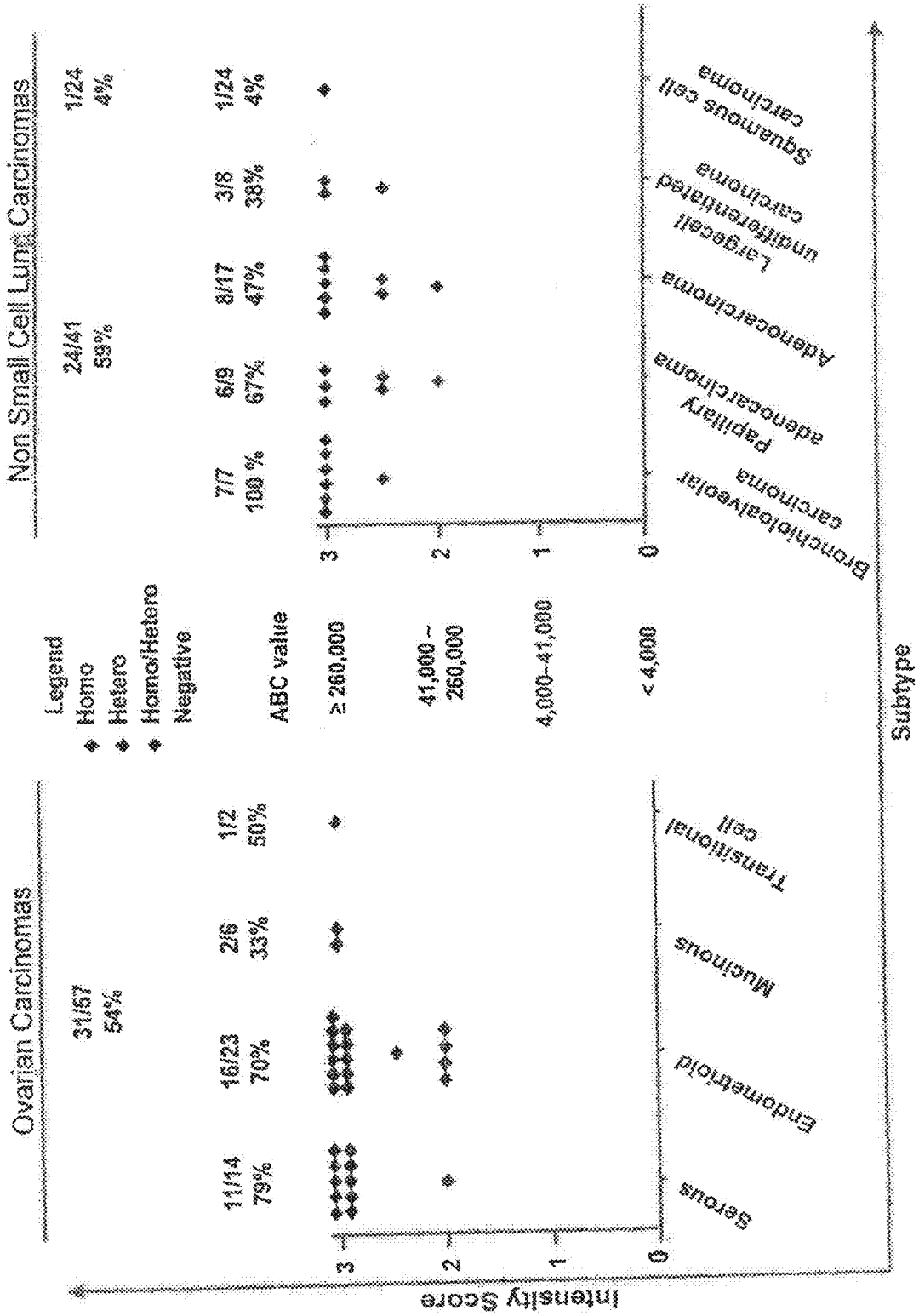

FIG. 4. Manual Staining Method: Uniform FOLR1 expression in ovarian and NSCLC tumors. FOLR1 expression was high in many of the ovarian carcinomas, as well as lung adenocarcinomas and bronchioloalveolar carcinomas tested. The majority of ovarian carcinoma samples had the highest intensity staining in serous or endometrioid cells. In the NSCLC tumors, the highest ABC values were found in bronchioloalveolar carcinoma and papillary adenocarcinoma.

Figure 5:
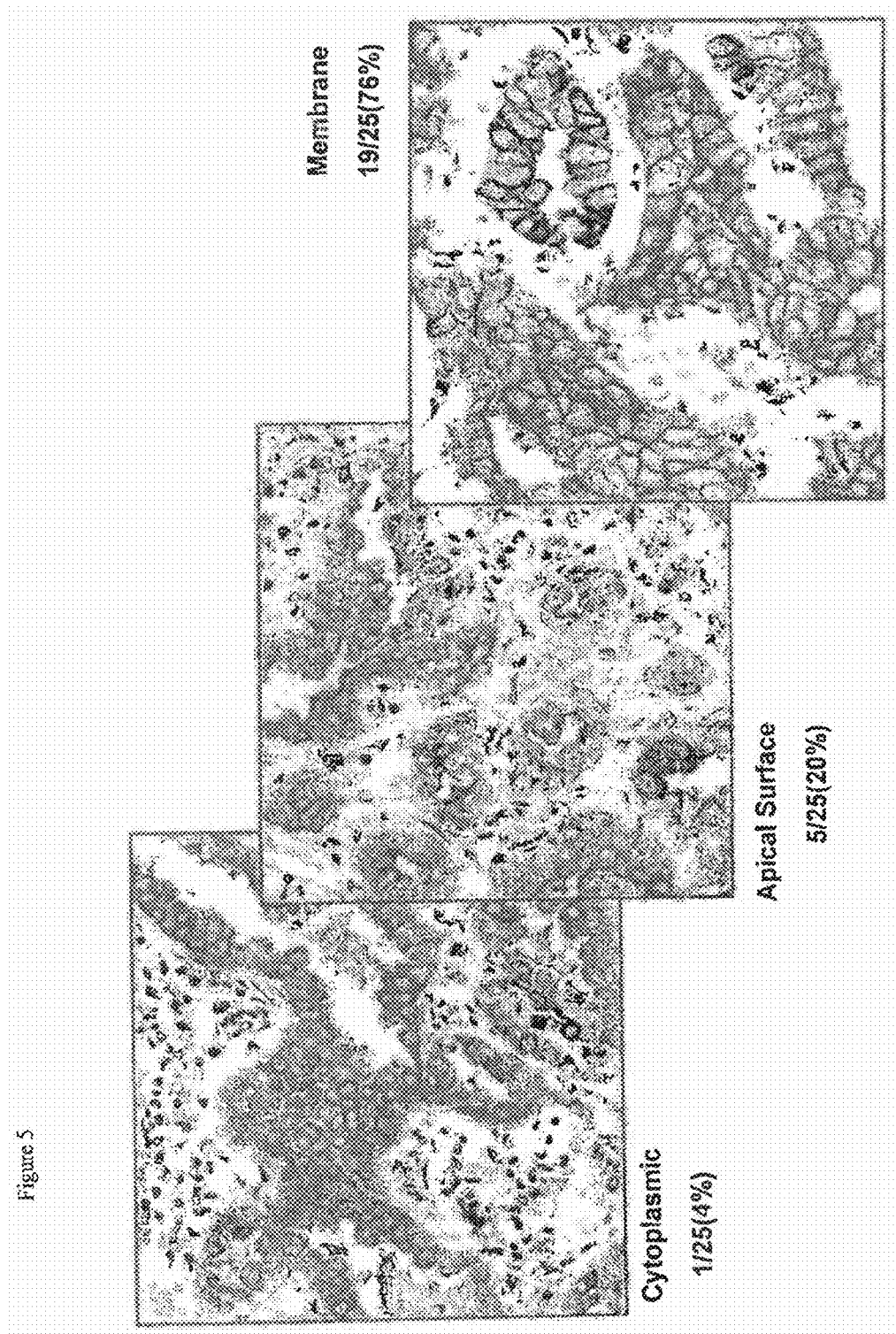

FIG. 5. Manual Staining Method: FOLR1 expression is generally confined to the membrane of NSCLC cells. High resolution microscopy revealed that the majority of FOLR1 staining was restricted to the membrane in NSCLC tumors.

Figure 6:
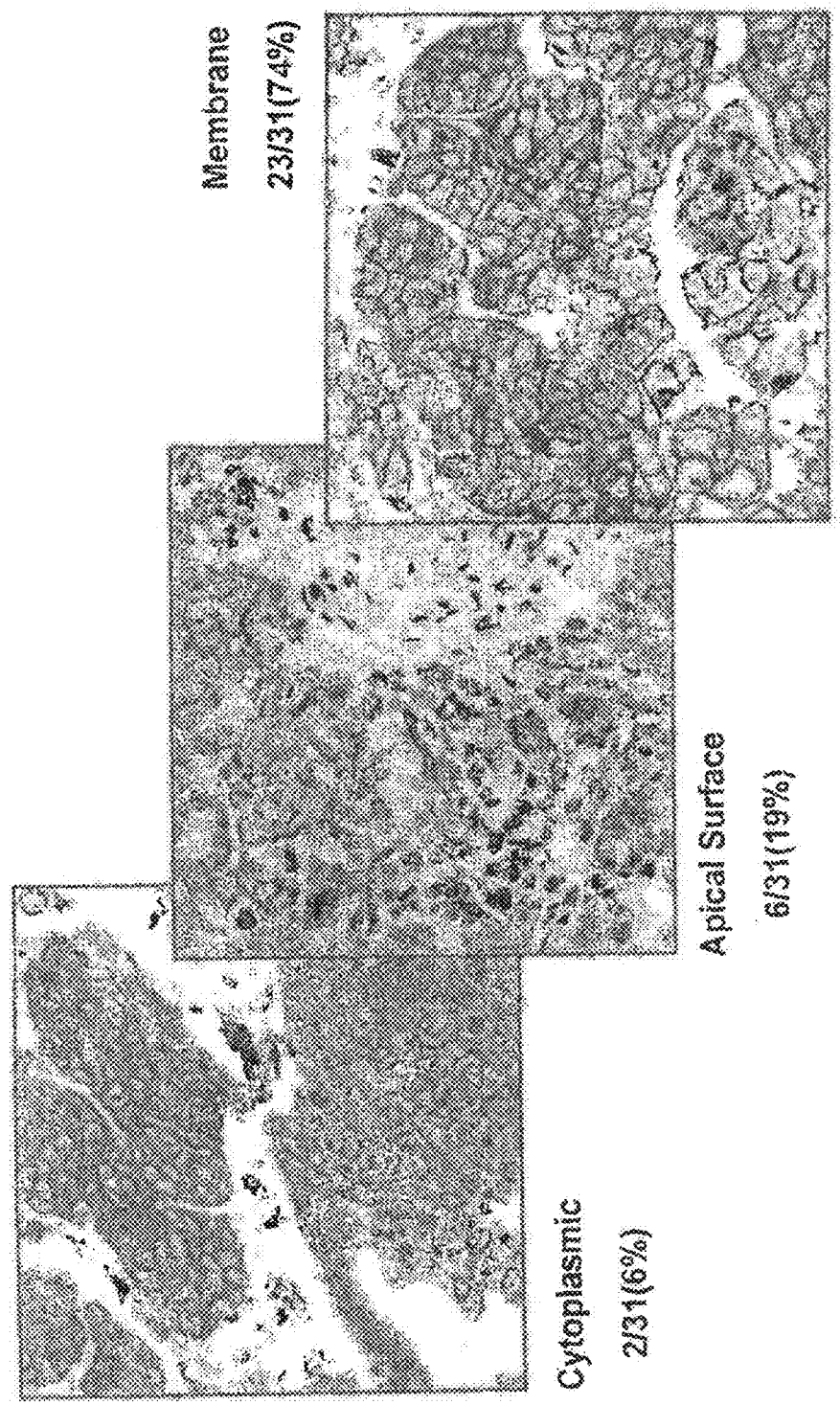

FIG. 6. Manual Staining Method: FOLR1 expression is generally confined to the membrane of ovarian cancer cells. High resolution microscopy revealed that the majority of FOLR1 staining was restricted to the membrane in ovarian tumors.

Figure 7:
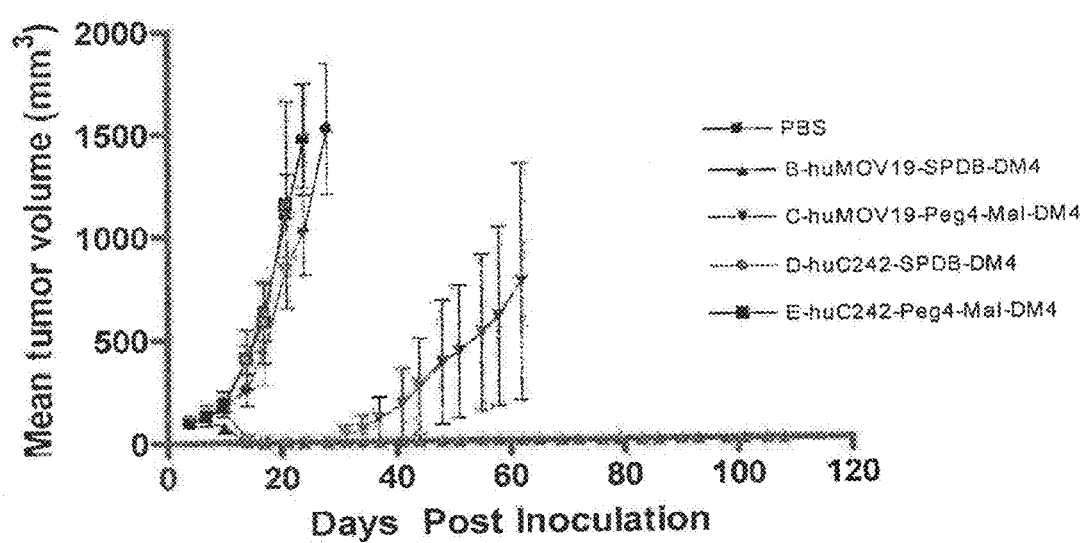

FIG. 7. In vivo efficacy of huMov19-targeted conjugates in a KB xenograft model. FOLR1-targeting cleavable conjugate huMov19-SPDB-DM4 (B) in comparison with non-FOLR1-targeting huC242-SPDB-DM4 (D), and non-cleavable conjugate huMov19-PEG4-Mal-DM4 (C) in comparison with non-targeting huC242-PEG4Mal-DM4 (E) were tested using an established xenograft model of KB cells implanted subcutaneous into SCID mice. Targeting of FOLR1 by huMov19 resulted in significant reduction in mean tumor volume.

Figure 8:
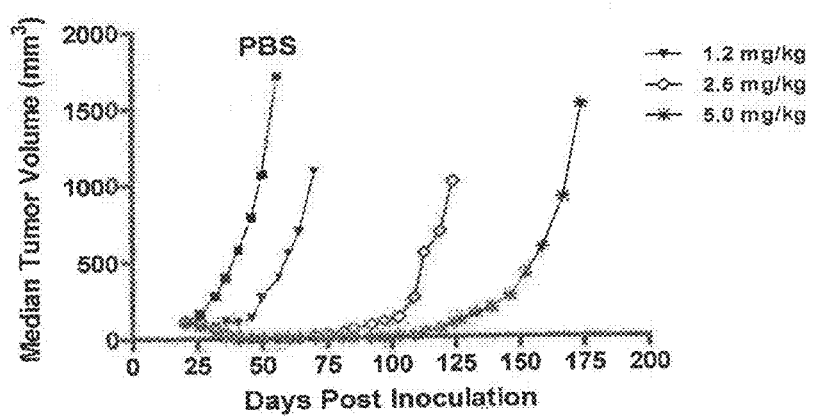

FIG. 8. Dose-response anti-tumor activity of IMGN853 treatment in OVCAR-3 human ovarian carcinoma xenografts. Mice were treated with a single intravenous injection of IMGN853 at 1.2, 2.5 or 5.0 mg/kg. A control group of animals received a single intravenous injection of PBS.

Figure 9:
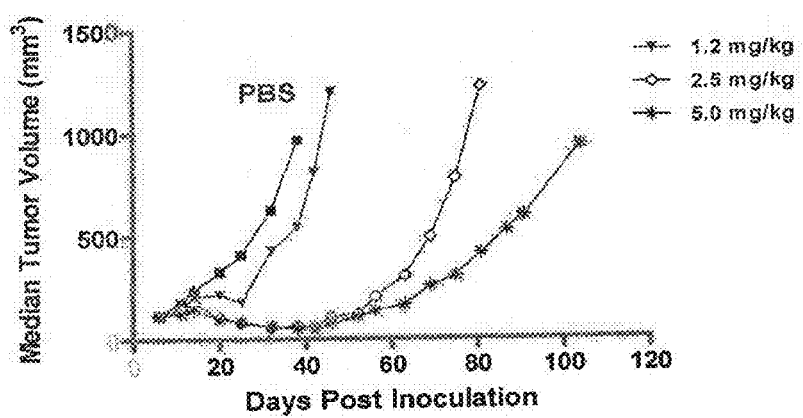

FIG. 9. Dose-response anti-tumor activity of IMGN853 treatment in IGROV-1 human ovarian carcinoma xenografts. Mice were treated with a single intravenous injection of IMGN853 at 1.2, 2.5 or 5.0 mg/kg. A control group of animals received a single intravenous injection of PBS.

Figure 10:
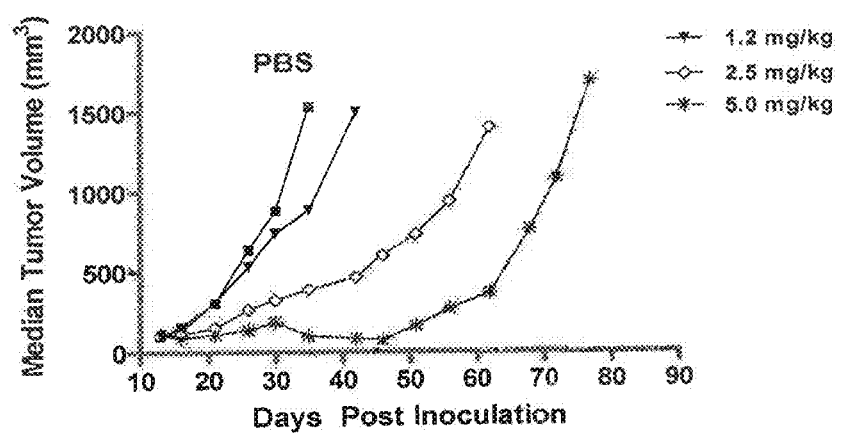

FIG. 10. Dose-response anti-tumor activity of IMGN853 treatment in OV-90 human ovarian carcinoma xenografts. Mice were treated with a single intravenous injection of IMGN853 at 1.2, 2.5 or 5.0 mg/kg. A control group of animals received a single intravenous injection of PBS.

Figure 11:
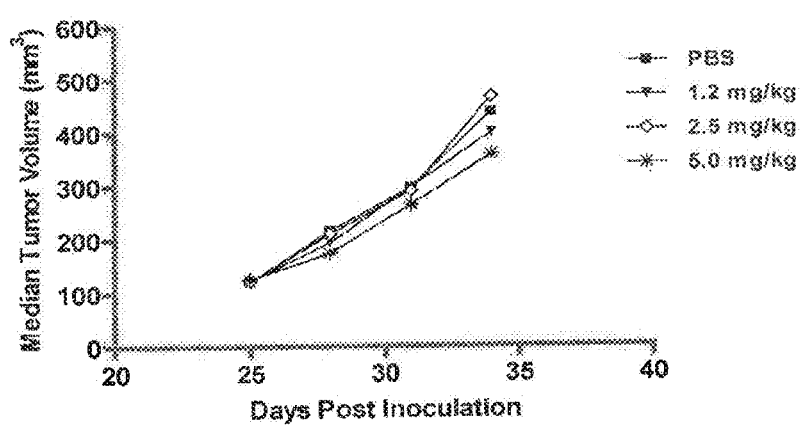

FIG. 11. Dose-response anti-tumor activity of IMGN853 treatment in SKOV-3 human ovarian carcinoma xenografts. Mice were treated with a single intravenous injection of IMGN853 at 1.2, 2.5 or 5.0 mg/kg. A control group of animals received a single intravenous injection of PBS.

Figure 12:
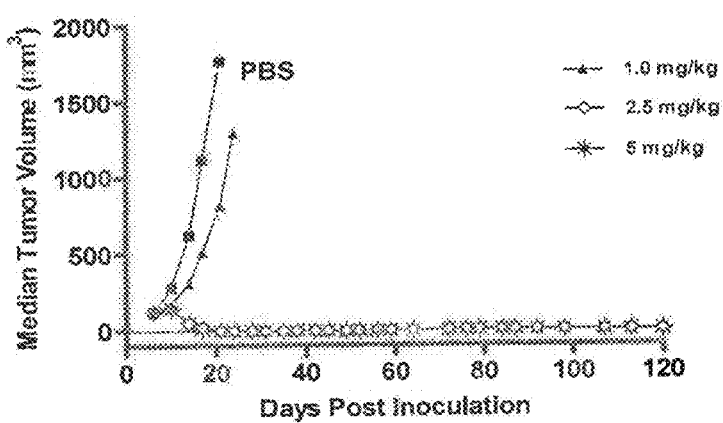

FIG. 12. Dose-response anti-tumor activity of IMGN853 treatment in KB human cervical adenocarcinoma xenografts. Mice were treated with a single intravenous injection of IMGN853 at 1.0, 2.5 or 5.0 mg/kg. A control group of animals received a single intravenous injection of PBS.

Figure 13:
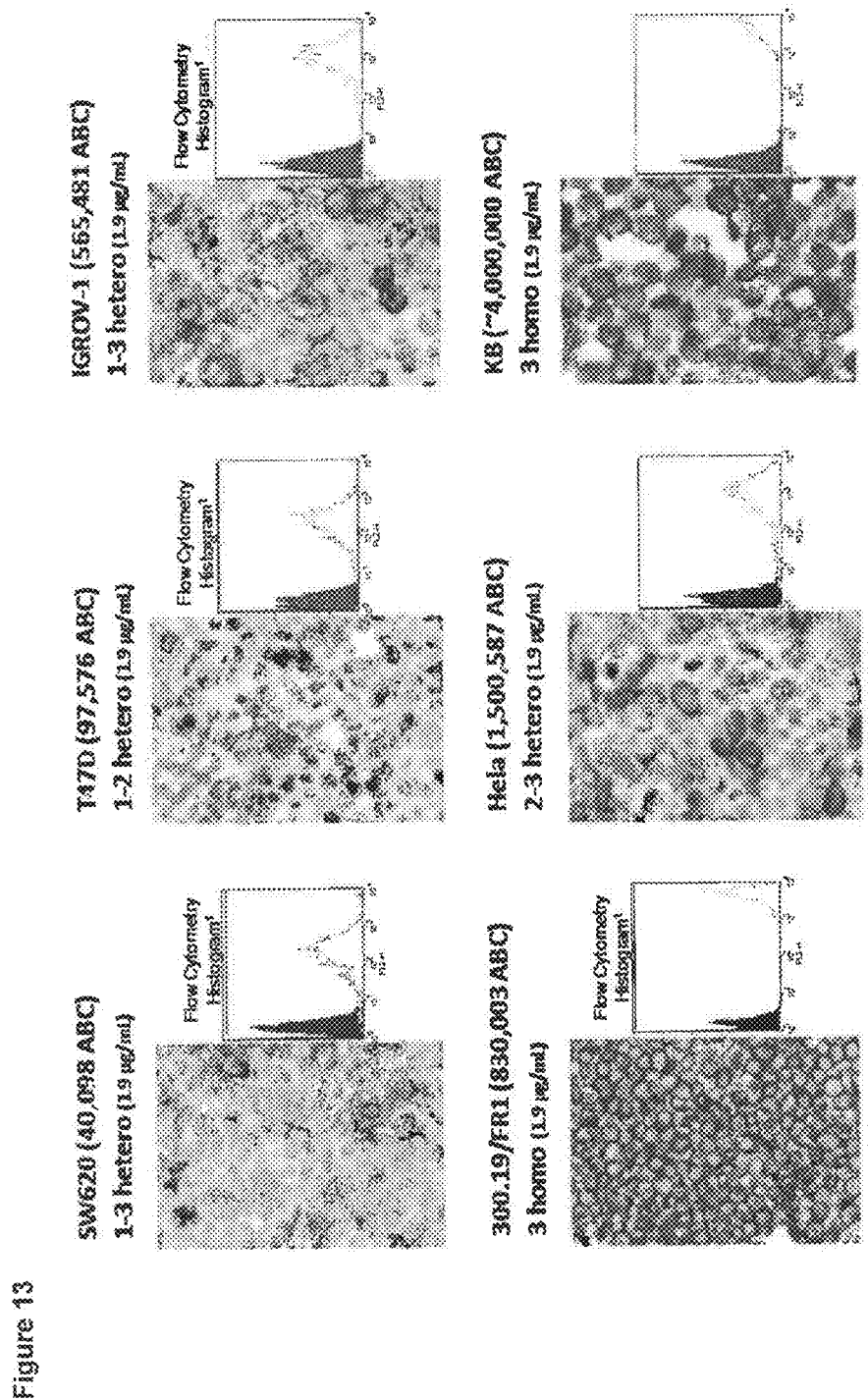

FIG. 13. Automated Staining Methods: Representative Photographs and Histograms depicting FOLR1 Expression in Cell Lines by IHC and Flow Cytometry. SW620, T47D, Igrov-1, 300.19/FR1, HeLa, and KB cells were all scored for FOLR1 staining intensity and uniformity. SW630 and IGROV-1 cells were scored 1-3 hetero, T47D was scored 1-2 hetero, HeLa was scored 2-3 hetero, while 300.19/FR1 and KB were scored 3 homo.

Figure 14:
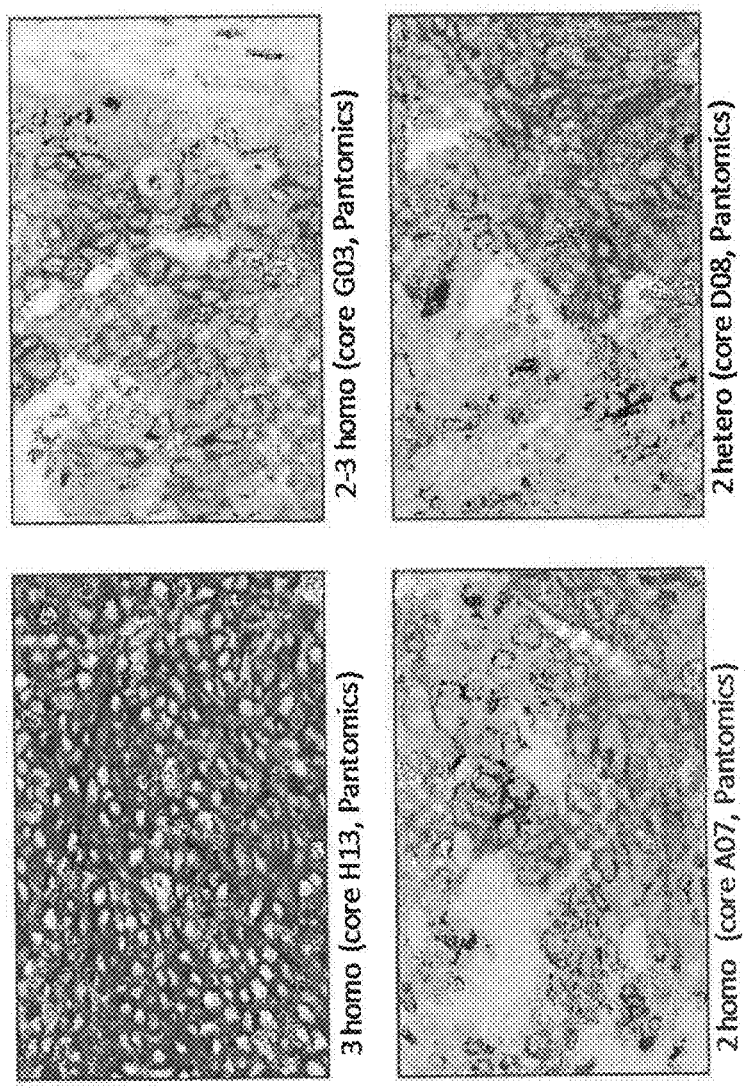

FIG. 14. Automated Staining Methods: Representative FOLR1 Staining in Serous Ovarian Cancer. Staining patterns demonstrating 3 homo, 2-3 homo, 2 homo, and 2 hetero staining are shown for tissue sections from serous ovarian cancer by IHC.

Figure 15:
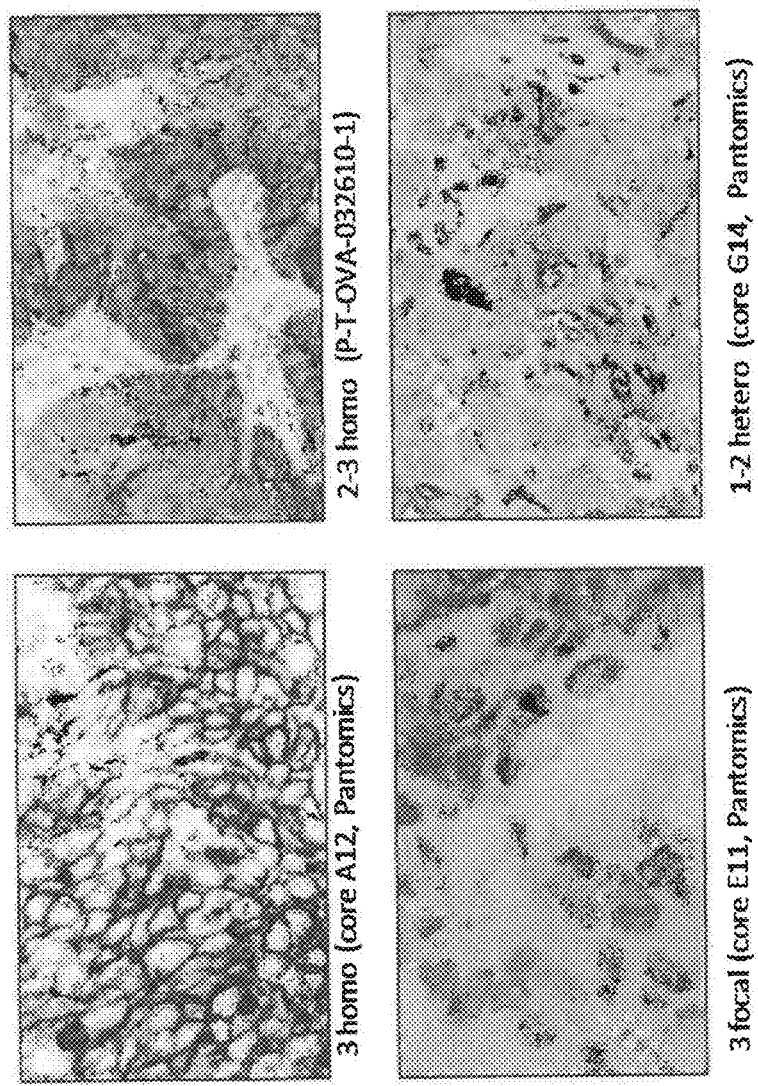

FIG. 15. Automated Staining Methods: Representative FOLR1 Staining in Endometrioid Ovarian Cancer. Staining patterns demonstrating 3 homo, 2-3 homo, 3 focal, and 1-2 hetero staining are shown for tissue sections from endometroid cancer by IHC.

Figure 16:
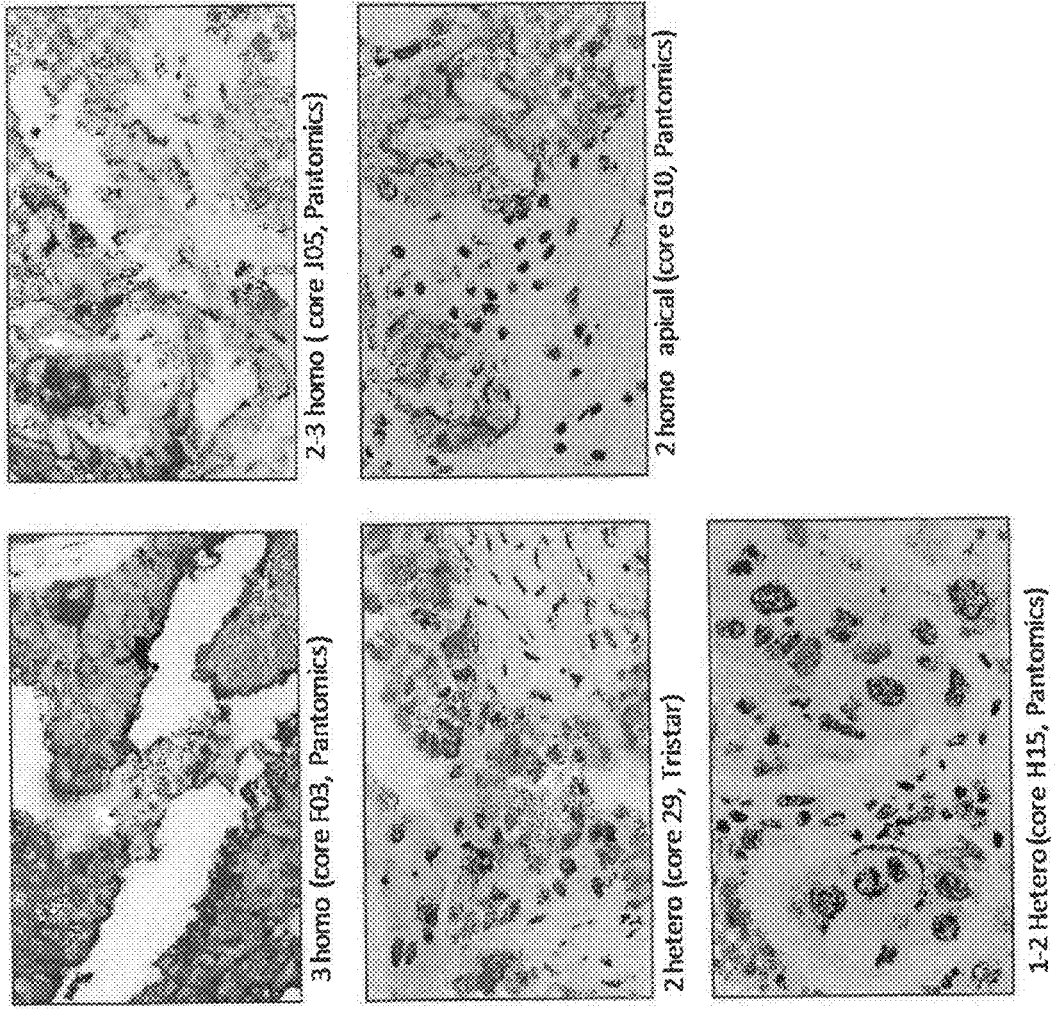

FIG. 16. Automated Staining Methods: Representative FOLR1 Staining in NSCLC of the Adenocarcinoma Subtype (excluding bronchioloalveolar carcinomas). Staining patterns demonstrating 3 homo, 2-3 homo, 2 hetero, 2 homo, and 1-2 hetero staining are shown for tissue sections from non-small cell lung cancer, adenocarcinoma subtype by IHC.

Figure 17:
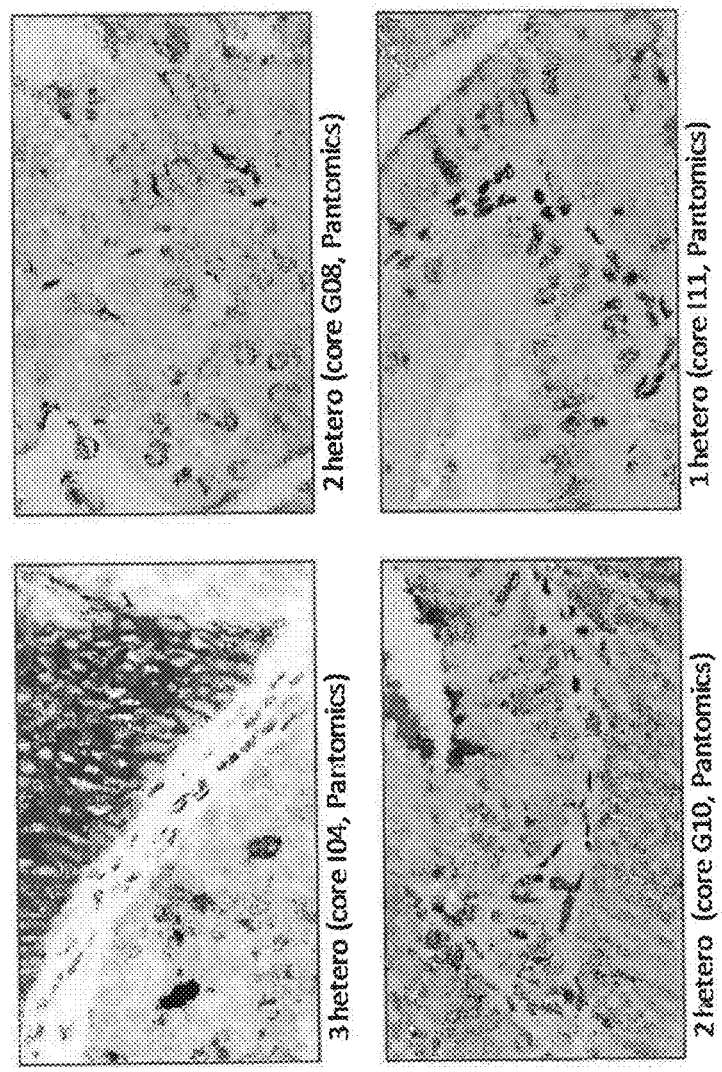

FIG. 17. Automated Staining Methods: Representative FOLR1 Staining in Endometrial Adenocarcinoma. Staining patterns demonstrating 3 hetero, 2 hetero, and 1 hetero staining are shown for tissue sections from endometrial adenocarcinoma by IHC.

Figure 18:
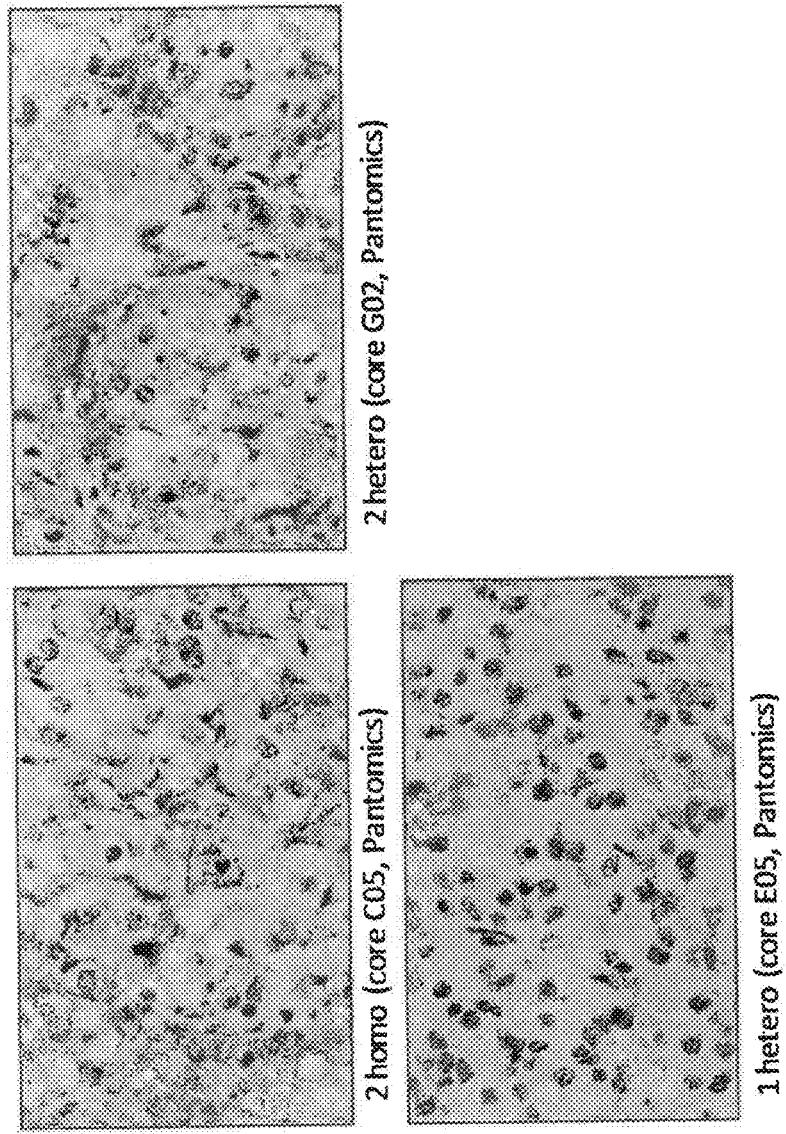

FIG. 18. Automated Staining Methods: Representative FOLR1 Staining in Renal Clear Cell Carcinoma. Staining patterns demonstrating 2 homo, 2 hetero, and 1 heteto staining are shown for tissue sections from renal cell cancer by IHC.

Figure 19:
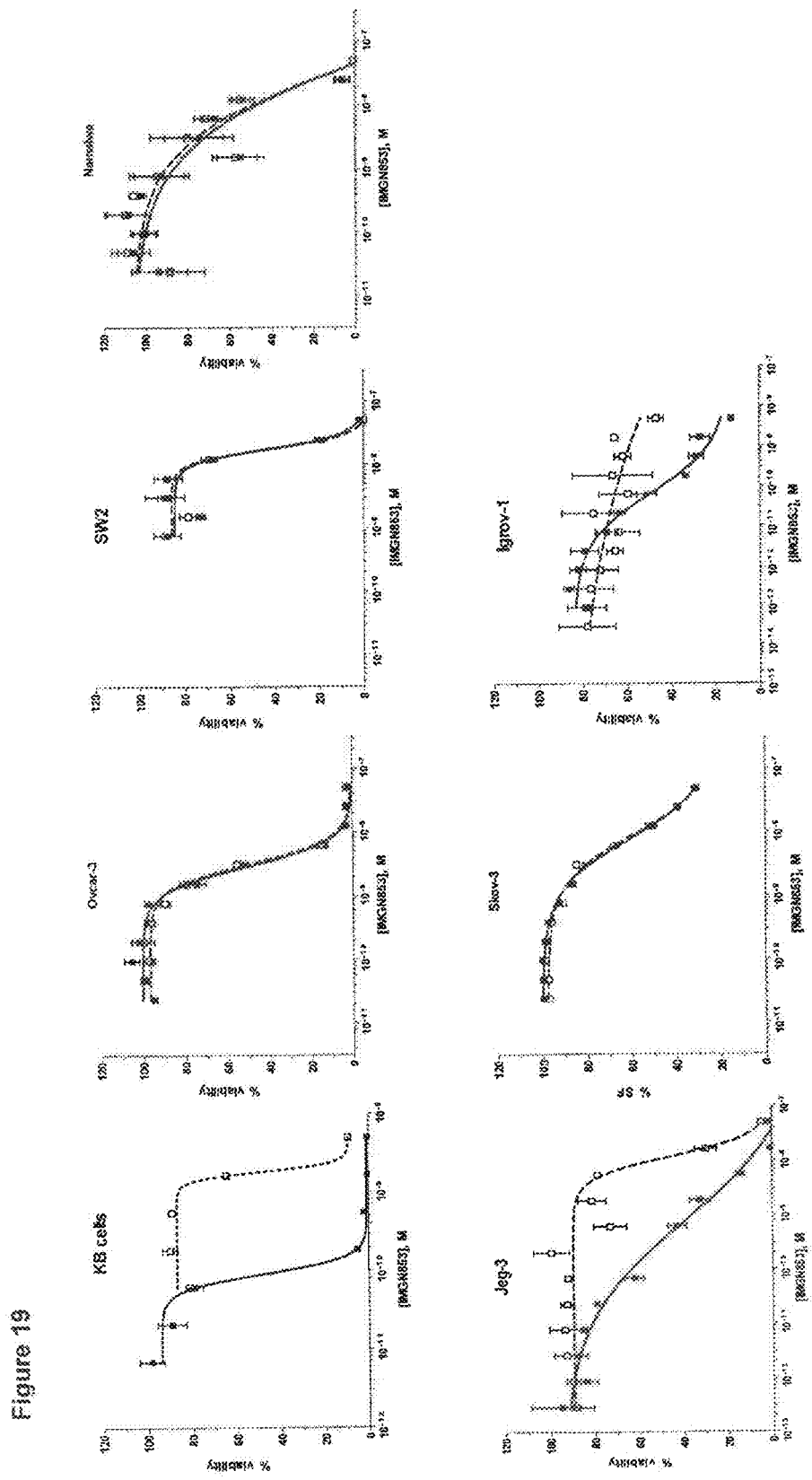

FIG. 19. The cytotoxic activity of IMGN853 in vitro. Five FOLR1-positive cell lines (KB, IGROV-1, JEG-3, SKOV-3 and OVCAR-3) and two FOLR1-negative cell lines (Namalwa and SW2) were analyzed for their sensitivity to the cytotoxic effects of IMGN853. Cells were exposed to IMGN853 (solid line) or to IMGN853 plus 0.5 µM unconjugated huMov19 (M9346A) (dashed line) for 5 days, and the cell survival was determined by WST-8-based assay. Representative data are shown. The percent of surviving cells was plotted against base 10 logarithm of the concentration of IMGN853.

Figure 20:
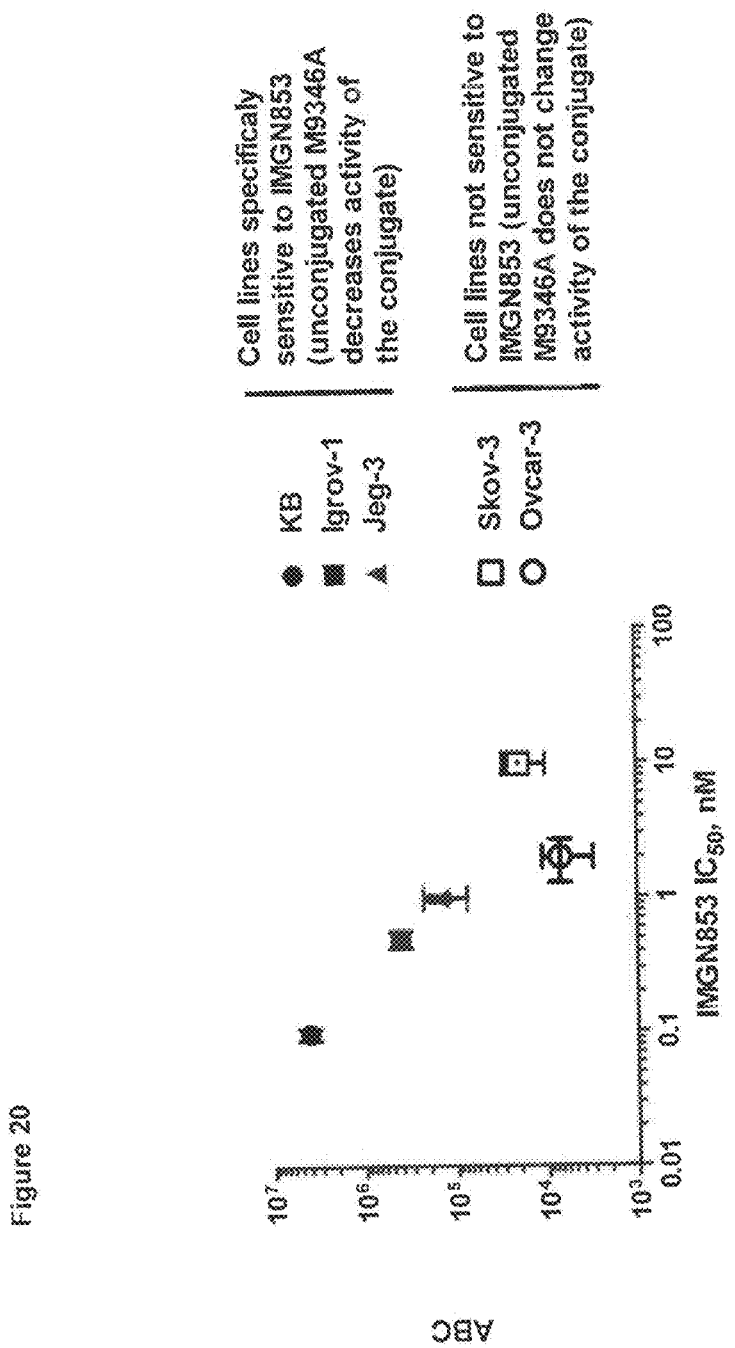

FIG. 20. The sensitivity of the FOLR1-positive cell lines to IMGN853 versus the level of FOLR1 expression. Potency and specificity of IMGN853 was analyzed against FOLR1-positive cell lines with a wide range of FOLR1 expression. Cell lines were incubated with IMGN853 and KB, Igrov-1, and Jeg-3 were specifically sensitive to IMGN853 while unconjugated huMov19 (M9346A) showed decreased activity of the conjugate. Skov-3 and Ovcar-3 were not sensitive to IMGN853 and unconjugated huMov19 (M9346A) did not change the activity of the conjugate.

Figure 21:
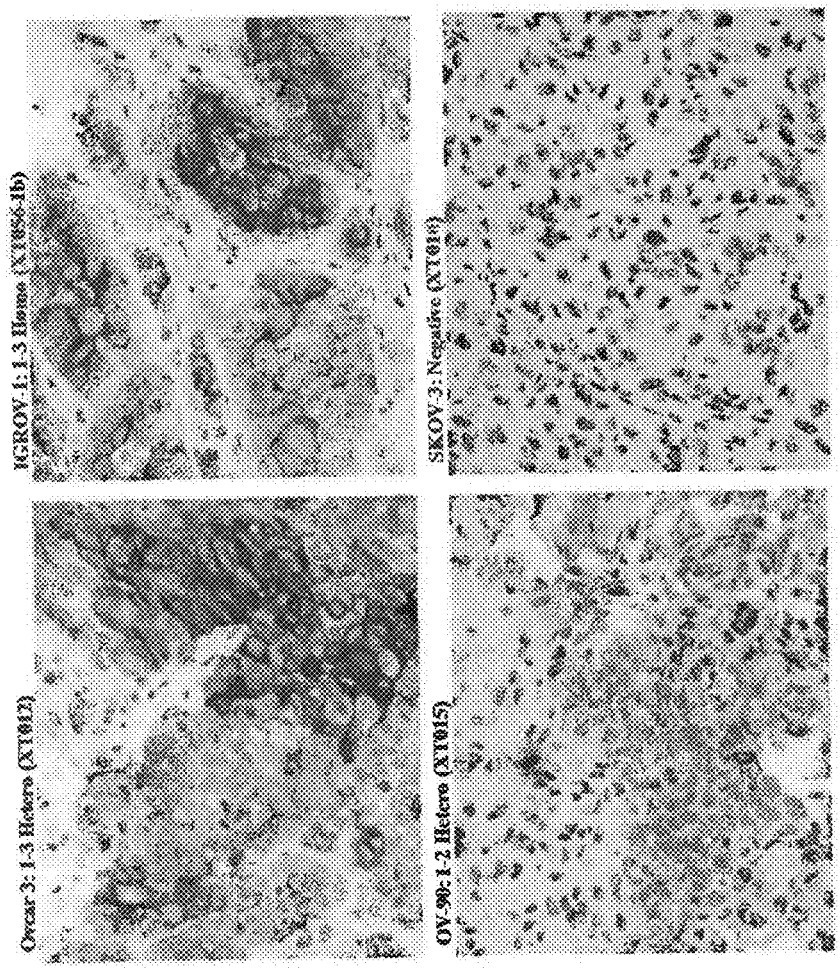

FIG. 21. Automated Staining Methods: Ovarian Carcinoma Xenograft efficacy models stained for FOLR1. Staining patterns demonstrating 1-3 hetero (Ovcar 3), 1-3 homo (Igrov 1), 1-2 hetero (Ov 90) and negative (SKOV 3) are shown for tissue sections from ovarian cancer xenografts by IHC.

Figure 22:
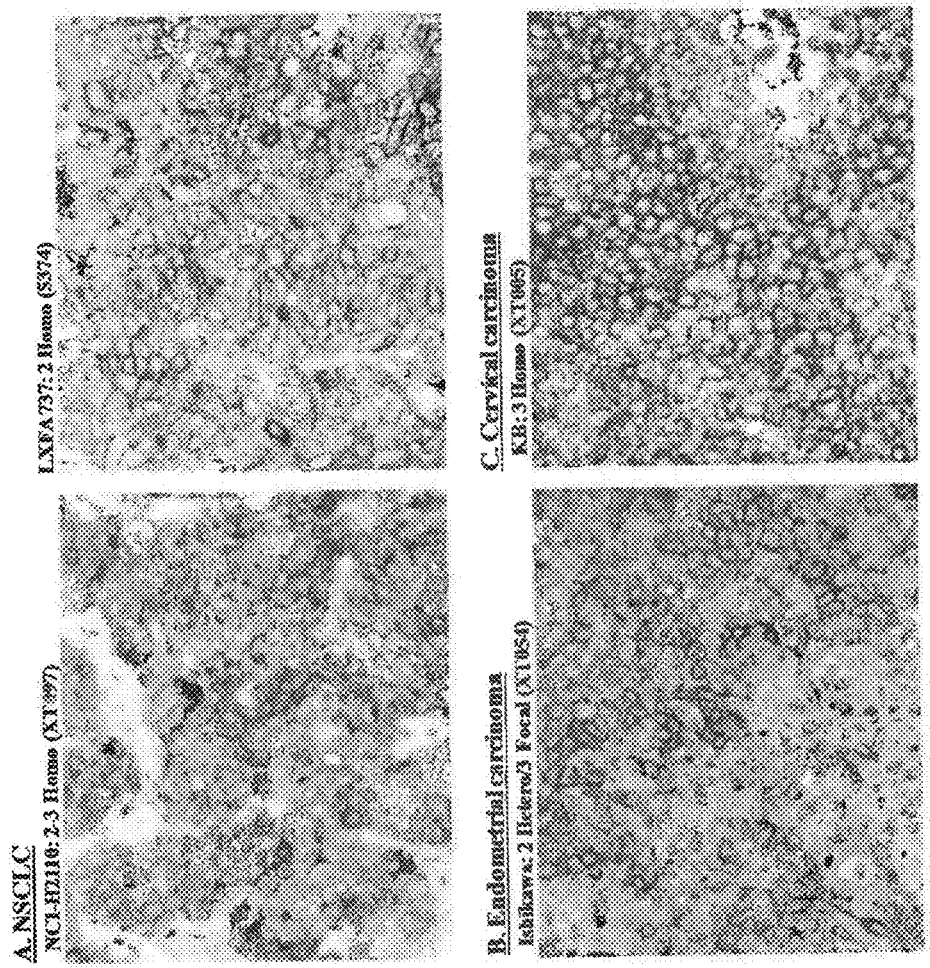

FIG. 22. Automated Staining Methods: Mouse Xenograft Models. Staining patterns for FOLR1 in xenografts for NSCLC (A), Endometrium Carcinoma (B) and Cervical Carcinoma (C) Cell Lines are shown. NSCLC samples demonstrated 2-3 homo or 2 homo staining, endometrium carcinoma demonstrated 2 hetero/3 focal staining, and cervical carcinoma demonstrated 3 homo staining.

Figure 23:
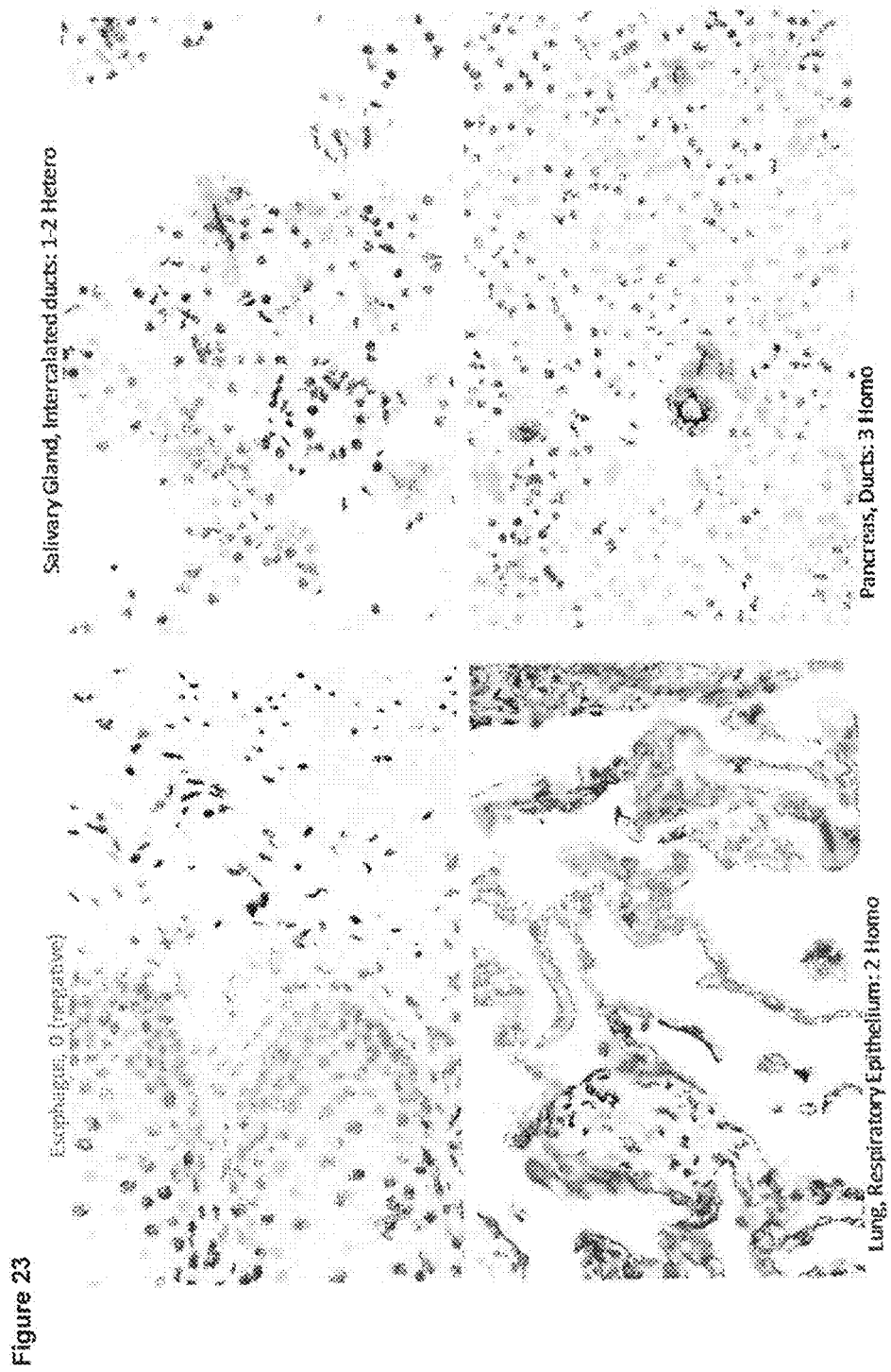

FIG. 23. Assay control tissues automated staining guide. Staining patterns for negative (esophagus 0) and positive control samples (salivary gland 1-2 hetero, lung 2 homo, pancreas 3 homo) are shown as determined by automated IHC.

Figure 24:
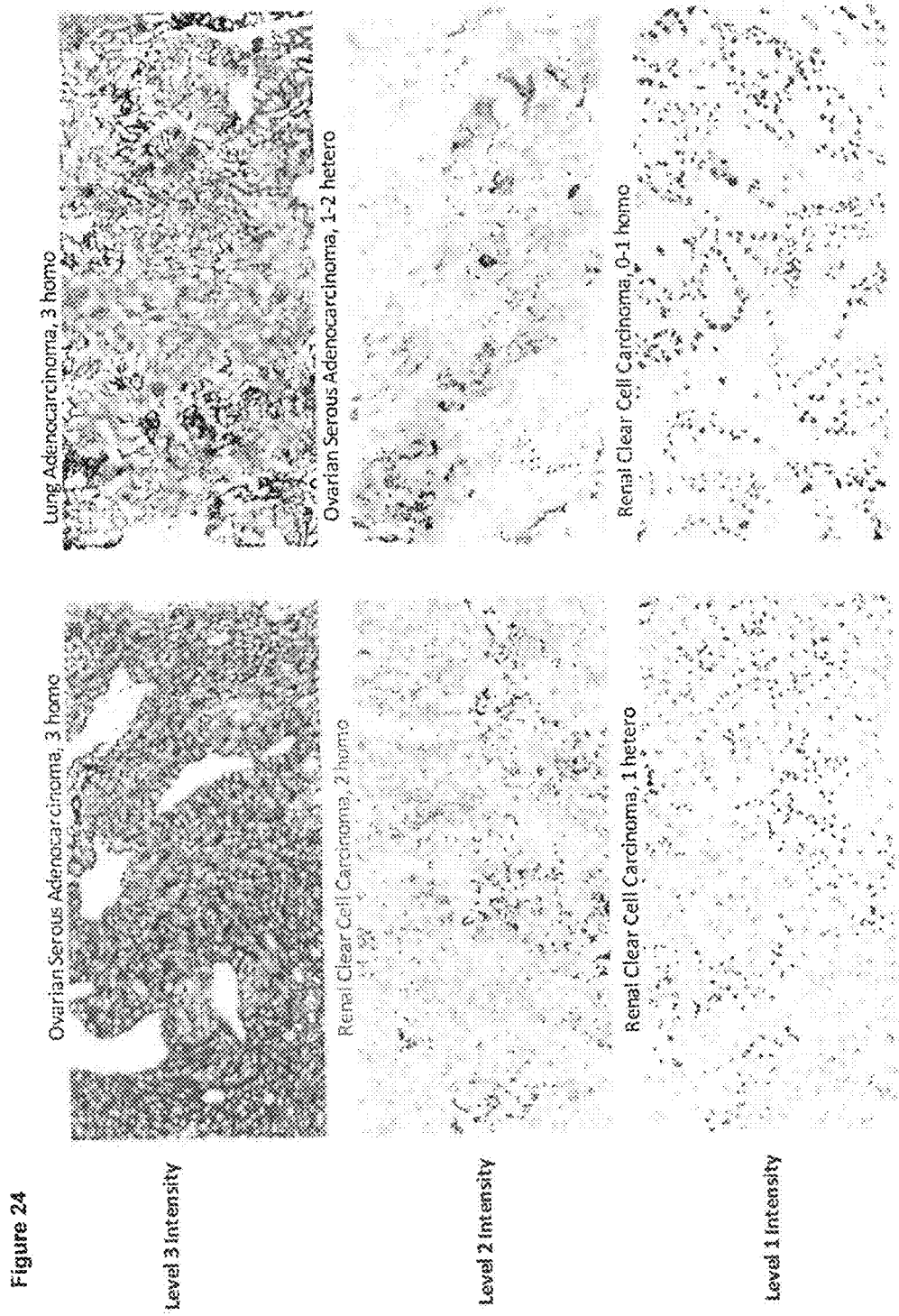

FIG. 24. Tumor tissues automated staining guide. Representative staining patterns for level 3, level 2, and level 1 staining are shown on control tissue as determined by automated IHC.

FIG. 25. Tumor tissues automated staining guide. Representative staining patterns for level 3, level 2, and level 1/negative staining are shown on control tissue as determined by automated IHC.

DETAILED DESCRIPTION OF THE INVENTION

The present invention provides methods for increasing the efficacy of or the likelihood of response to the treatment of cancers characterized by the overexpression of FOLR1. The present invention is based on the discovery of a dynamic range of expression of FOLR1 in tumor tissue as compared to normal tissue and the discovery that tumors with increased levels of FOLR1 expression are more responsive to treatment with anti-FOLR1 antibodies or anti-FOLR1 immunoconjugates. We have also discovered differences in sensitivity and detection of dynamic ranges between automated and manual methods. Kits comprising one or more reagents useful for practicing the methods of the invention are further provided.

I. Definitions

To facilitate an understanding of the present invention, a number of terms and phrases are defined below.

The terms "human folate receptor 1" or "FOLR1", as used herein, refers to any native human FOLR1, unless otherwise indicated. The term "FOLR1" encompasses "full-length," unprocessed FOLR1 as well as any form of FOLR1 that results from processing within the cell. The term also encompasses naturally occurring variants of FOLR1, e.g., splice variants, allelic variants and isoforms. The FOLR1 polypeptides described herein can be isolated from a variety of sources, such as from human tissue types or from another source, or prepared by recombinant or synthetic methods. Examples of FOLR1 sequences include, but are not limited to NCBI reference numbers P15328, NP_001092242.1, AAX29268.1, AAX37119.1, NP_057937.1, and NP_057936.1, and those shown in SEQ ID NOs: 1 and 2.

The term "increased expression" of FOLR1 refers to a sample which contains elevated levels of FOLR1 expression. In one example, the FOLR1 expression is measured by IHC and given a staining intensity score or a staining uniformity score by comparison to controls (e.g., calibrated controls) exhibiting defined scores (e.g. an intensity score of 3 is given to the test sample if the intensity is comparable to the level 3 calibrated control or an intensity of 2 is given to the test sample if the intensity is comparable to the level 2 calibrated control). For example, a score of 1, 2, 3, or 3+ or greater by immunohistochemistry indicates an increased expression of FOLR1. A staining uniformity that is heterogeneous or homogeneous is also indicative of increased FOLR1 expression. The staining intensity and staining uniformity scores can be used alone or in combination (e.g., 2 homo, 2 hetero, 3 homo, 3 hetero, etc.). In another example, an increase in FOLR1 expression can be determined by detection of an increase of at least 2-fold, at least 3-fold, or at least 5-fold) relative to control values (e.g., expression level in a tissue or cell from a subject without cancer or with a cancer that does not have elevated FOLR1 values).

A "reference sample" can be used to correlate and compare the results obtained in the methods of the invention from a test sample. Reference samples can be cells (e.g., cell lines, cell pellets) or tissue. The FOLR1 levels in the "reference sample" may be an absolute or relative amount, a range of amount, a minimum and/or maximum amount, a mean amount, and/or a median amount of FOLR1. The diagnostic methods of the invention involve a comparison between expression levels of FOLR1 in a test sample and a "reference value." In some embodiments, the reference value is the expression level of the FOLR1 in a reference sample. A reference value may be a predetermined value and may also be determined from reference samples (e.g., control biological samples) tested in parallel with the test samples. A reference value can be a single cut-off value, such as a median or mean or a range of values, such as a confidence interval. Reference values can be established for various subgroups of individuals, such as individuals predisposed to cancer, individuals having early or late stage cancer, male and/or female individuals, or individuals undergoing cancer therapy. Examples of normal reference samples or values and positive reference samples or values are described herein.

In some embodiments, the reference sample is a sample from a healthy tissue, in particular a corresponding tissue which is not affected by cancer. These types of reference samples are referred to as negative control samples. In other embodiments, the reference sample is a sample from a tumor tissue that expresses FOLR1. These types of reference samples are referred to as positive control samples. Positive control samples can also be used as a comparative indicator for the uniformity (hetero versus homo) and/or degree (1, 2, 3, 3+) of staining intensity, which correlates with the level of FOLR1 expression. Positive control comparative samples are also referred to as calibrated reference samples which demonstrate a dynamic range of staining intensity or uniformity. As shown in Examples 1-9, non FOLR1-expressing reference samples include human esophagus tissue; low FOLR1 reference includes salivary gland (particularly the intercalated ducts) and lung (particularly respiratory epithelium) tissue; and high FOLR1-expressing tissue includes the pancreas (particularly ductal cells). For cell lines, low expressors include, but are not limited to OVCAR3 and T47D, moderate expressers include, but are not limited to SW620, IGROV-1, JEG3, and high expressers include, but are not limited to, KB and IGROV1. Particularly desirable positive high FOLR1 reference is a cell line stably or transiently transfected with Folate Receptor 1 (e.g., 300.19/FR1). Appropriate positive and negative reference levels of FOLR1 for a particular cancer, may be determined by measuring levels of FOLR1 in one or more appropriate subjects, and such reference levels may be tailored to specific populations of subjects (e.g., a reference level may be age-matched so that comparisons may be made between FOLR1 levels in samples from subjects of a certain age and reference levels for a particular disease state, phenotype, or lack thereof in a certain age group). Such reference levels may also be tailored to specific techniques that are used to measure levels of FOLR1 in biological samples (e.g., immunoassays, etc.), where the levels of FOLR1 may differ based on the specific technique that is used.

The term "primary antibody" herein refers to an antibody that binds specifically to the target protein antigen in a tissue sample. A primary antibody is generally the first antibody used in an immunohistochemical (IHC) procedure. In one embodiment, the primary antibody is the only antibody used in an IHC procedure. The term "secondary antibody" herein refers to an antibody that binds specifically to a primary antibody, thereby forming a bridge between the primary antibody and a subsequent reagent, if any. The secondary antibody is generally the second antibody used in an immunohistochemical procedure.

A "sample" or "biological sample" of the present invention is of biological origin, in specific embodiments, such as from eukaryotic organisms. In preferred embodiments, the sample is a human sample, but animal samples may also be used in the practice of the invention. Non-limiting sources of a sample for use in the present invention include solid tissue, biopsy aspirates, ascites, fluidic extracts, blood, plasma, serum, spinal fluid, lymph fluid, the external sections of the skin, respiratory, intestinal, and genitourinary tracts, tears, saliva, milk, tumors, organs, cell cultures and/or cell culture constituents, for example. The present invention is particularly useful for cancer samples which generally comprise solid tissue samples, or other bodily fluids such as ascites, where the amount of available material is small. The method can be used to examine an aspect of expression of FOLR1 or a state of a sample, including, but not limited to, comparing different types of cells or tissues, comparing different developmental stages, and detecting or determining the presence and/or type of disease or abnormality.

For the purposes herein, a "section" of a tissue sample refers to a single part or piece of a tissue sample, e.g. a thin slice of tissue or cells cut from a tissue sample. It is understood that multiple sections of tissue samples may be taken and subjected to analysis according to the present invention. In some cases, the selected portion or section of tissue comprises a homogeneous population of cells. In other cases, the selected portion comprises a region of tissue, e.g. the lumen as a non-limiting example. The selected portion can be as small as one cell or two cells, or could represent many thousands of cells, for example. In most cases, the collection of cells is important, and while the invention has been described for use in the detection of cellular components, the method may also be used for detecting non-cellular components of an organism (e.g. soluble components in the blood as a non-limiting example).

By "correlate" or "correlating" is meant comparing, in any way, the performance and/or results of a first analysis with the performance and/or results of a second analysis. For example, one may use the results of a first analysis in carrying out the second analysis and/or one may use the results of a first analysis to determine whether a second analysis should be performed and/or one may compare the results of a first analysis with the results of a second analysis. In one embodiment, increased expression of FOLR1 correlates with increased likelihood of effectiveness of a FOLR1-targeting anti-cancer therapy.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as FOLR1. In a certain embodiment blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-FOLR1 antibody" or "an antibody that binds to FOLR1" refers to an antibody that is capable of binding FOLR1 with sufficient affinity such that the antibody is useful as a diagnostic and/or therapeutic agent in targeting FOLR1. The extent of binding of an anti-FOLR1 antibody to an unrelated, non-FOLR1 protein is less than about 10% of the binding of the antibody to FOLR1 as measured, e.g., by a radioimmunoassay (RIA). In certain embodiments, an antibody that binds to FOLR1 has a dissociation constant (Kd) of ≤1 µM, ≤100 nM, ≤10 nM, ≤1 nM, or ≤0.1 nM. Examples of anti-FOLR1 antibodies are known in the art and are disclosed in US Appl. Pub. No. 2012/0009181, which is herein incorporated by reference.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristics measured by said values (e.g., Kd values). The difference between said two values is less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-FOLR1 antibody or fragment thereof) and is defined by a generic formula: C-L-A, wherein C=cytotoxin, L=linker, and A=cell binding agent or anti-FOLR1 antibody or antibody fragment. Immunoconjugates can also be defined by the generic formula in reverse order: A-L-C.

A "linker" is any chemical moiety that is capable of linking a compound, usually a drug, such as a maytansinoid, to a cell-binding agent such as an anti FOLR1 antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

"Tumor" and "neoplasm" refer to any mass of tissue that result from excessive cell growth or proliferation, either benign (noncancerous) or malignant (cancerous) including pre-cancerous lesions.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. Such formulation can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; and/or relieve to some extent one or more of the symptoms associated with the cancer. See the definition herein of "treating". To the extent the drug can prevent growth and/or kill existing cancer cells, it can be cytostatic and/or cytotoxic. In certain embodiments, identification of increased FOLR1 levels allows for administration of decreased amounts of the FOLR1-targeting therapeutic to achieve the same therapeutic effect as seen with higher dosages. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "respond favorably" generally refers to causing a beneficial state in a subject. With respect to cancer treatment, the term refers to providing a therapeutic effect on the subject. Positive therapeutic effects in cancer can be measured in a number of ways (See, W. A. Weber, J. Nucl. Med. 50:1S-10S (2009)). For example, tumor growth inhibition, molecular marker expression, serum marker expression, and molecular imaging techniques can all be used to assess therapeutic efficacy of an anti-cancer therapeutic. With respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival (PFS), overall survival (OS), each as measured by standards set by the National Cancer Institute and the U.S. Food and Drug Administration for the approval of new drugs. See Johnson et al, (2003) J. Clin. Oncol. 21(7):1404-1411.

"Progression free survival" (PFS), also referred to as or "Time to Tumor Progression" (YIP) indicates the length of time during and after treatment that the cancer does not grow. Progression-free survival includes the amount of time patients have experienced a complete response or a partial response, as well as the amount of time patients have experienced stable disease.

"Disease free survival" (DFS) refers to the length of time during and after treatment that the patient remains free of disease.

"Overall Survival" (OS) refers to a prolongation in life expectancy as compared to naive or untreated individuals or patients.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Biological Samples

Biological samples are often fixed with a fixative. Aldehyde fixatives such as formalin (formaldehyde) and glutaraldehyde are typically used. Tissue samples fixed using other fixation techniques such as alcohol immersion (Battifora and Kopinski, J. Histochem. Cytochem. (1986) 34:1095) are also suitable. The samples used may also be embedded in paraffin. In one embodiment, the tissue samples are both formalin-fixed and paraffin-embedded (FFPE). In another embodiment, the FFPE block is hematoxylin and eosin stained prior to selecting one or more portions for analysis in order to select specific area(s) for the FFPE core sample. Methods of preparing tissue blocks from these particulate specimens have been used in previous IHC studies of various prognostic factors, and/or is well known to those of skill in the art (see, for example, Abbondanzo et al., Am J Clin Pathol. 1990 May; 93(5):698-702; Allred et al., Arch Surg. 1990 January; 125(1):107-13).

Briefly, any intact organ or tissue may be cut into fairly small pieces and incubated in various fixatives (e.g. formalin, alcohol, etc.) for varying periods of time until the tissue is "fixed". The samples may be virtually any intact tissue surgically removed from the body. The samples may be cut into reasonably small piece(s) that fit on the equipment routinely used in histopathology laboratories. The size of the cut pieces typically ranges from a few millimeters to a few centimeters.

III. Detection Antibody Conjugates

The present invention further provides antibodies against FOLR1, generally of the monoclonal type, that are linked to at least one agent to form a detection antibody conjugate. In order to increase the efficacy of antibody molecules as diagnostic it is conventional to link or covalently bind or complex at least one desired molecule or moiety. Such a molecule or moiety may be, but is not limited to, at least one reporter molecule. A reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles and/or ligands, such as biotin.

Any cell binding agent (e.g., an antibody or polypeptide) of sufficient selectivity, specificity or affinity may be employed as the basis for detection of the FOLR1 polypeptide. Such properties may be evaluated using conventional immunological screening methodology known to those of skill in the art. Sites for binding to biological active molecules in the antibody molecule, in addition to the canonical antigen binding sites, include sites that reside in the variable domain that can bind the antigen. In addition, the variable domain is involved in antibody self-binding (Kang et al., 1988) and contains epitopes (idiotopes) recognized by anti-antibodies (Kohler et al., 1989).

Certain examples of protein binding (e.g., antibody) conjugates are those conjugates in which the protein binding agent (e.g., antibody) is linked to a detectable label. "Detectable labels" are compounds and/or elements that can be detected due to their specific functional properties, and/or chemical characteristics, the use of which allows the antibody to which they are attached to be detected, and/or further quantified if desired.

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; and/or X-ray imaging, for example.

Exemplary fluorescent labels contemplated for use as protein binding (e.g., antibody) conjugates include Alexa 350, Alexa 430, Alexa 488, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Dylight 488, Fluorescein Isothiocyanate, Green fluorescent protein (GFP), HEX, 6-JOE, Oregon Green 488, Oregon Green 500, Oregon Green 514, Pacific Blue, Phycoerythrin, REG, Rhodamine Green, Rhodamine Red, tetramethyl rhodamine (TMR), Renographin, ROX, TAMRA, TET, Tetramethylrhodamine, Texas Red, and derivatives of these labels (i.e halogenated analogues, modified with isothiocyanate or other linker for conjugating, etc), for example. An exemplary radiolabel is tritium.

Protein binding (e.g., antibody) detection conjugates contemplated in the present invention include those for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase and/or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Protein binding (e.g., antibody) conjugates with fluorescein markers are prepared in the presence of these coupling agents or by reaction with an isothiocyanate. In U.S. Pat. No. 4,938,948, imaging of breast tumors, for example, is achieved using monoclonal antibodies, and the detectable imaging moieties are bound to the antibody using linkers such as methyl-p-hydroxybenzimidate or N-succinimidyl-3-(4-hydroxyphenyl)-propionate.

In other embodiments, derivatization of immunoglobulins by selectively introducing sulfhydryl groups in the Fc region of an immunoglobulin using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region, have also been disclosed in the literature (O'Shannessy et al., 1987).

In other embodiments of the invention, immunoglobulins are radiolabeled with nuclides such as tritium. In additional embodiments, nanogold particles (such as sizes from about 0.5 nm-40 nm) and/or Quantum Dots (Hayward, Calif.) are employed.

IV. Enzymes and Substrates (Chromagens)

The use of substrates and indicators is contemplated for detection of FOLR1, such as the exemplary embodiments provided below, for example.

Horseradish peroxidase (HRP) is an enzyme that first forms a complex with hydrogen peroxide and then causes it to decompose, resulting in water and atomic oxygen. Like many other enzymes, HRP and some HRP-like activities can be inhibited by excess substrate. The complex formed between HRP and excess hydrogen peroxide is catalytically inactive and in the absence of an electron donor (e.g. chromogenic substance) is reversibly inhibited. It is the excess hydrogen peroxide and the absence of an electron donor that brings about quenching of endogenous HRP activities.

When used in assays systems, HRP can also be used to convert a defined substrate into its activated chromagen, thus causing a color change. The HRP enzyme may be conjugated to an antibody, protein, peptide, polymer, or other molecule by a number of methods. Such methods are known in the art. Adding glutaraldehyde to a solution containing an admixture of HRP and antibody will result in more antibody molecules being conjugated to each other than to the enzyme. In the two-step procedure, HRP reacts with the bifunctional reagents first. In the second stage, only activated HRP is admixed with the antibody, resulting in much more efficient labelling and no polymerization. HRP is also conjugated to (strept)avidin using the two-step glutaraldehyde procedure. This form is used in procedures where LAB and LSAB are substrate, for example. Conjugation with biotin also involves two steps, as biotin must first be derivatized to the biotinyl-N-hydroxysuccinimide ester or to biotin hydrazide before it can be reacted with the epsilonamino groups of the HRP enzyme.

3,3'-Diaminobenzidine (DAB) is a substrate for enzymes such as HRP that produces a brown end product that is highly insoluble in alcohol and other organic solvents. Oxidation of DAB also causes polymerization, resulting in the ability to react with osmium tetroxide, and thus increasing its staining intensity and electron density. Of the several metals and methods used to intensify the optical density of polymerized DAB, gold chloride in combination with silver sulfide appears to be the most successful.

3-Amino-9-ethylcarbazole (AEC) is a substrate for enzymes such as HRP. Upon oxidation, forms a rose-red end product that is alcohol soluble. Therefore, specimens processed with AEC must not be immersed in alcohol or alcoholic solutions (e.g., Harris' hematoxylin). Instead, an aqueous counterstain and mounting medium should be used. AEC is unfortunately susceptible to further oxidation and, when exposed to excessive light, will fade in intensity. Storage in the dark is therefore recommended.

4-Chloro-1-naphthol (CN) is a substrate for enzymes such as HRP and precipitates as a blue end product. Because CN is soluble in alcohol and other organic solvents, the specimen must not be dehydrated, exposed to alcoholic counterstains, or coverslipped with mounting media containing organic solvents. Unlike DAB, CN tends to diffuse from the site of precipitation.

p-Phenylenediamine dihydrochloride/pyrocatechol (Hanker-Yates reagent) is a an electron donor substrate for enzymes such as HRP and gives a blue-black reaction product that is insoluble in alcohol and other organic solvents. Like polymerized DAB, this reaction product can be osmicated. Varying results have been achieved with Hanker-Yates reagent in immunoperoxidase techniques.

Calf intestine alkaline phosphatase (AP) (molecular weight 100 kD) is an enzyme that removes (by hydrolysis) and transfers phosphate groups from organic esters by breaking the P-0 bond; an intermediate enzyme-substrate bond is briefly formed. The chief metal activators for AP are $Mg^{++}$, $Mn^{++}$ and $Ca^{++}$.

AP had not been used extensively in immunohistochemistry until publication of the unlabeled alkaline phosphatase-antialkaline phosphatase (APAAP) procedure. The soluble immune complexes utilized in this procedure have molecular weights of approximately 560 kD. The major advantage of the APAAP procedure compared to the PAP technique is the lack of interference posed by endogenous peroxidase activity. Because of the potential distraction of endogenous peroxidase activity on PAP staining, the APAAP technique is recommended for use on blood and bone marrow smears. Endogenous alkaline phosphatase activity from bone, kidney, liver and some white cells can be inhibited by the addition of 1 mM levamisole to the substrate solution, although 5 mM has been found to be more effective. Intestinal alkaline phosphatases are not adequately inhibited by levamisole.

In the immunoalkaline phosphatase staining method, the enzyme hydrolyzes naphthol phosphate esters (substrate) to phenolic compounds and phosphates. The phenols couple to colorless diazonium salts (chromogen) to produce insoluble, colored azo dyes. Several different combinations of substrates and chromogens have been used successfully.

Naphthol AS-MX phosphate can be used in its acid form or as the sodium salt. The chromogens Fast Red TR and Fast Blue BB produce a bright red or blue end product, respectively. Both are soluble in alcoholic and other organic solvents, so aqueous mounting media must be used. Fast Red TR is preferred when staining cell smears.

Additional exemplary substrates include naphthol AS-BI phosphate, naphthol AS-TR phosphate and 5-bromo-4-chloro-3-indoxyl phosphate (BCIP). Other possible chromogens include Fast Red LB, Fast Garnet GBC, Nitro Blue Tetrazolium (NBT) iodonitrotetrazolium Violet (INT), and derivatives of the structures, for example.

V. Immunodetection Methods

In still further embodiments, the present invention concerns immunodetection methods for binding, purifying, removing, quantifying and/or otherwise generally detecting biological components such as a ligand as contemplated by the present invention. The antibodies prepared in accordance with the present invention may be employed to detect wild-type and/or mutant ligand proteins, polypeptides and/or peptides. As described throughout the present application, the use of wild-type and/or mutant ligand specific antibodies is contemplated. Some immunodetection methods include flow cytometry, enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, Methods Mol Biol. 1999; 109:215-37; Gulbis B and Galand P, Hum Pathol. 1993 December; 24(12):1271-85; and De Jager R et al., Semin Nucl Med. 1993 April; 23(2):165-79, each incorporated herein by reference.

In general, the immunobinding methods include obtaining a sample suspected of comprising ligand protein, polypeptide and/or peptide, and contacting the sample with a first ligand binding peptide (e.g., an anti-ligand antibody) in accordance with the present invention, as the case may be, under conditions effective to allow the formation of immunocomplexes.

In terms of antigen detection, the biological sample analyzed may be any sample that is suspected of comprising a wild-type or mutant ligand protein-specific antigen, such as a tissue section or specimen, a homogenized tissue extract, biopsy aspirates, a cell, separated and/or purified forms of any of the above wild-type or mutant FOLR1-containing compositions, or even any biological fluid that comes into contact with the tissue, including blood and/or serum, although tissue samples or extracts are preferred.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any ligand protein antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The anti-ligand antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding agent that has binding affinity for the antibody. In these cases, the second binding agent may be linked to a detectable label. The second binding agent is itself often an antibody, which may thus be termed a "secondary" antibody, or a polymer detection system. The primary immune complexes are contacted with the labeled, secondary binding agent, or antibody/polymer detection system, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding agent, such as an antibody, that has binding affinity for the antibody is used to form secondary immune complexes, as described above. After washing, the secondary immune complexes are contacted with a third binding agent or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

In another embodiment, a biotinylated monoclonal or polyclonal antibody is used to detect the target antigen(s), and a second step antibody is then used to detect the biotin attached to the complexed biotin. In that method the sample to be tested is first incubated in a solution comprising the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution comprising the second step antibody against biotin. This second step antibody is labeled, as for example with an enzyme that can be used to detect the presence of the antibody/antigen complex by histoenzymology using a chromogen substrate. With suitable amplification, a protein binding (e.g., antibody) conjugate can be produced that is macroscopically visible.

Another known method of immunodetection takes advantage of the immuno-PCR (Polymerase Chain Reaction) methodology. The PCR method uses a DNA/biotin/streptavidin/antibody complex that is washed out with a low pH or high salt buffer that releases the antibody. The resulting wash solution is then used to carry out a PCR reaction with suitable primers with appropriate controls. In specific embodiments, the enormous amplification capability and specificity of PCR can be utilized to detect a single antigen molecule. Such detection may take place in real-time. For example, the use of quantitative real-time PCR is contemplated.

In the clinical diagnosis and/or monitoring of patients with various forms of disease, the detection of a FOLR1 mutant, and/or an alteration in the levels of FOLR1, in comparison to the levels in a corresponding biological sample from a normal subject is indicative of a patient with the disease. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive.

In one embodiment, immunological detection (by immunohistochemistry) of FOLR1 is scored for both intensity and uniformity (percent of stained cells—membrane only). Comparative scales for FOLR1 expression for intensity correlate as 0—Negative, 0-1—Very Weak, 1—Weak, 1-2—Weak to Moderate, 2—Moderate, 2-3—Moderate to Strong, 3—Strong. Quantitatively, Score 0 represents that no membrane staining is observed in tumor cells. A Score 1 represents a faint/barely perceptible membrane staining in tumor cells. For Score 2, a moderate membrane staining is observed in tumor cells. Lastly, Score 3 or 3+ represents a moderate to strong membrane staining in the tumor cells. Those samples with 0 or 1 score for FOLR1 expression may be characterized as not overexpressing FOLR1, whereas those samples with 2 or 3 scores may be characterized as overexpressing FOLR1. Samples overexpressing FOLR1 may also be rated by immunohistochemical scores corresponding to the number of copies of FOLR1 molecules expressed per cell, and have been determined biochemically: 0=0-10,000 copies/cell, 1=at least about 200,000 copies/cell, 2=at least about 500,000 copies/cell, and 3=at least about 2,000,000 copies/cell. Comparative scales for FOLR1 percent cell membrane staining uniformity correlate as follows: 0—Negative, Focal—<25%, heterogeneous (hetero)—25-75%, and homogeneous (homo)—>75%.

VI. Nucleic Acid Hybridization

In situ hybridization is generally carried out on cells or tissue sections fixed to slides. In situ hybridization may be performed by several conventional methodologies (See for e.g. Leitch et al. In situ Hybridization: a practical guide, Oxford BIOS Scientific Publishers, Microscopy handbooks v. 27 (1994)). In one in situ procedure, fluorescent dyes (such as fluorescein isothiocyanate (FITC) that fluoresces green when excited by an Argon ion laser) are used to label a nucleic acid sequence probe that is complementary to a target nucleotide sequence in the cell. Each cell comprising the target nucleotide sequence will bind the labeled probe, producing a fluorescent signal upon exposure of the cells to a light source of a wavelength appropriate for excitation of the specific fluorochrome used.

Various degrees of hybridization stringency can be employed. As the hybridization conditions become more stringent, a greater degree of complementarity is required between the probe and target to form and maintain a stable duplex. Stringency is increased by raising temperature, lowering salt concentration, or raising formamide concentration. Adding dextran sulfate or raising its concentration may also increase the effective concentration of labeled probe to increase the rate of hybridization and ultimate signal intensity. After hybridization, slides are washed in a solution generally comprising reagents similar to those found in the hybridization solution with washing time varying from minutes to hours depending on required stringency. Longer or more stringent washes typically lower nonspecific background but run the risk of decreasing overall sensitivity.

Probes used in nucleic hybridization analysis may be either RNA or DNA oligonucleotides or polynucleotides and may contain not only naturally-occurring nucleotides but their analogs, like digoxygenin dCTP, biotin dcTP 7-azaguanosine, azidothymidine, inosine, or uridine, for example. Other useful probes include peptide probes and analogues thereof, branched gene DNA, peptidometics, peptide nucleic acid (PNA) and/or antibodies, for example.

Probes should have sufficient complementarity to the target nucleic acid sequence of interest so that stable and specific binding occurs between the target nucleic acid sequence and the probe. The degree of homology required for stable hybridization varies with the stringency of the hybridization medium and/or wash medium. Preferably, completely homologous probes are employed in the present invention, but persons of skill in the art will readily appreciate that probes exhibiting lesser but sufficient homology can be used in the present invention (see for e.g. Sambrook, J., Fritsch, E. F., Maniatis, T., Molecular Cloning A Laboratory Manual, Cold Spring Harbor Press, (1989)).

Probes may also be generated and chosen by several means including, but not limited to, mapping by in situ hybridization, somatic cell hybrid panels, or spot blots of sorted chromosomes; chromosomal linkage analysis; or cloned and isolated from sorted chromosome libraries from human cell lines or somatic cell hybrids with human chromosomes, radiation somatic cell hybrids, microdissection of a chromosome region, or from yeast artificial chromosomes (YACs) identified by PCR primers specific for a unique chromosome locus or other suitable means like an adjacent YAC clone. Probes may be genomic DNA, cDNA, or RNA cloned in a plasmid, phage, cosmid, YAC, Bacterial Artificial Chromosomes (BACs), viral vector, or any other suitable vector. Probes may be cloned or synthesized chemically by conventional methods. When cloned, the isolated probe nucleic acid fragments are typically inserted into a vector, such as lambda phage, pBR322, M13, or vectors containing the SP6 or T7 promoter and cloned as a library in a bacterial host. [See for e.g. Sambrook, J., Fritsch, E. F., Maniatis, T., Molecular Cloning A Laboratory Manual, Cold Spring Harbor Press, (1989)].

Probes are preferably labeled, such as with a fluorophor, for example. Examples of fluorophores include, but are not limited to, rare earth chelates (europium chelates), Texas Red, rhodamine, fluorescein, dansyl, Lissamine, umbelliferone, phycocrytherin, phycocyanin, or commercially available fluorophors such SPECTRUM ORANGE™ and SPECTRUM GREEN™ and/or derivatives of any one or more of the above. Multiple probes used in the assay may be labeled with more than one distinguishable fluorescent or pigment color. These color differences provide a means to identify the hybridization positions of specific probes. Moreover, probes that are not separated spatially can be identified by a different color light or pigment resulting from mixing two other colors (e.g., light red+green=yellow) pigment (e.g., blue+yellow=green) or by using a filter set that passes only one color at a time.

Probes can be labeled directly or indirectly with the fluorophor, utilizing conventional methodology known to one with skill in the art.

VII. Detection Kits and Compositions

Also provided by the invention are kits for use in the practice of the present invention as disclosed herein. Such kits may comprise containers, each with one or more of the various reagents (typically in concentrated form) utilized in the methods, including, for example, one or more binding agents (antibodies), already attached to a marker or optionally with reagents for coupling a binding agent to an antibody or nucleic acid molecule (as well as the marker itself); buffers, the appropriate nucleotide triphosphates (e.g. dATP, dCTP, dGTP, dTTP, dUTP, ATP, CTP, GTP and UTP), reverse transcriptase, DNA polymerase, RNA polymerase, and one or more sequence-specific or degenerate primers for use in detection of nucleic acid molecules by amplification; and/or reagents and instrumentation for the isolation (optionally by microdissection) to support the practice of the invention. A label or indicator describing, or a set of instructions for use of, kit components in a ligand detection method of the present invention, will also be typically included, where the instructions may be associated with a package insert and/or the packaging of the kit or the components thereof.

In still further embodiments, the present invention concerns immunodetection kits for use with the immunodetection methods described above. As the antibodies are generally used to detect wild-type and/or mutant proteins, polypeptides and/or peptides, the antibodies will preferably be included in the kit. The immunodetection kits will thus comprise, in suitable container means, a first antibody that binds to a wild-type and/or mutant protein, polypeptide and/or peptide, and/or optionally, an immunodetection reagent and/or further optionally, a wild-type and/or mutant protein, polypeptide and/or peptide.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies or polymers that have binding affinity for the first antibody.

Further suitable immunodetection reagents for use in the present kits include the two-component reagent that comprises a secondary antibody that has binding affinity for the first antibody, along with a third antibody or polymer that has binding affinity for the second antibody, the third antibody being linked to a detectable label. As noted above, a number of exemplary labels are known in the art and/or all such labels may be suitably employed in connection with the present invention.

The kits may further comprise a suitably aliquoted composition of the wild-type and/or mutant protein, polypeptide and/or polypeptide, whether labeled and/or unlabeled, as may be used to prepare a standard curve for a detection assay. The kits may contain antibody- or polymer-label conjugates either in fully conjugated form, in the form of intermediates, and/or as separate moieties to be conjugated by the user of the kit. The components of the kits may be packaged either in aqueous media and/or in lyophilized form.

The container means of the kits will generally include at least one vial, test tube, flask, bottle, syringe and/or other container means, into which the antibody may be placed, and/or preferably, suitably aliquoted. The kits of the present invention will also typically include a means for containing the antibody, antigen, and/or any other reagent containers in close confinement for commercial sale. Such containers may include injection and/or blow-molded plastic containers into which the desired vials are retained.

The kits may further comprise one or more therapeutic agents for the treatment of cancer, such as a FOLR1 immunoconjugate and/or a chemotherapeutic agent.

The kit may further comprise an a FOLR1 detection reagent used to measure FOLR1 expression in a subject comprising a FOLR1 detection reagent, and instructions for use. In one embodiment, the FOLR1 detection reagent comprises a FOLR1 binding peptide, protein or a molecular probe (i.e. nucleic acid). In another embodiment, the FOLR1 detection reagent is an anti-FOLR1 antibody. In another embodiment, the kit further comprises a secondary antibody which binds the anti-FOLR1 antibody. In one embodiment the FOLR1-specific antibody is included at a concentration of 0.5 to 7.5 µg/ml, preferably 0.9 to 3.8+/−0.5 µg/ml. In another embodiment, the antibody is included at a concentration of 1.0+/−0.5 µg/ml, 1.5+/−0.5 µg/ml, 1.9+/−0.5 µg/ml, 2.5+/−0.5 µg/ml, 3.0+/−0.5 µg/ml, 3.5+/−0.5 µg/ml, 3.8+/−0.5 µg/ml, or up to 4.2 µg/ml. In another embodiment, the antibody is included in concentrated solution with instructions for dilutions to achieve a final concentration of 0.9 to 3.8+/−0.5 µg/ml. In another embodiment, the kit further comprises a detection reagent selected from the group consisting of: an enzyme, a fluorophore, a radioactive label, and a luminophore. In another embodiment, the detection reagent is selected from the group consisting of: biotin, digoxigenin, fluorescein, tritium, and rhodamine.

The kit can also include instructions for detection and scoring of FOLR1 expression. The kit can also include control or reference samples. Non-limiting examples of control or reference samples include cell pellets or tissue culture cell lines derived from normal (normal control) or tumor (positive control) samples. Exemplary cell lines include KB, NCI-H2110, Igrov-1, Ishikawa, Jeg-3, Skov-3, Hela, T47D, Caco2, SW620, OAW28, HCC827, Ovcar-8, and Ovcar-3, Ov-90, other tumor cell lines known to express FOLR1, and cell lines stably or transiently transfected with an expression vector that expresses FOLR1. Additional examples for positive control tissues can also be found in Examples 9-11. The kit can also comprise a staining guide which visually depicts positive and normal reference samples for staining intensity and uniformity. Such staining guides can have reference samples from normal lung, pancreas, and/or salivary gland, and stained tumors with standardized scores (e.g., ovarian, lung, renal, and endometrial cancers, as well as those described in the Examples and in FIGS. 23-25)

VIII. FOLR1-Binding Agents

Any antibodies that bind FOLR1 can be used in the detection methods of the present invention. Examples of therapeutically effective anti-FOLR1 antibodies can be found in US Appl. Pub. No. US 2012/0009181 which is herein incorporated by reference. The full-length amino acid (aa) and nucleotide (nt) sequences for FOLR1 are known in the art and also provided herein as represented by SEQ ID NOs: 1 and 2, respectively. A specifically useful antibody for detection of FOLR1 is the mouse monoclonal anti-huFOLR1 clone BN3.2 (Leica #NCL-L-FRalpha). An example of a therapeutically effective anti-FOLR1 antibody is huMov19 (M9346A). The polypeptides of SEQ ID NOs: 3-5 comprise the variable domain of the heavy chain of huMov19 (M9346A), and the variable domain light chain version 1.00, the variable domain light chain version 1.60 of huMov19, respectively. The huMov19 (M9346A) antibody comprises: (a) a heavy chain CDR1 comprising GYFMN (SEQ ID NO:6); a heavy chain CDR2 comprising RIHPYDGDTFYNQKFQG (SEQ ID NO:7); and a heavy chain CDR3 comprising YDGSRAMDY (SEQ ID NO:8); and (b) a light chain CDR1 comprising KASQSVSFAGTSLMH (SEQ ID NO:9); a light chain CDR2 comprising RASNLEA (SEQ ID NO:10); and a light chain CDR3 comprising QQSREYPYT (SEQ ID NO:11). In certain embodiments, the huMov19 (M9346A) antibody is encoded by the plasmids deposited with the American Type Culture Collection (ATCC), located at 10801 University Boulevard, Manassas, Va. 20110 on Apr. 7, 2010 under the terms of the Budapest Treaty and having ATCC deposit nos. PTA-10772 and PTA-10773 or 10774. Examples of FOLR1 immunoconjugates useful in the therapeutic methods of the invention are provided below.

IX. FOLR1 Immunoconjugates

The present invention also includes methods for increasing the efficacy of conjugates (also referred to herein as immunoconjugates), comprising the anti-FOLR1 antibodies, antibody fragments, functional equivalents, improved antibodies and their aspects as disclosed herein, linked or conjugated to a cytotoxin (drug) or prodrug. Exemplary FOLR1 immunoconjugates can be found in US Appl. Pub. No. US 2012/0009181, which is herein incorporated by reference. A particularly effective therapeutic immunoconjugate of the invention comprises the huMov19 antibody described above.

Suitable drugs or prodrugs are known in the art. In certain embodiments, drugs or prodrugs are cytotoxic agents. The cytotoxic agent used in the cytotoxic conjugate of the present invention can be any compound that results in the death of a cell, or induces cell death, or in some manner decreases cell viability, and includes, for example, maytansinoids and maytansinoid analogs, benzodiazepines, taxoids, CC-1065 and CC-1065 analogs, duocarmycins and duocarmycin analogs, enediynes, such as calicheamicins, dolastatin and dolastatin analogs including auristatins, tomaymycin derivaties, leptomycin derivaties, methotrexate, cisplatin, carboplatin, daunorubicin, doxorubicin, vincristine, vinblastine, melphalan, mitomycin C, chlorambucil and morpholino doxorubicin. In certain embodiments, the cytotoxic agents are maytansinoids and maytansinoids analogs.

The drug or prodrug can, for example, be linked to the anti-FOLR1 antibody, such as huMov19, or fragment thereof through a disulfide bond. The linker molecule or crosslinking agent comprises a reactive chemical group that can react with the anti-FOLR1 antibody or fragment thereof. In certain embodiments, reactive chemical groups for reaction with the cell-binding agent are N-succinimidyl esters and N-sulfosuccinimidyl esters. Additionally the linker molecule comprises a reactive chemical group, in certain embodiments a dithiopyridyl group that can react with the drug to form a disulfide bond. In certain embodiments, linker molecules include, for example, N-succinimidyl 3-(2-pyridyldithio) propionate (SPDP) (see, e.g., Carlsson et al., Biochem. J., 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)2-sulfobutanoate (sulfo-SPDB) (see US Publication No. 20090274713), N-succinimidyl 4-(2-pyridyldithio) pentanoate (SPP) (see, e.g., CAS Registry number 341498-08-6), 2-iminothiolane, or acetylsuccinic anhydride.

Antibody-maytansinoid conjugates with non-cleavable links can also be prepared. Such crosslinkers are described in the art (see ThermoScientific Pierce Crosslinking Technical Handbook and US Patent Application Publication No. 2005/0169933) and include but are not limited to, N-succinimidyl 4-(maleimidomethyl) cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), β-maleimidopropanoic acid N-succinimidyl ester (BMPS), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), and N-(p-maleimidophenyl)isocyanate (PMPI), N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP). In certain embodiments, the antibody is modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)).

The present invention includes aspects wherein about 2 to about 8 drug molecules ("drug load"), for example, maytansinoid, are linked to an anti-FOLR1 antibody or fragment thereof, the anti-tumor effect of the conjugate is much more efficacious as compared to a drug load of a lesser or higher number of drugs linked to the same cell binding agent. "Drug load", as used herein, refers to the number of drug molecules (e.g., a maytansinoid) that can be attached to a cell binding agent (e.g., an anti-FOLR1 antibody or fragment thereof). In one aspect the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). In certain embodiments, the drug is $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl) maytansine (DM4). Thus, in a certain embodiment, the antibody huMov19 is conjugated to DM1 or DM4. In another embodiment, the antibody FR-1-21 is conjugated to DM1 or DM4. In another embodiment, the antibody FR-1-48 is conjugated to DM1 or DM4. In another embodiment, the antibody FR-1-49 is conjugated to DM1 or DM4. In another embodiment, the antibody FR-1-57 is conjugated to DM1 or DM4. In another embodiment, the antibody FR-1-65 is conjugated to DM1 or DM4.

X. Correlation of FOLR1 Expression and Therapeutic Efficacy

In certain embodiments, the invention provides a method for identifying subjects with an increased likelihood for responding to FOLR1-targeting anti-cancer therapies. The invention is based, in part, on the discovery that elevated FOLR1 expression levels correlates with efficacy of FOLR-1-targeting anti-cancer therapeutics.

Evaluation of patient samples and correlation to in vivo efficacy using xenograft models demonstrates the power of the expression analysis for selecting subjects more likely to respond to treatment. IHC provides a score for FOLR1 expression on tumor cells: 0 (no expression) to 3+ (very high levels of expression). In vivo data using xenograft models demonstrates that samples scoring 1, 2, 3, or 3+ for FOLR1 expression, preferably a score of 2, 3, or 3+, have an increased likelihood to respond to FOLR-1-targeted anti-cancer therapies at clinically-relevant doses of FOLR1 immunoconjugates (e.g., 5 mg/kg xenograft dose of a FOLR1 immunoconjugate can approximate a 185 mg/m$^2$ in patients). Thus, identification of individuals having an elevated FOLR1 score would help identify those individuals who might respond to a clinically relevant dosage. As described in more detail below, sensitivity to FOLR1 therapeutics correlated with FOLR1 scoring of 2 or higher, especially with level 3 scoring. Moreover, expression of more uniform levels of FOLR1 provides better correlation with therapeutic benefit. Thus, a homogeneous staining uniformity is preferred but combinations of increased staining intensity with heterogeneous staining uniformity are also indicative of increased FOLR1 expression. For example, scores of greater than 2 hetero is a patient selection criterion for treatment with a FOLR1 therapeutic agent.

FOLR1 expression analysis also identifies patients in whom decreased levels of a FOLR1-targeting anti-cancer therapy ("low dose therapy") can be effective to cause anti-tumor responses. As is appreciated in the art, compounds are generally administered at the smallest dosage that achieves the desired therapeutic response. This is specifically important for therapeutics that cause clinical, and often undesired, side effects. The ability to recognize those subjects with elevated FOLR1 expression levels allows for minimization of the dosage of the FOLR-1-targeting therapeutic, thus decreasing possible side effects, while maintaining therapeutic efficacy.

As shown herein, FOLR1 expression scores of 2 hetero or greater correlate with increased responsiveness to anti-FOLR1 immunoconjugates. In certain embodiments, the increased responsiveness is cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival (PFS), or overall survival (OS). In certain embodiments, FOLR1 expression scores of 2 hetero or greater correlate with increasing PFS, DFS, or OS.

Kits for use in the detection methods and correlation to reference/control samples can comprise control (positive and/or negative) or reference samples. The positive control or positive reference samples can be derived from tissue culture cell lines, normal tissue or tumor tissue. Positive and negative reference samples can be derived from cell lines including SW620, T47D, IGROV-1, HeLa, KB, JEG-3, other tumor cell lines, and cell lines stably or transiently transfected with an expression vector that encodes FOLR1. Normal or tumor tissue samples and tissue culture cell lines can also be used as a negative control reference samples. For additional samples, see Examples 9-11 and FIGS. 23-25.

XI. Pharmaceutical Compositions and Therapeutic Methods

FOLR1-binding agents (including antibodies, immunoconjugates, and polypeptides) are useful in a variety of applications including, but not limited to, therapeutic treatment methods, such as the treatment of cancer. In certain embodiments, the agents are useful for inhibiting tumor growth, inducing differentiation, reducing tumor volume, and/or reducing the tumorigenicity of a tumor. The methods of use may be in vitro, ex vivo, or in vivo methods. In certain embodiments, the FOLR1-binding agent or antibody or immunoconjugate, or polypeptide is an antagonist of the human FOLR1 to which it binds.

In certain embodiments, the disease treated with the FOLR1-binding agent or antagonist (e.g., a huMov19 antibody or immunoconjugate) is a cancer. In certain embodiments, the cancer is characterized by tumors expressing folate receptor 1 to which the FOLR1-binding agent (e.g., antibody) binds.

The present invention provides for methods of treating cancer comprising administering a therapeutically effective amount of a FOLR1-binding agent to a subject (e.g., a subject in need of treatment). In certain embodiments, the cancer is a cancer selected from the group consisting of colorectal cancer, pancreatic cancer, lung cancer, ovarian cancer, liver cancer, breast cancer, brain cancer, kidney cancer, prostate cancer, gastrointestinal cancer, melanoma, cervical cancer, bladder cancer, glioblastoma, and head and neck cancer. In certain embodiments, the cancer is ovarian cancer. In certain embodiments, the cancer is lung cancer. In certain embodiments, the subject is a human.

The present invention further provides methods for inhibiting tumor growth using the antibodies or other agents described herein. In certain embodiments, the method of inhibiting the tumor growth comprises contacting the cell with a FOLR1-binding agent (e.g., antibody) in vitro. For example, an immortalized cell line or a cancer cell line that expresses FOLR1 is cultured in medium to which is added the antibody or other agent to inhibit tumor growth. In some embodiments, tumor cells are isolated from a patient sample such as, for example, a tissue biopsy, pleural effusion, or blood sample and cultured in medium to which is added an FOLR1-binding agent to inhibit tumor growth.

In some embodiments, the method of inhibiting tumor growth comprises contacting the tumor or tumor cells with the FOLR1-binding agent (e.g., antibody) in vivo. In certain embodiments, contacting a tumor or tumor cell with a FOLR1-binding agent is undertaken in an animal model. For example, FOLR1-binding agents can be administered to xenografts expressing one or more FOLR1s that have been grown in immunocompromised mice (e.g. NOD/SCID mice) to inhibit tumor growth. In some embodiments, the FOLR1-binding agent is administered at the same time or shortly after introduction of tumorigenic cells into the animal to prevent tumor growth. In some embodiments, the FOLR1-binding agent is administered as a therapeutic after the tumorigenic cells have grown to a specified size.

In certain embodiments, the method of inhibiting tumor growth comprises administering to a subject an therapeutically effective amount of a FOLR1-binding agent. In certain embodiments, the subject is a human. In certain embodiments, the subject has a tumor or has had a tumor removed.

In certain embodiments, the tumor is a tumor selected from the group consisting of brain tumor, colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is an ovarian tumor.

In certain embodiments, the invention provides methods of inhibiting tumor growth using low doses of a FOLR1-binding agent. The term "low dose" as used herein refers to the therapeutically effective dose of a FOLR1-binding agent which is less than the usual or the conventional dose required to produce the therapeutic effect.

Thus, in certain embodiments the inventions provides methods of treating cancer using huMov19 antibody and immunoconjugates. In certain embodiments, the huMov19 immunoconjugate is huMov19-SPDB-DM4; huMov19-sulfo-SPP-DM1; huMov19-SPP-DM1; or huMov19-PEG4-Mal-DM4. In a certain embodiment, the huMov19 immunconjuage is huMov19-SPDB-DM4, which is also referred to as IMGN853.

In certain embodiments, formulations are prepared for storage and use by combining a purified antibody or agent of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical compositions of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

An antibody or immunoconjugate of the invention can be combined in a pharmaceutical combination formulation, or dosing regimen as combination therapy, with a second compound having anti-cancer properties. The second compound of the pharmaceutical combination formulation or dosing regimen preferably has complementary activities to the ADC of the combination such that they do not adversely affect each other. Pharmaceutical compositions comprising the FOLR1-binding agent and the second anti-cancer agent are also provided.

For the treatment of the disease, the appropriate dosage of an antibody or agent of the present invention depends on the type of disease to be treated, the severity and course of the disease, the responsiveness of the disease, whether the antibody or agent is administered for therapeutic or preventative purposes, previous therapy, patient's clinical history, and so on all at the discretion of the treating physician. The antibody or agent can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody or agent. The administering physician can easily determine optimum dosages, dosing methodologies and repetition rates. In certain embodiments, dosage is from 0.01 µg to 100 mg per kg of body weight, and can be given once or more daily, weekly, monthly or yearly. In certain embodiments, the antibody or other FOLR1-binding agent is given once every two weeks or once every three weeks. In certain embodiments, the dosage of the antibody or other FOLR1-binding agent is from about 0.1 mg to about 20 mg per kg of body weight. The treating physician can estimate repetition rates for dosing based on measured residence times and concentrations of the drug in bodily fluids or tissues.

The combination therapy can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

The Folate Receptor-1 (FOLR1) has been reported to be highly expressed in ovarian tumors and expressed at high to moderate levels in brain, breast, bladder, endometrioid, lung, pancreatic, and renal carcinomas. However, the expression of FOLR1 is limited in normal tissues and includes kidney, lung, choroid plexus, pancreas, breast, thyroid, ovary, prostate, and lung.

Methods have been reported that quantify FOLR1 using fresh frozen tissue homogenates. Whole tissue homogenates cannot distinguish cytoplasmic from membrane-associated expression and freshly frozen samples are not amenable in the clinical setting. However, formalin fixed paraffin embedded (FFPE) samples can be archived for patients in the clinic.

Example 1

Immunohistochemical staining of FOLR1 in cell samples—manual methods Formalin fixed paraffin embedded cell pellets and tissues were used as test samples with the following staining reagents and conditions.

| IHC Antibodies |
| --- |
| Test Article |
| mouse monoclonal anti-huFOLR1 clone BN3.2 (Leica # NCL-L-FRalpha) ImmunoGen: Prokaryotic recombinant protein corresponding to 189 amino acids of the external domain of the folate receptor alpha molecule |
| Control Article |
| muIgG1 (Coulter) Clone, Cat# 6602872 |
| Secondary Antibody |
| Biotinylated horse anti-mouse (Vector, Cat# PK-6100) |

| FFPE assay conditions | |
| --- | --- |
| Steps | Condition |
| Antigen Retrieval | Borg (Biocare) pH 9.0 |
| Blocking Steps | Avidin/Biotin; peroxide |
| Test or Control Article | 2.0 µg/mL |
| Diluent | PBS containing 2% horse serum |
| Secondary Antibody | 10 µg/mL |
| Detection System* | Avidin-Biotin-peroxidase-Complex; ABC (Vector Labs) |
| Chromagen | DAB (Dako) |
| DAB development time | ≥5 min |

Formalin-fixed paraffin-embedded (FFPE) patient ovarian tumor biopsies and ovarian xenograft tumors were stained with the murine anti-FOLR1 antibody clone BN3.2, (Leica, Cat #NC1-L-FRalpha) and a control muIgG1 from Coulter. Following antigen retrieval in pH 9.5 buffer, slides were blocked with 2% horse serum plus avidin. Slides were washed in PBS, and incubated at room temperature for 60 minutes with the anti-FOLR1 or control muIgG1 antibody, followed by 30 minutes with biotinylated anti-mouse IgG and 40 minutes with avidin-biotin-peroxidase complex to detect bound secondary antibody. Incubation for 5 minutes with DAB (3,3-diaminobenzidine tetrahydrochloride) resulted in the color signal. Slides were counterstained with hematoxylin.

FOLR1 staining intensity and distribution patterns were scored relative to control IgG staining (non-specific). Intensity was scored on a scale of 0 to 3 (0=no staining, 1=weak, 2=moderate and 3=strong) and distribution was scored as focal (<25% of cells stained), heterogeneous (25-75% of cells stained) and homogeneous (>75% of cells stained).

FFPE samples were derived from tumor micro arrays, as well as human tissue blocks from seven different tumors, as outlined below.

| FFPE Test Samples | | |
| --- | --- | --- |
| Human Tumor Micro Arrays (TMAs) | Description | Commercial Source |
| Mixed tumor | 96 cores from 33 types of cancer | Biomax Cat# MC961 |
| Ovarian tumor | 64 cores | Biochain Cat# T8235725 |
| NSCLC | 80 cores | Biomax Cat# LC806 |
| Colorectal carcinoma | 85 duplicate cores | Biomax Cat# BC000110 |
| Human Tissue Blocks | Number | Commercial Source |
| Breast Tumor | 4 | CHTN |
| Colorectal Carcinoma | 4 | |
| Ovarian Tumor | 4 | |
| NSCLC | 8 | |
| Pancreatic Tumor | 1 | |
| Renal Tumor | 8 | |
| SCCHN | 14 | |

The FOLR1 test article, murine anti-FOLR1 clone BN3.2, was tested to determine binding specificity to the huFOLR1 antigen. Using the reported IHC staining methods, FFPE sections of 300-19 and 300-19 transfected with huFOLR1 (300-10/FOLR1) cell pellets were stained and evaluated for FOLR1. The FOLR1 test article specifically stained 300-19/FOLR1+ cells and returned no staining in 300-19 cells (3 homo and negative, respectively). These results demonstrate that clone BN3.2 specifically targets the huFOLR1 antigen. (FIG. 1).

The BN3.2 antibody was also used to detect FOLR1 expression on tissue samples.

The immunoreactivity of each test and control article with tissues and cell pellets was determined by the consulting pathologist, Dr. David Dorfman. The cell pellet controls were first evaluated followed by tissue samples. For each tissue evaluated, a description of the staining intensity and staining uniformity was reported. The staining intensity score and uniformity scales are described below. The final reported score for each tissue sample evaluated is the score of the test article minus the score of the respective control article. The ABC level for each sample was estimated by comparing the staining score to the calibrated cell pellet controls.

| Intensity (amount of stain) | | Uniformity (number of stained cells) | |
| --- | --- | --- | --- |
| 0 | Negative | | |
| 1 | Weak | 0 | Negative |
| 2 | Moderate | Focal | <25% |
| 3 | Strong | Heterogeneous (hetero) | 25-75% |
| 3+ | Very Strong | Homogeneous (homo) | >75% |

Antibodies bound per cell (ABC) values were determined for the FOLR1-positive tumor cell lines (KB, IGROV1, JEG3, and OVCAR3) using anti-FOLR1-Phycoerythrin, BD Quantibrite Beads, and flow cytometry and were shown to have different ABC values. (FIG. 2). Staining conditions were optimized for FOLR1 so that the cell pellets prepared from the FOLR1-positive tumor cell lines showed varying levels of staining intensity by IHC. The KB cell pellet exhibited very strong (3+) homogeneous staining with high intensity, the IGROV1 cell pellet showed strong (3) staining, the JEG3 cell pellet showed moderate (2-3) heterogeneous staining, while staining of the OVCAR3 cell pellet showed low intensity (1-2) heterogeneous staining. The FOLR1 staining intensity trends observed from the cell pellets correspond to the reported ABC values, where KB cells exhibited the highest ABC value of 1,700,000, IGROV-1 cells exhibited the next highest ABC value of 260,000, JEG-3 exhibited a lower ABC value or 41,000 ABC, while OVCAR3 cells showed the lowest ABC value of 4,000. The staining results and respective ABC values are listed in the table below.

ABC values and respective staining results for huFOLR1 on cell lines and respective cell pellets.

| Cell Line | FOLR1 | |
|---|---|---|
| | ABC | Score |
| KB | 1,700,000 | 3+ homo |
| IGROV1 | 260,000 | 3 homo |
| JEG3 | 41,000 | 2-3 hetero |
| OVCAR3 | 4,000 | 1-2 hetero |

Additional cell lines, including Capan-1, Jar, Hec-1-A, Hec-1-B, Ishikawa, NCI H292, BT474EEI, PA-1, OV-90, CaOv-4, CaOv-3, A2780, Ovcar-5, Ovcar-4, HCT-15, 786-O, NCI H838, NCI H 522, NCI H2110, NCI H1734, NCI H228, and FU.OV-3 were tested and found to be FOLR1 positive but FOLR1 expression levels and sensitivity to the anti-FOLR1 immunoconjugate activity varied. For reference purposes, cell lines having consistent FOLR1 expression and sensitivity to anti-FOLR1 immunoconjugates are preferred.

Particularly important was that the IHC method was able to reliable detected FOLR1 expression in ovarian carcinomas and non-small cell lung cancer (NSCLC) tissue samples. As shown in FIG. 3, FOLR1 expression could reliably be detected in ovarian carcinoma and NSCLC samples scored 2 hetero to 3 homo. ABC values for these samples ranged from approximately 41,000 for samples scored 2 hetero, to greater than 260,000 for samples scored 3 homo. As shown in FIG. 4, high staining intensity and uniformity of staining was also observed in ovarian carcinomas, lung adenocarcinomas, and bronchioloalveoar carcinomas. Furthermore, expression of FOLR1 in NSCLC samples (FIG. 5) and in ovarian carcinomas (FIG. 6) were further found to be predominantly localized to the membrane in tissue samples. Expression was detected across multiple samples from the same, as well as different tumor samples. Interestingly, none of the samples from colorectal, breast, or small cell lung tumors were scored greater than 2 hetero.

Example 2

In Vivo Efficacy of huMov19-PEG4Mal-DM4 and huMov19-SPDB-DM4 Conjugates in Comparison with Similar Non-Targeting Conjugates in a KB Xenograft Model FOLR1-targeting cleavable conjugate huMov19-SPDB-DM4 in comparison with non-targeting huC242-SPDB-DM4, and non-cleavable conjugate huMov19-PEG4-Mal-DM4 in comparison with non-targeting huC242-PEG4Mal-DM4 were tested using an established xenograft model of KB cells (very high FOLR1 expression, 3+ homozygous by manual IHC) implanted subcutaneous into SCID mice. Mice were randomized by body weight into treatment groups and treated either singly (SPDB conjugates) on day 3 post cell inoculation, or three times weekly on days 3, 10, and 17 post cell inoculation with 5 and 10 mg/kg of a conjugate, respectively. The median tumor volume of the different treatment groups is plotted in FIG. 7. The treatments with either huMov19-SPDB-DM4, or huMov19-PEG4Mal-DM4 resulted in a decrease in median tumor volume as compared to the PBS control, while the treatments with either of the respective non-targeting conjugate did not produce any significant effect.

Example 3

Dose-Response Anti-Tumor Activity of IMGN853 Treatment in OVCAR-3 Human Ovarian Carcinoma Xenografts The anti-tumor effect of IMGN853 was evaluated in an established subcutaneous xenograft model of ovarian carcinoma. SCID mice were inoculated with OVCAR-3 ovarian carcinoma cells ($1 \times 10^7$ cells/animal) injected subcutaneously into the right flank. When the tumors reached about 100 mm3 in size (21 days after tumor cell inoculation), the mice were randomly divided into four groups (6 animals per group). Mice were treated with a single intravenous injection of IMGN853 at 1.2, 2.5 or 5.0 mg/kg. A control group of animals received a single intravenous injection of PBS. Tumor growth was monitored by measuring tumor size twice per week. Tumor size was calculated with the formula: length×width×height×½.

IMGN853 was highly active against OVCAR-3 tumors (IHC score of 3 homozygous using manual IHC methods) in terms of tumor growth inhibition (T/C=0%) at both the 2.5 and 5.0 mg/kg dose levels (FIG. 8). There were complete tumor regressions (CR) in 6/6 mice treated with IMGN853 at 5.0 mg/kg. There were partial tumor regressions (PR) in 6/6 mice and CR in 4/6 mice treated with IMGN853 at the 2.5 mg/kg dose level. IMGN853 was active at the 1.2 mg/kg dose level, resulting in a T/C of 18%, with 2/6 PR and 1/6 CR. According to NCI standards the T/C values ranging from 10% to 42% are considered to be active, T/C of less than 10% are considered to be highly active.

Example 4

Dose-Response Anti-Tumor Activity of IMGN853 Treatment in IGROV-1 Human Ovarian Carcinoma Xenografts The anti-tumor effect of IMGN853 was evaluated in an established subcutaneous xenograft model of ovarian carcinoma. SCID mice were inoculated with IGROV-1 ovarian carcinoma cells ($1 \times 10^7$ cells/animal) injected subcutaneously into the right flank. When the tumors reached about 100 mm3 in size (7 days after tumor cell inoculation), the mice were randomly divided into four groups (6 animals per group). Mice were treated with a single intravenous injection of IMGN853 at 1.2, 2.5 or 5.0 mg/kg. A control group of animals received a single intravenous injection of PBS. Tumor growth was monitored by measuring tumor size twice per week. Tumor size was calculated with the formula: length×width×height×½.

IMGN853 was highly active against IGROV-1 tumors (IHC score of 3 homozygous by manual methods) at the 2.5 and 5.0 mg/kg dose levels, resulting in T/C values of 5% for both dose levels (FIG. 9). There were partial tumor regressions in 5/6 and 6/6 mice in the 2.5 and 5.0 mg/kg groups, respectively. IMGN853 was inactive at the 1.2 mg/kg dose (T/C=47%).

Example 5

Dose-Response Anti-Tumor Activity of IMGN853 Treatment in OV-90 Human Ovarian Carcinoma Xenografts The anti-tumor effect of IMGN853 was evaluated in an established subcutaneous xenograft model of ovarian carcinoma. SCID mice were inoculated with OV-90 ovarian carcinoma cells (1×107 cells/animal) injected subcutaneously into the right flank. When the tumors reached about 100 mm3 in size (13 days after tumor cell inoculation), the mice were randomly divided into four groups (6 animals per group). Mice were treated with a single intravenous injection of IMGN853 at 1.2, 2.5 or 5.0 mg/kg. A control group of animals received a single intravenous injection of PBS. A control group of animals received PBS administered intravenously at the same schedule. Tumor growth was monitored by measuring tumor size twice per week. Tumor size was calculated with the formula: length×width×height×½.

IMGN853 was active against OV-90 tumors (IHC score of 3 hetero-homo by manual methods) at the 2.5 and 5.0 mg/kg dose levels, resulting in T/C values of 36 and 18%, respectively (FIG. 10). Two animals had partial tumor regressions in the 5.0 mg/kg group; there were no other tumor regressions in any of the treatment groups. IMGN853 was inactive at the 1.2 mg/kg dose (T/C=77%).

Example 6

Dose-Response Anti-Tumor Activity of IMGN853 Treatment in SKOV-3 Human Ovarian Carcinoma Xenografts The anti-tumor effect of IMGN853 was evaluated in an established subcutaneous xenograft model of ovarian carcinoma. SCID mice were inoculated with SKOV-3 ovarian carcinoma cells (1×10$^7$ cells/animal) injected subcutaneously into the right flank. When the tumors reached about 100 mm3 in size (26 days after tumor cell inoculation), the mice were randomly divided into four groups (6 animals per group). Mice were treated with a single intravenous injection of IMGN853 at 1.2, 2.5 or 5.0 mg/kg. A control group of animals received a single intravenous injection of PBS. Tumor growth was monitored by measuring tumor size twice per week. Tumor size was calculated with the formula: length×width×height×½.

IMGN853 was inactive against SKOV-3 tumors (IHC score of 1-3 focal by manual methods) at all doses, with growth of IMGN853-treated tumors paralleling the PBS control group (FIG. 11). There was no data analysis performed, and the study was terminated early based on the inactivity of IMGN853 in this model.

Example 7

Dose-Response Anti-Tumor Activity of IMGN853 Treatment in KB Human Cervical Adenocarcinoma Xenografts The anti-tumor effect of IMGN853 was evaluated in an established subcutaneous xenograft cervical adenocarcinoma model. SCID mice were inoculated with KB cervical adenocarcinoma cells (1×10$^7$ cells/animal) injected subcutaneously into the right flank. When the tumors reached about 100 mm3 in size (7 days after tumor cell inoculation), the mice were randomly divided into four groups (6 animals per group). Mice were treated with a single intravenous injection of IMGN853 at 1.0, 2.5 or 5.0 mg/kg. A control group of animals received a single intravenous injection of PBS. Tumor growth was monitored by measuring tumor size twice per week. Tumor size was calculated with the formula: length×width×height×½.

IMGN853 was highly active against KB tumors in terms of tumor growth inhibition (T/C=0%) at both the 2.5 and 5.0 mg/kg dose levels (FIG. 12). Six of six mice in the 5.0 mg/kg and five of six mice in the 2.5 mg/kg treatment group had CRs, and remained tumor-free to the end of the study (day 120). The 1.0 mg/kg dose was active, resulting in a T/C of 37%, but there were no partial or complete regressions.

Example 8

Immunohistochemical Staining of FOLR1 in Formalin Fixed Paraffin Embedded (FFPE) Samples—Automated Methods The IHC staining assay uses IVD class I reagents including the Novocastra FOLR1 antibody (Novocastra/Leica Cat #NCI-L-FRalpha, clone BN3.2) as the test article and the Leica Bond RX automated stainer. Bound test or control article were detected by incubation with the Leica Bond Refine detection system which includes a post primary reagent (rabbit anti-mouse IgG), followed by a polymer reagent (goat anti-rabbit polymer) and 3,3-Diaminobenzidine tetrahydrochloride (DAB) chromogen. FFPE samples were stained with the specified concentration(s) of primary antibody (prepared by diluting in Leica diluent FOLR1) as outlined below.

| IHC Antibodies | |
| --- | --- |
| Test article[i] | Folate Receptor Alpha (Novocastra/Leica Cat # NCI-L-FRalpha, Lot 159506), murine, clone BN3.2, liquid concentrate: 75 µg/mL |
| Control article[i] | IgG1 (Beckman Coulter Cat. # 6602872, Lots2S7SPS04-23 and 2S7SPS04-26) stock concentration: 1 mg/mL, murine, clone 2T8-2F5 |

FFPE Assay Method using Leica Bond RX

| Step[i] | Action | Time |
| --- | --- | --- |
| Bake | Temperature: 60° C. | 30 minutes |
| Dewax | Bond Dewax Solution | Fixed |
| | 100% Ethanol | Fixed |
| Antigen Retrieval | Bond ER2 | 20 minutes |
| Endogenous Peroxidase Block | Peroxide (Refine kit component) | 5 minutes |
| Test Article | FOLR1 at 1.9 µg/mL in Leica diluent | 15 minutes |
| Detection | Post Primary Reagent (Refine kit) | 8 minutes |
| | Polymer (Refine kit) | 8 minutes |
| | Mixed DAB (Refine kit) | 10 minutes |
| Counterstain | Hematoxylin (Refine kit) | 5 minutes |

All stained samples were evaluated and scored. Control samples were first evaluated followed by test samples (whole sections and individual cores from the TMAs). For each tumor tissue or cell pellet evaluated, a description of the staining intensity and respective proportion of tumor cells stained was reported. Membrane associated staining was recorded for every sample. When duplicate scores were evaluated from one patient, only the higher score was included in the analysis. If the score described only cytoplasmic staining then the final score was reported as zero (0). Intensity and uniformity were given to each sample as described in the table outlined below. Staining intensity and distribution patterns were scored relative to control IgG staining (non-specific). Intensity was scored on a scale of 0 to 3 (0=no staining, 1=weak, 2=moderate and 3=strong) and distribution was scored as focal (<25% of cells stained), heterogeneous (25-75% of cells stained) and homogeneous (>75% of cells stained). In normal tissue, only the defined substructures were evaluated when calculating intensity and proportion.

IHC Scoring System Consisting of Intensity and Uniformity Scales

| Intensity (brightness of stain) | | |
|---|---|---|
| Intensity Observed | Intensity Category | Intensity Reported |
| 0 | Negative | 0 |
| 0-1 | Very Weak | 1 |
| 1 | Weak | |
| 1-2 | Weak to Moderate | 2 |
| 2 | Moderate | |
| 2-3 | Moderate to Strong | 3 |
| 3 | Strong | |

| Uniformity (percent of stained cells-membrane only) | |
|---|---|
| 0 | Negative |
| Focal | <25% |
| Heterogeneous (hetero) | 25-75% |
| Homogeneous (homo) | >75% |

FFPE tumor samples were derived from tumor micro arrays, as well as human tissue blocks from seven different tumors, as outlined below.

FFPE Test Samples: TMAs

| Anatomic Site | Vendor | Catalog # | Code | Number of Cores per Patient | Total # of Patients |
|---|---|---|---|---|---|
| Kidney | Pantomics | KIC1501 | P-T-ARR-KID-122711-1 | 2 | 69 |
| Lung | Pantomics | LUC1501 | P-T-ARR-LNG-122711-1 | 2 | 70 |
| Lung | Tristar | 69571059/TA1249 | P-T-ARR-OVA-122711-1 | 1 | 110 |
| Ovary | Biochain | T8235725-5 | P-T-ARR-OVA-122111-1 | 1 | 62 |
| Ovary | Pantomics | OVC1501 | P-T-ARR-OVA-122711-1 | 2 | 70 |
| Ovary | Tristar | 69571091/TA1322 | P-T-ARR-OVA-010912-1 | 2 | 96 |
| Uterus (Endometrium) | Pantomics | EMC1501 | P-T-ARR-EME-122711-1 | 2 | 70 |
| Various | Pantomics | MTU481 | P-T-ARR-122711-1 | 1 | 48 |

FFPE Test Samples: Whole Sections

| Organ | Code | Source | Diagnosis (per Source Documentation) |
|---|---|---|---|
| Ovary | 1 | Unknown | endometroid adenocarcinoma |
| | 2 | Proteogenex | endometroid adenocarcinoma |
| | 3 | CHTN | adenocarcinoma, mixed with features of endometriod, serous and clear |
| | 4 | CHTN | adenocarcinoma, high grade w/mixed papillary, serous, endometrioid and clear cell areas |
| | 5 | CHTN | serous papillary adenocarcinoma |
| | 6 | Proteogenex | serous adenocarcinoma |
| | 7 | Proteogenex | serous papillary adenocarcinoma |
| | 8 | Proteogenex | serous papillary adenocarcinoma |
| | 9 | CHTN | serous papillary adenocarcinoma |
| | 10 | Proteogenex | serous papillary adenocarcinoma |
| Lung | 1 | CHTN | adenocarcinoma, poorly differentiated |
| | 2 | CHTN | adenocarcinoma, acinar, well differentiated with bronchioloalveolar features |
| | 3 | CHTN | adenocarcinoma, mucinous features |
| | 4 | CHTN | adenocarcinoma |
| | 5 | CHTN | adenocarcinoma |
| | 6 | CHTN | adenocarcinoma (bronchioloalveolar) carcinoma |
| | 7 | CHTN | adenocarcinoma |
| | 8 | CHTN | adenocarcinoma, moderately differentiated, with clear cell features |
| | 9 | CHTN | adenocarcinoma |
| | 10 | CHTN | squamous cell carcinoma |

Cells (tumor cells or transfected cells) were formalin fixed and paraffin embedded (FFPE). FFPE cell pellet samples shown to exhibit varying ranges of FOLR1 expression by flow cytometry and normal human tissues were used in this study to characterize positive and negative controls and for analysis of specificity. The cell pellets exhibiting varying levels of FOLR1 and the respective scores are reported below. There is a poor correlation between staining scores and the respective FOLR1 expression levels (antibodies bound per cell, ABC, determined by calibrated flow cytometry) in the cell pellets. For example a score of 1-3 hetero is given for the SW620 and IGROV-1 exhibiting 40,098 and 565,481 ABC values, respectively. Additionally, Hela cells showing an ABC value of 1.5 million resulted in a score of 2-3 hetero while 300.19/FR1 exhibiting 830,003 ABC returned a higher score of 3 homo.

Final Scores for Cell Pellets at a Test Article Concentration of 1.9 μg/mL

| Cell Line | $^a$ABC Value | Staining Score |
|---|---|---|
| SW620 | 40,098 | 1-3 hetero |
| T47D | 97,576 | 1-2 hetero |
| IGROV-1 | 565,481 | 1-3 hetero |
| 300.19/FR1 | 830,003 | 3 homo |

-continued

| Cell Line | <sup>a</sup>ABC Value | Staining Score |
|---|---|---|
| HELA | 1,500,587 | 2-3 hetero |
| KB | 4,000,000 | 3 homo |

<sup>a</sup>The reported ABC Value is an average of antibodies bound per cell in the cell population and was determined as follows: a concentration of $1.0 \times 10^{-8}$ M of anti-FOLR1-PE (1:1) was used to determine ABC values on the respective cell line using flow cytometry methods and Quantibrite™ Beads (BD Biosciences).

The flow cytometry histograms represent the distribution of cells versus the number of anti-FOLR1 bound per cell (FOLR1 expression level). Both the histograms and respective IHC staining results indicate that each of these cells lines contain a heterogeneous population of cells having a broad range of FOLR1 expression. The exception is the 300.19/FR1 cell line showing both a uniform flow cytometry histogram and IHC staining score. This data suggests that cell lines each expressing a more uniform level of FOLR1 may provide a better correlation between ABC values and respective staining scores. Although the assay demonstrated positive staining in all FOLR1-positive cell pellet controls, there is a poor correlation between staining scores and the respective FOLR1 expression levels from most of these cell pellets. Therefore, cell pellets from this group could not be identified as high-, medium-, and low-expressing controls. Representative photographs and histograms depicting FOLR1 expression in cell lines by IHC and flow cytometry are shown in FIG. 13.

To determine assay conditions, a range of dilutions of test and control article were tested to select conditions that exhibit an appropriate level of sensitivity. Experiments were performed on a panel of FFPE samples including FOLR1-positive cell pellets and a TMA consisting of FOLR1 positive and negative normal tissues (adrenal (cortex/medulla), breast (ducts and lobules/connective tissue), fallopian tube (surface epithelium/muscle wall), kidney (tubules/glomeruli), lung (type I/II pneumocytes/interalveolar connective tissues), pancreas (ducts/islets of Langerhans), salivary gland (ducts/stroma), skin (eccrine glands/epidermis), stomach (surface epithelium/submucosa)), and whole sections of tumor tissues (10 ovarian tumor samples and 10 lung tumor samples). Each sample was stained with a serial dilution of test article concentrations (0.25, 0.5, 0.9, 1.9, 3.8, and 7.5 µg/mL) or control article concentration of 1.9 µg/mL or 3.8 µg/mL. The relative staining intensities for each dilution were compared for each sample to identify the optimal dilution. The criteria for optimal dilution was a dilution which 1) caused no background staining in samples stained with isotype control 2) caused no staining in negative tissue controls stained with test article and 3) differentiated between varying levels of membrane-associated FOLR1 expression among test samples representing the indication of interest (ovarian tumor, endometrial tumor, NSCLC tumor, and kidney tumor FFPE tissues). Of the five dilutions of test article evaluated, the concentration of 1.9 µg/mL showed the best dynamic range in staining results using the Leica Bond RX automated protocols (Bake and Dewax Protocol, HIER using the ER2 for 20 minutes protocol, and the staining protocol IHC F-With Extra Rinses).

Example 9

Identification and Characterization of Controls that Characterize the Dynamic Range of the Assay-Automated Staining Methods Quality controls: Human normal salivary gland, lung and pancreas were identified as positive tissue controls to be employed in each assay to verify that the staining procedure performed as expected. Human normal esophagus was identified as a negative control. These controls were characterized as follows: in order to establish controls which cover the dynamic range of the assay, a tissue microarray (TMA) consisting of several FOLR1 positive and negative normal tissue samples expected to exhibit the dynamic range of the assay was used as an assay verification control during the optimization and validation phases. Four normal tissues with identified structures in this TMA were identified as suitable assay controls as follows: respiratory epithelium of normal human lung (score of 2 homo); ducts of normal human pancreas (score of 3 homo apical); intercalated ducts of normal human salivary gland (score of 1-2 hetero); and normal human esophagus (score of 0). Over a total of 4 assay runs, the identified suitable assay controls from this TMA gave identical results. These results indicate that the selected controls give consistent results and span the dynamic range of the assay.

Structures in Normal Tissues Identified as Controls that Span the Dynamic Range of the Assay

| Normal Organ | Sub-structure | Staining Score (control article) | Staining Score (test article) |
|---|---|---|---|
| Esophagus | All structures | 0 (negative) | 0 (negative) |
| Salivary Gland | Intercalated ducts | 0 (negative) | 1-2 hetero |
| Lung | Respiratory Epithelium | 0 (negative) | 2 homo |
| Pancreas | Ducts | 0 (negative) | 3 homo apical |

Apical Staining is Defined as Polarized Non-Uniform Membrane Staining

Example 10

Performance Analysis of the Automated Staining Method

The intended use of this assay is to specifically detect FOLR1 reproducibly and with the appropriate sensitivity to differentiate varying levels and varying uniformity of membrane-associated FOLR1 expression (optimal dynamic range) in ovarian, endometrial, NSCLC, and kidney FFPE tumor tissues. Therefore, specificity, reproducibility, and sensitivity were considered as performance criteria.

The specificity and sensitivity of the study assay was evaluated by comparison of normal tissue staining with the study assay to previously reported results. Staining results from this study were compared with corresponding staining results from Scorer et al 2010 (*A Full Immunohistochemical Evaluation of a Novel Monoclonal Antibody to Folate Receptor—alpha*. The Novocastra Journal of Histopathology, REAGENTS: 2010 (3):8-12, describing the same antibody clone BN3.2) with FFPE normal tissue and from the Tissue Cross Reactivity (TCR) study using IMGN853 (huMov19 (M9346A) antibody) on fresh frozen normal tissue (ImmunoGen Report IMH28-003). Comparison of the staining results from each method indicate that the three assays showed generally similar normal tissue staining profiles with differing relative sensitivities, with the Scorer assay being least sensitive, the study assay (IMH28-011) having intermediate sensitivity, and the TCR study method being the most sensitive. Some structures showed positive staining in the two more sensitive methods (study assay and TCR assay) only. There were no examples of positive staining in the least sensitive assay used by Scorer that were not also positive in the study assay and TCR method. These results demonstrate that the specificity and sensitivity of the study assay is appropriate for the evaluation of FOLR1 expression in normal tissues.

The specificity and sensitivity of the study assay was further characterized by staining and evaluating a panel of tumor TMAs consisting of ovarian, endometrial, NSCLC, and kidney tumors (a sample set representative of the assay's intended clinical use). Positive staining was consistently localized to the tumor tissue with normal adjacent tissue components including stroma, blood vessels, lymphocytes and normal organ tissue staining negative or positive as expected. For each subtype of either ovarian carcinoma or NSCLC, the distribution of staining scores among TMAs from the different vendors showed a similar distribution of scores suggesting this method is not sensitive to various fixation and processing conditions. Because the distribution patterns were similar among the TMAs, the data from the different arrays was combined and scores were categorized. A summary of these scores for tumor subtypes that contained 20 or more samples per subtype are listed in the following tables. As summarized in these tables, a dynamic range of scores is noted for each tumor type and indicates that this assay shows the appropriate sensitivity to distinguish varying levels and varying uniformity of membrane-associated FOLR1 expression in ovarian, endometrial, NSCLC, and kidney FFPE tumor tissues. Representative photos of serous ovarian, endometroid ovarian, NSCLC, endometrial carcinoma, and renal clear cell carcinoma are provided in FIGS. 14-18. Additional representatitive photos useful, for example, in a staining guide or diagnostic kit, are shown in FIGS. 23-25. These studies indicate the assay is specific and has the appropriate sensitivity for use as a diagnostic or companion diagnostic reagent.

Summary of Staining Scores for Predominant Subtypes of Ovarian Tumors

| Subtype | Total | Sample Number (%) | | | | | |
|---|---|---|---|---|---|---|---|
| | | ≥3 hetero[a] | ≥2 hetero[a] | ≥1 hetero[a] | 1-3 focal | Any Positivity | Negative |
| Endometrioid | 35 | 15 | 18 | 20 | 6 | 26 | 9 |
| | (100) | (43) | (51) | (57) | (17) | (74) | (26) |
| Mucinous | 29 | 2 | 4 | 5 | 0 | 5 | 24 |
| | (100) | (7) | (14) | (17) | (0) | (17) | (83) |
| Serous | 129 | 44 | 92 | 92 | 8 | 100 | 29 |
| | (100) | (34) | (71) | (71) | (6) | (78) | (22) |

[b]Focal staining patterns were excluded

Summary of Staining Scores for NSCLC Tumors

| Type | Subtype | Total | Sample Number (%) | | | | | |
|---|---|---|---|---|---|---|---|---|
| | | | ≥3 hetero[b] | ≥2 hetero[a] | ≥1 hetero[a] | 1-3 focal | Any Positivity | Negative |
| Adenocarcinoma | All[b] | 67 | 17 | 39 | 42 | 5 | 47 | 20 |
| | | (100) | (25) | (58) | (63) | (7) | 70 | 30 |
| | Specified Bronchiolo-alveolar | 7 | 2 | 5 | 5 | 0 | 5 | 2 |
| | | (100) | (29) | (71) | (71) | (0) | (71) | (29) |
| Squamous cell carcinoma | All | 74 | 1 | 4 | 6 | 6 | 12 | 62 |
| | | (100) | (1) | (5) | (8) | (8) | (16) | (84) |

[b]Focal staining patterns were excluded
All adenocarcinoma samples were included except the specified bronchioloalveolar carcinoma samples Summary of Staining Scores for Adenocarcinoma of the Endometrium and Clear Cell Tumors of the Kidney

|  | | Sample Number (%) | | | | | |
|---|---|---|---|---|---|---|---|
| Tumor/Subtype | Total | ≥3 hetero[a] | ≥2 hetero[a] | ≥1 hetero[a] | 1-3 focal | Any Positivity | Negative |
| Endometrium/Adenocarcinoma | 58 (100) | 5 (9) | 23 (40) | 30 (52) | 10 (17) | 40 (69) | 18 (31) |
| Kidney/Clear Cell | 34 (100) | 0 (0) | 9 (26) | 23 (68) | 6 (18) | 29 (85) | 5 (15) |

Focal staining patterns were excluded

The precision of the study assay was investigated by evaluating intra-run and inter-run reproducibility of the assay using three FFPE tumor tissue samples of ovarian, NSCLC, or kidney tumor where each sample exhibits either a high, medium, or low score. For intra-run reproducibility, nine slides each containing a section of lung, ovarian, and renal tumor were placed at nine random locations on the Leica Bond RX. For inter-run reproducibility, three slides containing sections from the same sample were stained on three different days. All slides from both intra-run and inter-run reproducibility experiments were evaluated and showed equivalent staining results for each respective sample: lung tumor (high: 3 homo), ovarian tumor (medium: 2 hetero), and renal tumor (low: 1-2 hetero). This data demonstrated reproducibility across tissue types with low, medium and high level of expression.

Example 11

A FOLR1 Expression Score of ≥2 Heterogeneous by IHC is a Patient Selection Criterion for Treatment with IMGN853

The levels of FOLR1-expression in tumor cell lines were determined using the an antibody-PE conjugate (FR1-24-PE) and the QuantiBRITE system. Three ovarian carcinoma cell lines (Igrov-1, Skov-3 and Ovcar-3), a choriocarcinoma cell line Jeg-3 and a cervical carcinoma cell line KB were included in the study. In order to obtain reliable ABC values, the binding experiments with an antibody-PE conjugate should be performed at a saturating concentration (concentration, at which all available binding sites are occupied by the conjugate). To determine such concentration for the FR1-24-PE conjugate, we performed binding experiments on a panel of FOLR1-positive cell lines with various FOLR1 expression. The cells were incubated with a wide concentration range of FR1-24-PE conjugate for two hours on ice, washed with FACS buffer (PBS with 1% BSA), fixed with 1% formaldehyde in PBS and analyzed on a FACSCalibur flow cytometer. At a concentration of $1\times10^{-8}$ M the conjugate saturated cell surface binding sites on all tested cell lines Igrov-1, Jeg-3, Skov-3, Ovcar-3, and KB. In subsequent binding ABC-experiments FR1-24-PE conjugate was used at concentration of $1\times10^{-8}$ M. Each sample was analyzed in triplicates; several independent experiments were performed on each cell line. The highest expression was found on KB cells with the approximate ABC value of 4,000,000±300,000, followed by Igrov-1 and Jeg-3 cell lines with the ABC values of 400,000±85,000 and 150,000±75,000, respectively. Two cell lines, Skov-3 and Ovcar-3, had low FOLR1 expression, 20,000±10,000 and 7,000±4,000 ABC, respectively. A significant experiment-to-experiment variation of ABC values was observed for Jeg-3 cells, where the ABC-values varied from 40,000 to 300,000. This variability likely reflected some biological properties of the cell line rather than the assay variability, since ABC values obtained for the other analyzed cell lines were much less variable (see table below).

| Cell line | ABC (Mean ± SD, n)[b] | Experiment-to-experiment variation | |
|---|---|---|---|
| | | The highest ABC registered | The lowest ABC registered |
| KB | 4,000,000 ± 300,000, 4 | 4,500,000 | 3,800,000 |
| Igrov-1 | 400,000 ± 85,000, 5 | 480,000 | 280,000 |
| Jeg-3 | 150,000 ± 75,000, 14 | 260,000 | 40,000 |
| Skov-3 | 20,000 ± 10,000 | 28,000 | 10,000 |
| Ovcar-3 | 7,000 ± 4,000 | 10,000 | 4,000 |

[b]SD—Standard deviation; n—number of independent experiments
ABC values were determined by a FACS based assay with FR1-24 PE-labeled antibody and QuantiBRITE system. Mean ± Standard Deviation (SD) was calculated for independent experiments.

Potency and specificity of IMGN853 was analyzed against FOLR1-positive cell lines with a wide range of FOLR1 expression (the ABC values of the cell lines are provided above). In addition, FOLR1-negative cell lines Namalwa and SW2 were included in the experiments. IMGN853 was highly cytotoxic against cells with high FOLR1 expression KB (4,000,000±300,000 ABC), Igrov-1 (400,000±85,000 ABC) and Jeg-3 (150,000±75,000 ABC), with the $IC_{50}$ values of 0.10±0.01 nM, 0.50±0.07 nM and 1.00±0.05 nM, respectively. The cell-killing activity against all three cell lines was FOLR1-dependent, since an excess of unmodified huMov19 (M9346A) antibody (0.5 µM) markedly decreased potency of the conjugate to the typical non-specific levels (from 10 to 20-fold). IMGN853 was only marginally active against the low FOLR1 expressors Skov-3 and Ovcar-3 cells (20,000±10,000 and 7,000±4,000 ABC, respectively), and against FOLR1-negative cells Namalwa and SW2, with the $IC_{50}$ values greater than 2 nM. The cytotoxic activity of IMGN853 against these cell lines was low and not FOLR1-dependent, as blocking with huMov19 (M9346A) did not affect it. See FIGS. 19 and 20.

FFPE samples prepared from mouse xenograft tumor models were evaluated for FOLR1 positivity using the optimized and validated assay described above. No staining was seen in tumor cells of any xenograft samples stained with control article. FFPE mouse xenograft tissues derived from the following cell lines showed the following staining patterns: Igrov-1, KB, and NCI-H2110 showed homogeneous staining patterns with level 3 intensity; Ishikawa and Ovcar 3 showed heterogeneous staining patterns with level 3 intensity; LXFA737 showed homogeneous staining patterns with level 2 intensity; OV-90 showed heterogenous patterns with level 2 intensity; and SKOV3 was negative. Representative photos of tumor xenografts are provided in FIGS. 21 and 22.

| Parental Cell Line or Tumor Fragment | Disease Indication | Final Score | Staining Category |
|---|---|---|---|
| IGROV-1 | Ovarian cancer | 1-3 homo | 3 homo |
|  |  | 1-3 homo |  |
|  |  | 1-3 homo |  |
| Ishikawa | Endometrium cancer | 2-3 hetero | 3 hetero |
|  |  | 1-2 hetero/3 focal |  |
|  |  | 2 hetero/3 focal |  |
|  |  | 2 hetero/3 focal |  |
| KB | Cervical cancer | 3 homo | 3 homo |
|  |  | 3 homo |  |
| LXFA737 | NSCLC | 2 homo | 2 homo |
|  |  | 2 homo |  |
| NCI-H2110 | NSCLC | 2-3 homo | 3 homo |
|  |  | 2 homo |  |
| OV-90 | Ovarian cancer | 1-2 hetero | 2 hetero |
|  |  | Negative[a] |  |
| OVCAR3 | Ovarian cancer | 1-3 hetero | 3 hetero |
|  |  | 1-3 hetero |  |
| SKOV-3 | Ovarian cancer | Negative | Negative |
|  |  | Negative |  |

A staining threshold (≥2 heterogeneous) requires both a minimal level of expression (staining intensity) and minimum distribution of staining (percentage of tumor cells expressing FOLR1). Pre-clinical data provides justification for this threshold in ovarian carcinoma. Mouse xenograft tumor samples with IHC scores of ≥2 heterogeneous exhibit sensitivity to IMGN 853 in vivo. FFPE samples prepared from mouse xenograft ovarian tumor models were evaluated for FOLR1 positivity using the optimized and validated assay described above. Two ovarian carcinoma xenograft models OVCAR-3, and IGROV-1 showed a heterogeneous or homogeneous staining pattern with level 3 intensity. The xenograft model derived from OV-90 ovarian carcinoma cells showed a heterogeneous staining pattern with level 2 intensity; the Skov-3 ovarian carcinoma model was FOLR1-negative. IMGN853 was highly active in the two ovarian models with level 3 FOLR1 intensity and active in the OV-90 model with level 2 FOLR1 intensity. No activity was observed in the SKOV-3 model. Xenograft models were also evaluated for other diseases indications including lung, endometrium, and cervical tumors and, although correlations were detected between activity and FOLR1 staining scores, additional samples must be tested.

The sensitivity of ovarian tumor xenograft models to IMGN853 versus the level of FOLR1 expression

| Xenograft | In vivo activity (5 mg/kg of IMGN853, single dose) | Intensity score, distribution |
|---|---|---|
| OVCAR3 | Highly active | 3 heterogeneous |
| IGROV-1 | Highly active | 3 homogeneous |
| OV-90 | Active | 2 heterogeneous |
| SKOV-3 | Inactive | Negative |

The sensitivity of other tumor xenograft models to IMGN853 versus the level of FOLR1 expression

| Xenograft | Type of tumor | In vivo activity (5 mg/kg of IMGN853, single dose) | Intensity score, distribution |
|---|---|---|---|
| NCI-H2110 | NSCLC | Highly active | 3 homogeneous |
| Ishikawa | Endometrium | Inactive | 2 homogeneous |
| KB | Cervical | Highly active | 3 homogeneous |

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. A method for treating ovarian cancer comprising administering a therapeutically effective dose of an anti-Folate Receptor 1 (FOLR1) immunoconjugate to a human subject having ovarian cancer; wherein a FOLR1 staining intensity score of 2 or greater has been detected in greater than 75% of the cells in a tumor sample from the human subject using an immunohistochemistry (IHC) detection method that distinguishes between staining intensity and staining uniformity in a FOLR1 expressing cancer sample as compared to staining intensity and staining uniformity in one or more reference samples; wherein the IHC detection method can distinguish between different levels of FOLR1 staining intensity; and wherein the anti-FOLR1 immunoconjugate has the formula (A)-(L)-(C), wherein:

(A) comprises an antibody or antigen binding fragment thereof comprising: (a) a heavy chain CDR1 comprising the amino acid sequence GYFMN (SEQ ID NO:6); a heavy chain CDR2 comprising the amino acid sequence RIHPYDGDTFYNQKFQG (SEQ ID NO:7); and a heavy chain CDR3 comprising the amino acid sequence YDGSRAMDY (SEQ ID NO:8); and (b) a light chain CDR1 comprising the amino acid sequence KASQSVSFAGTSLMH (SEQ ID NO:9); a light chain CDR2 comprising the amino acid sequence RASNLEA (SEQ ID NO:10); and a light chain CDR3 comprising the amino acid sequence QQSREYPYT (SEQ ID NO:11), (L) comprises the linker N-succinimidyl 4-(2-pyridyldithio)-2-sulfobutanoate (sulfo-SPDB), and (C) comprises the cytotoxic agent N(2')-deacetyl-N(2')-(4-mercapto-4-methyl-1-oxopentyl)-maytansine (DM4), and wherein the linker (L) links (A) to (C).

2. The method of claim 1, wherein the antibody or antigen binding fragment thereof of the immunoconjugate comprises a heavy chain variable domain comprising the amino acid sequence of SEQ ID NO: 3 and a light chain variable domain comprising the amino acid sequence of SEQ ID NO: 4 or 5.

3. The method of claim 1, wherein the antibody or antigen binding fragment thereof of the immunoconjugate comprises (i) a heavy chain comprising the same amino acid sequence as the amino acid sequence of the heavy chain encoded by the plasmid deposited with the American Type Culture Collection (ATCC) as PTA-10772 and (ii) a light chain comprising the same amino acid sequence as the amino acid sequence of the light chain encoded by the plasmid deposited with the ATCC as PTA-10773 or PTA-10774.

4. The method of claim 1, further comprising detecting FOLR1 expression in the tumor sample from the human subject using the IHC detection method prior to administering the therapeutically effective dose of the anti-FOLR1 immunoconjugate to the human subject having cancer.

5. The method of claim 1, wherein the IHC detection method produces a range of staining intensity for samples having weak FOLR1 expression, moderate FOLR1 expression, or strong FOLR1 expression.

6. The method of claim 1, wherein the tumor sample is a formalin fixed paraffin embedded sample.

7. The method of claim 1, wherein the reference sample is a negative reference sample.

8. The method of claim 1, wherein the reference sample comprises cells, cell pellets, or tissue.

9. The method of claim 1, wherein the IHC detection method comprises detecting FOLR1 expression with an antibody or antigen binding fragment thereof that specifically binds FOLR1, wherein the antibody or antigen binding fragment thereof for detecting FOLR1 expression comprises (a) a heavy chain CDR1 comprising the amino acid sequence GYFMN (SEQ ID NO:6); a heavy chain CDR2 comprising the amino acid sequence RIHPYDGDTFYNQKFQG (SEQ ID NO:7); and a heavy chain CDR3 comprising the amino acid sequence YDGSRAMDY (SEQ ID NO:8); and (b) a light chain CDR1 comprising the amino acid sequence KASQSVSFAGTSLMH (SEQ ID NO:9); a light chain CDR2 comprising the amino acid sequence RASNLEA (SEQ ID NO:10); and a light chain CDR3 comprising the amino acid sequence QQSREYPYT (SEQ ID NO:11).

10. The method of claim 9, wherein the antibody or antigen binding fragment thereof for detecting FOLR1 expression comprises a heavy chain variable domain comprising the amino acid sequence of SEQ ID NO: 3 and a light chain variable domain comprising the amino acid sequence of SEQ ID NO: 4 or 5.

11. The method of claim 1, wherein the IHC detection method comprises detecting FOLR1 expression with an antibody that specifically binds FOLR1, wherein the antibody for detecting FOLR1 expression comprises (i) a heavy chain comprising the same amino acid sequence as the amino acid sequence of the heavy chain encoded by the plasmid deposited with the ATCC as PTA-10772 and (ii) a light chain comprising the same amino acid sequence as the amino acid sequence of the light chain encoded by the plasmid deposited with the ATCC as PTA-10773 or PTA-10774.

12. The method of claim 1, wherein the IHC detection method comprises detecting FOLR1 expression with an antibody or antigen binding fragment thereof that specifically binds FOLR1, wherein the antibody or antigen binding fragment thereof for detecting FOLR1 expression is the antibody BN3.2.

13. The method of claim 1, wherein the IHC detection method comprises detecting FOLR1 expression with an antibody or antigen binding fragment thereof that specifically binds FOLR1, wherein the antibody or antigen binding fragment thereof for detecting FOLR1 expression further comprises a detection reagent selected from the group consisting of: an enzyme, a fluorophore, a radioactive label, and a luminophore.

14. The method of claim 13, wherein the detection reagent is selected from the group consisting of: biotin, digoxigenin, fluorescein, tritium, and rhodamine.

15. The method of claim 1, wherein a staining intensity score of 3 or greater for FOLR1 expression has been detected in greater than 75% of cells of the tumor sample.

16. A method for treating ovarian cancer comprising:
(a) measuring the level of FOLR1 expression in a tumor tissue sample obtained from a tumor of a human subject having ovarian cancer using an IHC detection method that distinguishes between staining intensity and staining uniformity in the FOLR1 expressing tumor tissue sample as compared to staining intensity and staining uniformity in a reference sample; wherein the IHC detection method can distinguish between different levels of FOLR1 staining intensity;
(b) determining a FOLR1 expression score for the tumor tissue sample based on the level of FOLR1 staining intensity and staining uniformity in the tumor tissue sample;
(c) comparing the FOLR1 expression score for the tumor tissue sample determined in step (b) to a reference FOLR1 expression score determined by measuring FOLR1 staining intensity and staining uniformity in at least one reference sample, wherein a FOLR1 expression score for the tumor tissue sample determined in step (b) that is equal to or higher than the reference FOLR1 expression score identifies the tumor as being sensitive to treatment with an anti-FOLR1 immunoconjugate; and
(d) administering an anti-FOLR1 immunoconjugate to the human subject whose tumor is identified in step (c) as being sensitive to treatment with an anti-FOLR1 immunoconjugate;
wherein greater than 75% of cells of the tumor tissue sample have a staining intensity score of 2 or greater;
wherein the anti-FOLR1 immunoconjugate has the formula (A)-(L)-(C), wherein:
(A) comprises an antibody or antigen binding fragment thereof comprising: (a) a heavy chain CDR1 comprising the amino acid sequence GYFMN (SEQ ID NO:6); a heavy chain CDR2 comprising the amino acid sequence RIHPYDGDTFYNQKFQG (SEQ ID NO:7); and a heavy chain CDR3 comprising the amino acid sequence YDGSRAMDY (SEQ ID NO:8); and (b) a light chain CDR1 comprising the amino acid sequence KASQSVSFAGTSLMH (SEQ ID NO:9); a light chain CDR2 comprising the amino acid sequence RASNLEA (SEQ ID NO:10); and a light chain CDR3 comprising the amino acid sequence QQSREYPYT (SEQ ID NO:11),
(L) comprises the linker N-succinimidyl 4-(2-pyridyldithio)-2-sulfobutanoate (sulfo-SPDB), and
(C) comprises the cytotoxic agent N(2')-deacetyl-N(2')-(4-mercapto-4-methyl-1-oxopentyl)-maytansine (DM4), and
wherein the linker (L) links (A) to (C).

17. The method of claim 16, wherein the antibody or antigen binding fragment thereof of the immunoconjugate comprises a heavy chain variable domain comprising the amino acid sequence of SEQ ID NO: 3 and a light chain variable domain comprising the amino acid sequence of SEQ ID NO: 4 or 5.

18. The method of claim 16, wherein the antibody of the immunoconjugate comprises (i) a heavy chain comprising the same amino acid sequence as the amino acid sequence of the heavy chain encoded by the plasmid deposited with the ATCC as PTA-10772 and (ii) a light chain comprising the same amino acid sequence as the amino acid sequence of the light chain encoded by the plasmid deposited with the ATCC as PTA-10773 or PTA-10774.

19. The method of claim 16, wherein the IHC detection method comprises detecting FOLR1 expression with an antibody or antigen binding fragment thereof that specifically binds FOLR1, wherein the antibody or antigen binding fragment thereof for detecting FOLR1 expression is the antibody BN3.2.

20. The method of claim 16, wherein the reference sample comprises tissue, cells, or cell pellets.

21. The method of claim 16, wherein greater than 75% of cells of the tumor tissue sample have a staining intensity score of 3 or greater for FOLR1 expression.

22. A method for treating ovarian cancer comprising:
(a) contacting a tumor tissue sample from a human subject having ovarian cancer with an antibody or antigen binding fragment thereof that specifically binds FOLR1, wherein the sample is formalin-fixed paraffin embedded;
(b) measuring the binding of the antibody or antigen binding fragment thereof to FOLR1 in the tumor tissue sample in step (a) using an IHC detection method that can distinguish between staining intensity and staining uniformity in the FOLR1 expressing tumor tissue sample as compared to staining intensity or staining uniformity in one or more reference samples;
(c) assigning a FOLR1 expression score to the tumor tissue sample after comparing the level of FOLR1 staining intensity and staining uniformity in the tumor tissue sample to one or more reference samples; and
(d) administering an anti-FOLR1 immunoconjugate to the human subject whose tumor tissue sample has greater than 75% of cells having a FOLR1 staining intensity score of 2 or greater;
wherein the anti-FOLR1 immunoconjugate has the formula (A)-(L)-(C), wherein:
(A) comprises an antibody or antigen binding fragment thereof comprising: (a) a heavy chain CDR1 comprising the amino acid sequence GYFMN (SEQ ID NO:6); a heavy chain CDR2 comprising the amino acid sequence RIHPYDGDTFYNQKFQG (SEQ ID NO:7); and a heavy chain CDR3 comprising the amino acid sequence YDGSRAMDY (SEQ ID NO:8);
and (b) a light chain CDR1 comprising the amino acid sequence KASQSVSFAGTSLMH (SEQ ID NO:9); a light chain CDR2 comprising the amino acid sequence RASNLEA (SEQ ID NO:10); and a light chain CDR3 comprising the amino acid sequence QQSREYPYT (SEQ ID NO:11),
(L) comprises the linker N-succinimidyl 4-(2-pyridyldithio)-2-sulfobutanoate (sulfo-SPDB), and
(C) comprises the cytotoxic agent N(2')-deacetyl-N(2')-(4-mercapto-4-methyl-1-oxopentyl)-maytansine (DM4), and
wherein the linker (L) links (A) to (C).

23. The method of claim 22, wherein the antibody or antigen binding fragment thereof of the immunoconjugate comprises a heavy chain variable domain comprising the amino acid sequence of SEQ ID NO: 3 and a light chain variable domain comprising the amino acid sequence of SEQ ID NO: 4 or 5.

24. The method of claim 23, wherein the antibody of the immunoconjugate comprises (i) a heavy chain comprising the same amino acid sequence as the amino acid sequence of the heavy chain encoded by the plasmid deposited with the ATCC as PTA-10772 and (ii) a light chain comprising the same amino acid sequence as the amino acid sequence of the light chain encoded by the plasmid deposited with the ATCC as PTA-10773 or PTA-10774.

25. The method of claim 22, wherein the reference sample comprises tissue, cells, or cell pellets.

26. The method of claim 22, wherein the reference sample is a negative reference sample.

27. The method of claim 22, wherein the antibody or antigen binding fragment thereof for detecting F OLR1 expression is the antibody BN3.2.

28. The method of claim 22, wherein the tumor tissue sample has greater than 75% of cells having a staining intensity score of 3 or greater.

* * * * *